(12) United States Patent
Butora et al.

(10) Patent No.: US 7,534,767 B2
(45) Date of Patent: May 19, 2009

(54) C-PURINE NUCLEOSIDE ANALOGS AS INHIBITORS OF RNA-DEPENDENT RNA VIRAL POLYMERASE

(75) Inventors: Gabor Butora, Martinsville, NJ (US); Malcolm MacCoss, Freehold, NJ (US); Balkrishen Bhat, Carlsbad, CA (US); Anne B. Eldrup, Danbury, CT (US)

(73) Assignee: Merck & Co., Inc., Rahway, NJ (US)

( * ) Notice: Subject to any disclaimer, the term of this patent is extended or adjusted under 35 U.S.C. 154(b) by 130 days.

(21) Appl. No.: 11/628,513

(22) PCT Filed: Jun. 10, 2005

(86) PCT No.: PCT/US2005/020757

§ 371 (c)(1),
(2), (4) Date: Dec. 4, 2006

(87) PCT Pub. No.: WO2005/123087

PCT Pub. Date: Dec. 29, 2005

(65) Prior Publication Data

US 2008/0021047 A1      Jan. 24, 2008

Related U.S. Application Data

(60) Provisional application No. 60/579,823, filed on Jun. 15, 2004.

(51) Int. Cl.
*A01N 43/04*     (2006.01)
(52) U.S. Cl. .......................................... 514/23; 536/29.2
(58) Field of Classification Search .................. None
See application file for complete search history.

(56) References Cited

U.S. PATENT DOCUMENTS

| | | | |
|---|---|---|---|
| 6,777,395 B2 | 8/2004 | Bhat et al. | |
| 2004/0063658 A1 | 4/2004 | Roberts et al. | |

FOREIGN PATENT DOCUMENTS

| | | |
|---|---|---|
| EP | 0 071 227 A1 | 2/1983 |
| WO | WO 01/90121 A2 | 11/2001 |
| WO | WO 02/057287 A2 | 7/2002 |
| WO | WO 02/057425 A2 | 7/2002 |
| WO | WO 03/093290 A2 | 11/2003 |
| WO | WO 2004/002999 A2 | 1/2004 |
| WO | WO 2004/002999 A3 | 1/2004 |
| WO | WO 2004/003000 A3 | 1/2004 |
| WO | WO 2004/046331 A2 | 6/2004 |
| WO | WO 2004/058792 A1 | 7/2004 |
| WO | WO 2005/009418 A2 | 2/2005 |
| WO | WO 2005/021568 A2 | 3/2005 |
| WO | WO 2006/050161 A2 | 5/2006 |
| WO | WO 2006/104945 A2 | 10/2006 |

*Primary Examiner*—Patrick T Lewis
(74) *Attorney, Agent, or Firm*—Kenneth R. Walton; Sheldon O. Heber; Philippe L. Durette

(57) ABSTRACT

The present invention provides C-purine nucleoside analogs and certain derivatives thereof which are inhibitors of RNA-dependent RNA viral polymerase. These compounds are inhibitors RNA-dependent RNA viral replication and are useful for the treatment of RNA-dependent RNA viral infection. They are particularly useful as inhibitors of hepatitis C virus (HCV) NS5B polymerase, as inhibitors of HCV replication, and/or for the treatment of hepatitis C infection. The invention also describes pharmaceutical compositions containing such C-nucleoside compounds alone or in combination with other agents active against RNA-dependent RNA viral infection, in particular HCV infection. Also disclosed are methods of inhibiting RNA-dependent RNA polymerase, inhibiting RNA-dependent RNA viral replication, and/or treating RNA-dependent RNA viral infection with the C-nucleoside compounds of the present invention.

23 Claims, No Drawings

C-PURINE NUCLEOSIDE ANALOGS AS INHIBITORS OF RNA-DEPENDENT RNA VIRAL POLYMERASE

CROSS REFERENCE TO RELATED APPLICATIONS

This application is the National Stage of International Application No. PCT/US2005/020757, filed 10 Jun. 2005, which claims the benefit under 35 U.S.C. 119(e) of U.S. Provisional Application No. 60/579,823, filed 15 Jun. 2004.

FIELD OF THE INVENTION

The present invention is concerned with C-purine nucleoside analogs and certain derivatives thereof, their synthesis, and their use as inhibitors of RNA-dependent RNA viral polymerase. The compounds of the present invention are inhibitors of RNA-dependent RNA viral replication and are useful for the treatment of RNA-dependent RNA viral infection. They are particularly useful as inhibitors of hepatitis C virus (HCV) NS5B polymerase, as inhibitors of HCV replication, and for the treatment of hepatitis C infection.

BACKGROUND OF THE INVENTION

Hepatitis C virus (HCV) infection is a major health problem that leads to chronic liver disease, such as cirrhosis and hepatocellular carcinoma, in a substantial number of infected individuals, estimated to be 2-15% of the world's population. There are an estimated 4.5 million infected people in the United States alone, according to the U.S. Center for Disease Control. According to the World Health Organization, there are more than 200 million infected individuals worldwide, with at least 3 to 4 million people being infected each year. Once infected, about 20% of people clear the virus, but the rest harbor HCV the rest of their lives. Ten to twenty percent of chronically infected individuals eventually develop liver-destroying cirrhosis or cancer. The viral disease is transmitted parenterally by contaminated blood and blood products, contaminated needles, or sexually and vertically from infected mothers or carrier mothers to their off-spring. Current treatments for HCV infection, which are restricted to immunotherapy with recombinant interferon-α alone or in combination with the nucleoside analog ribavirin, are of limited clinical benefit. Moreover, there is no established vaccine for HCV. Consequently, there is an urgent need for improved therapeutic agents that effectively combat chronic HCV infection. The state of the art in the treatment of HCV infection has been reviewed, and reference is made to the following publications: B. Dymock, et al., "Novel approaches to the treatment of hepatitis C virus infection," *Antiviral Chemistry & Chemotherapy,* 11: 79-96 (2000); H. Rosen, et al., "Hepatitis C virus: current understanding and prospects for future therapies," *Molecular Medicine Today,* 5: 393-399 (1999); D. Moradpour, et al., "Current and evolving therapies for hepatitis C," *European J. Gastroenterol. Hepatol.,* 11: 1189-1202 (1999); R. Bartenschlager, "Candidate Targets for Hepatitis C Virus-Specific Antiviral Therapy," *Intervirology,* 40: 378-393 (1997); G. M. Lauer and B. D. Walker, "Hepatitis C Virus Infection," *N. Engl. J. Med.,* 345: 41-52 (2001); B. W. Dymock, "Emerging therapies for hepatitis C virus infection," *Emerging Drugs,* 6: 13-42 (2001); and C. Crabb, "Hard-Won Advances Spark Excitement about Hepatitis C," *Science:* 506-507 (2001); the contents of all of which are incorporated by reference herein in their entirety.

Different approaches to HCV therapy have been taken, which include the inhibition of viral serine proteinase (NS3 protease), helicase, and RNA-dependent RNA polymerase (NS5B), and the development of a vaccine.

The HCV virion is an enveloped positive-strand RNA virus with a single oligoribonucleotide genomic sequence of about 9600 bases which encodes a polyprotein of about 3,010 amino acids. The protein products of the HCV gene consist of the structural proteins C, E1, and E2, and the non-structural proteins NS2, NS3, NS4A and NS4B, and NS5A and NS5B. The nonstructural (NS) proteins are believed to provide the catalytic machinery for viral replication. The NS3 protease releases NS5B, the RNA-dependent RNA polymerase from the polyprotein chain. HCV NS5B polymerase is required for the synthesis of a double-stranded RNA from a single-stranded viral RNA that serves as a template in the replication cycle of HCV. NS5B polymerase is therefore considered to be an essential component in the HCV replication complex [see K. Ishi, et al., "Expression of Hepatitis C Virus NS5B Protein: Characterization of Its RNA Polymerase Activity and RNA Binding," *Hepatology,* 29: 1227-1235 (1999) and V. Lohmann, et al., "Biochemical and Kinetic Analyses of NS5B RNA-Dependent RNA Polymerase of the Hepatitis C Virus," *Virology,* 249: 108-118 (1998)]. Inhibition of HCV NS5B polymerase prevents formation of the double-stranded HCV RNA and therefore constitutes an attractive approach to the development of HCV-specific antiviral therapies.

The development of inhibitors of HCV NS5B polymerase with potential for the treatment of HCV infection has been reviewed in M. P. Walker et al., "Promising candidates for the treatment of chronic hepatitis C," *Expert Opin. Invest. Drugs,* 12: 1269-1280 (2003) and in P. Hoffmann et al., "Recent patents on experimental therapy for hepatitis C virus infection (1999-2002)," *Expert Opin. Ther. Patents,"* 13: 1707-1723 (2003). The activity of purine ribonucleosides against HCV polymerase was reported by A. E. Eldrup et al., "Structure-Activity Relationship of Purine Ribonucleosides for Inhibition of HCV RNA-Dependent RNA Polymerase," *J. Med. Chem.,* 47: 2283-2295 (2004). There is a continuing need for structurally diverse nucleoside derivatives as inhibitors of HCV polymerase as therapeutic approaches for HCV therapy.

It has now been found that C-nucleoside compounds of the present invention and certain derivatives thereof are potent inhibitors of RNA-dependent RNA viral replication and in particular HCV replication. The 5'-triphosphate derivatives of these C-nucleoside compounds are inhibitors of RNA-dependent RNA viral polymerase and in particular HCV NS5B polymerase. The instant C-nucleoside compounds and derivatives thereof are useful to treat RNA-dependent RNA viral infection and in particular HCV infection.

It is therefore an object of the present invention to provide C-nucleoside compounds and certain derivatives thereof which are useful as inhibitors of RNA-dependent RNA viral polymerase and in particular as inhibitors of HCV NS5B polymerase.

It is another object of the present invention to provide C-nucleoside compounds and certain derivatives thereof which are useful as inhibitors of the replication of an RNA-dependent RNA virus and in particular as inhibitors of the replication of hepatitis C virus.

It is another object of the present invention to provide C-nucleoside compounds and certain derivatives thereof which are useful in the treatment of RNA-dependent RNA viral infection and in particular in the treatment of HCV infection.

It is another object of the present invention to provide pharmaceutical compositions comprising the C-nucleoside compounds of the present invention in association with a pharmaceutically acceptable carrier.

It is another object of the present invention to provide pharmaceutical compositions comprising the C-nucleoside compounds and derivatives thereof of the present invention for use as inhibitors of RNA-dependent RNA viral polymerase and in particular as inhibitors of HCV NS5B polymerase.

It is another object of the present invention to provide pharmaceutical compositions comprising the C-nucleoside compounds and derivatives thereof of the present invention for use as inhibitors of RNA-dependent RNA viral replication and in particular as inhibitors of HCV replication.

It is another object of the present invention to provide pharmaceutical compositions comprising the C-nucleoside compounds and derivatives thereof of the present invention for use in the treatment of RNA-dependent RNA viral infection and in particular in the treatment of HCV infection.

It is another object of the present invention to provide pharmaceutical compositions comprising the C-nucleoside compounds and derivatives thereof of the present invention in combination with other agents active against an RNA-dependent RNA virus and in particular against HCV.

It is another object of the present invention to provide methods for the inhibition of RNA-dependent RNA viral polymerase and in particular for the inhibition of HCV NS5B polymerase.

It is another object of the present invention to provide methods for the inhibition of RNA-dependent RNA viral replication and in particular for the inhibition of HCV replication.

It is another object of the present invention to provide methods for the treatment of RNA-dependent RNA viral infection and in particular for the treatment of HCV infection.

It is another object of the present invention to provide methods for the treatment of RNA-dependent RNA viral infection in combination with other agents active against RNA-dependent RNA virus and in particular for the treatment of HCV infection in combination with other agents active against HCV.

It is another object of the present invention to provide C-nucleoside compounds and certain derivatives thereof and their pharmaceutical compositions for use as a medicament for the inhibition of RNA-dependent RNA viral replication and/or the treatment of RNA-dependent RNA viral infection and in particular for the inhibition of HCV replication and/or the treatment of HCV infection.

It is another object of the present invention to provide for the use of the C-nucleoside compounds and certain derivatives thereof of the present invention and their pharmaceutical compositions for the manufacture of a medicament for the inhibition of RNA-dependent RNA viral replication and/or the treatment of RNA-dependent RNA viral infection and in particular for the inhibition of HCV replication and/or the treatment of HCV infection.

These and other objects will become readily apparent from the detailed description which follows.

SUMMARY OF THE INVENTION

The present invention relates to compounds of structural formula I of the indicated stereochemical configuration:

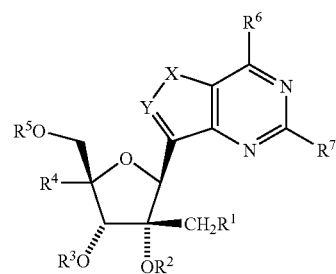

or a pharmaceutically acceptable salt thereof; wherein
X is O, S, or NR$^8$;
Y is CR$^{11}$ or N;
R$^1$ is selected from the group consisting of hydrogen, fluoro, azido, amino, hydroxy, C$_{1-3}$ alkoxy, mercapto, and C$_{1-3}$ alkylthio;
R$^2$ and R$^3$ are each independently selected from the group consisting of hydrogen, methyl, C$_{1-16}$ alkylcarbonyl, C$_{2-18}$ alkenylcarbonyl, C$_{1-10}$ alkyloxycarbonyl, C$_{3-6}$ cycloalkylcarbonyl, C$_{3-6}$ cycloalkyloxycarbonyl, CH$_2$O(C=O)C$_{1-4}$ alkyl, CH(C$_{1-4}$ alkyl)O(C=O)C$_{1-4}$ alkyl, or an amino acyl residue of structural formula

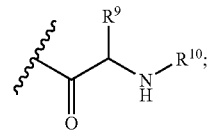

R$^4$ is hydrogen, azido, methyl, hydroxymethyl, or fluoromethyl;
R$^5$ is hydrogen, C$_{1-10}$ alkylcarbonyl, phosphoryl or a cyclic prodrug ester thereof, diphosphoryl, triphosphoryl, C$_{2-18}$ alkenylcarbonyl, C$_{1-10}$ alkyloxycarbonyl, C$_{3-6}$ cycloalkylcarbonyl, C$_{3-6}$ cycloalkyloxycarbonyl, CH$_2$O(C=O)C$_{1-4}$ alkyl, CH(C$_{1-4}$ alkyl)O(C=O)C$_{1-4}$ alkyl, or an amino acyl residue of structural formula

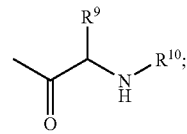

R$^6$ and R$^7$ are each independently hydrogen, hydroxy, halogen, C$_{1-4}$ alkoxy, amino, C$_{1-4}$ alkylamino, di(C$_{1-4}$ alkyl) amino, C$_{3-6}$ cycloalkylamino, di(C$_{3-6}$ cycloalkyl)amino, benzylamino, dibenzylamino, or C$_{4-6}$ heterocycloalkyl, wherein alkyl, cycloalkyl, benzyl, and heterocycloalkyl are unsubstituted or substituted with one to five groups independently selected from halogen, hydroxy, amino, C$_{1-4}$ alkyl, and C$_{1-4}$ alkoxy;
R$^8$ is hydrogen or C$_{1-4}$ alkyl;
R$^9$ is hydrogen, C$_{1-5}$ alkyl, or phenyl C$_{0-2}$ alkyl;
R$^{10}$ is hydrogen, C$_{1-4}$ alkyl, C$_{1-4}$ acyl, benzoyl, C$_{1-4}$ alkyloxycarbonyl, phenyl C$_{0-2}$ alkyloxycarbonyl, C$_{1-4}$ alkylaminocarbonyl, phenyl C$_{0-2}$ alkylaminocarbonyl, C$_{1-4}$ alkylsulfonyl, or phenyl C$_{0-2}$ alkylsulfonyl; and
R$^{11}$ is hydrogen, halogen, methyl, azido, or amino.

The compounds of formula I are useful as inhibitors of RNA-dependent RNA viral polymerase and in particular of HCV NS5B polymerase. They are also inhibitors of RNA-dependent RNA viral replication and in particular of HCV replication and are useful for the treatment of RNA-dependent RNA viral infection and in particular for the treatment of HCV infection.

Also encompassed within the present invention are pharmaceutical compositions containing the compounds alone or in combination with other agents active against RNA-dependent RNA virus and in particular against HCV as well as methods for the inhibition of RNA-dependent RNA viral replication and for the treatment of RNA-dependent RNA viral infection.

DETAILED DESCRIPTION OF THE INVENTION

The present invention relates to compounds of structural formula I of the indicated stereochemical configuration:

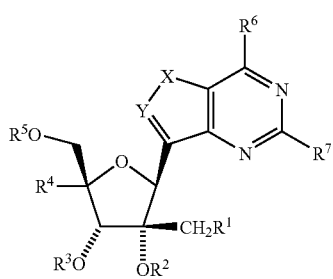

(I)

or a pharmaceutically acceptable salt thereof; wherein

X is O, S, or $NR^8$;

Y is $CR^{11}$ or N;

$R^1$ is selected from the group consisting of hydrogen, fluoro, azido, amino, hydroxy, $C_{1-3}$ alkoxy, mercapto, and $C_{1-3}$ alkylthio;

$R^2$ and $R^3$ are each independently selected from the group consisting of hydrogen, methyl, $C_{1-16}$ alkylcarbonyl, $C_{2-18}$ alkenylcarbonyl, $C_{1-10}$ alkyloxycarbonyl, $C_{3-6}$ cycloalkylcarbonyl, $C_{3-6}$ cycloalkyloxycarbonyl, $CH_2O(C{=}O)C_{1-4}$ alkyl, $CH(C_{1-4}$ alkyl$)O(C{=}O)C_{1-4}$ alkyl, or an amino acyl residue of structural formula

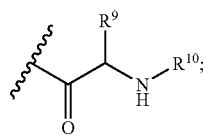

$R^4$ is hydrogen, azido, methyl, hydroxymethyl, or fluoromethyl;

$R^5$ is hydrogen, $C_{1-10}$ alkylcarbonyl, phosphoryl or a cyclic prodrug ester thereof, diphosphoryl, triphosphoryl, $C_{2-18}$ alkenylcarbonyl, $C_{1-10}$ alkyloxycarbonyl, $C_{3-6}$ cycloalkylcarbonyl, $C_{3-6}$ cycloalkyloxycarbonyl, $CH_2O(C{=}O)C_{1-4}$ alkyl, $CH(C_{1-4}$ alkyl$)O(C{=}O)C_{1-4}$ alkyl, or an amino acyl residue of structural formula

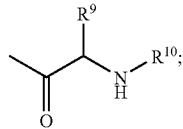

$R^6$ and $R^7$ are each independently hydrogen, hydroxy, halogen, $C_{1-4}$ alkoxy, amino, $C_{1-4}$ alkylamino, di($C_{1-4}$ alkyl)amino, $C_{3-6}$ cycloalkylamino, di($C_{3-6}$ cycloalkyl)amino, benzylamino, dibenzylamino, or $C_{4-6}$ heterocycloalkyl, wherein alkyl, cycloalkyl, benzyl, and heterocycloalkyl are unsubstituted or substituted with one to five groups independently selected from halogen, hydroxy, amino, $C_{1-4}$ alkyl, and $C_{1-4}$ alkoxy;

$R^8$ is hydrogen or $C_{1-4}$ alkyl;

$R^9$ is hydrogen, $C_{1-5}$ alkyl, or phenyl $C_{0-2}$ alkyl;

$R^{10}$ is hydrogen, $C_{1-4}$ alkyl, $C_{1-4}$ acyl, benzoyl, $C_{1-4}$ alkyloxycarbonyl, phenyl $C_{0-2}$ alkyloxycarbonyl, $C_{1-4}$ alkylaminocarbonyl, phenyl $C_{0-2}$ alkylaminocarbonyl, $C_{1-4}$ alkylsulfonyl, or phenyl $C_{0-2}$ alkylsulfonyl; and $R^{11}$ is hydrogen, halogen, methyl, azido, or amino.

The compounds of formula I are useful as inhibitors of RNA-dependent RNA viral polymerase. They are also inhibitors of RNA-dependent RNA viral replication and are useful for the treatment of RNA-dependent RNA viral infection.

In one embodiment of the compounds of structural formula I, Y is CH, and X is O, S, or $NR^8$. In a class of this embodiment, X is O. In another class of this embodiment, X is $NR^8$. In a subclass of this class, $R^8$ is hydrogen.

In a second embodiment of the compounds of structural formula I, Y is N, and X is O, S, or $NR^8$. In a class of this second embodiment, X is O. In another class of this second embodiment, X is $NR^8$. In a subclass of this class, $R^8$ is hydrogen.

In a third embodiment of the compounds of the present invention, $R^1$ and $R^4$ are both hydrogen. In a class of this third embodiment, $R^2$, $R^3$, and $R^5$ are hydrogen. In a subclass of this class, $R^6$ and $R^7$ are each independently hydrogen, amino, fluoro, or hydroxy.

In a fourth embodiment of the compounds of the present invention, Y is N; X is $NR^8$; $R^1$, $R^2$, $R^3$, $R^4$, and $R^5$ are hydrogen; and $R^6$ and $R^7$ are each independently hydrogen, amino, fluoro, or hydroxy. In a class of this fourth embodiment, $R^8$ is hydrogen.

In a fifth embodiment of the compounds of the present invention, Y is CH; X is $NR^8$; $R^1$, $R^2$, $R^3$, $R^4$, and $R^5$ are hydrogen; and $R^6$ and $R^7$ are each independently hydrogen, amino, fluoro, or hydroxy. In a class of this fifth embodiment, $R^8$ is hydrogen.

In a sixth embodiment of the compounds of the present invention, Y is N; X is O; $R^1$, $R^2$, $R^3$, $R^4$, and $R^5$ are hydrogen; and $R^6$ and $R^7$ are each independently hydrogen, amino, fluoro, or hydroxy. In a class of this sixth embodiment, $R^8$ is hydrogen.

In a seventh embodiment of the compounds of the present invention, Y is CH; X is O; $R^1$, $R^2$, $R^3$, $R^4$, and $R^5$ are hydrogen; and $R^6$ and $R^7$ are each independently hydrogen, amino, fluoro, or hydroxy. In a class of this seventh embodiment, $R^8$ is hydrogen.

Illustrative but nonlimiting examples of compounds of the present invention of structural formula I which are useful as inhibitors of RNA-dependent RNA viral polymerase are the following:

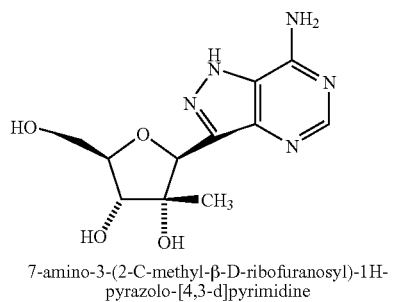

7-amino-3-(2-C-methyl-β-D-ribofuranosyl)-1H-pyrazolo-[4,3-d]pyrimidine

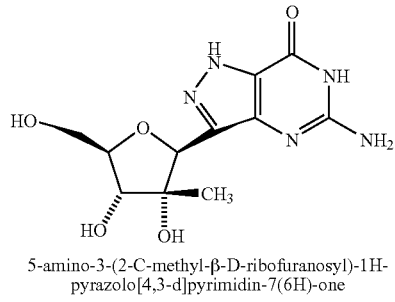

5-amino-3-(2-C-methyl-β-D-ribofuranosyl)-1H-pyrazolo[4,3-d]pyrimidin-7(6H)-one

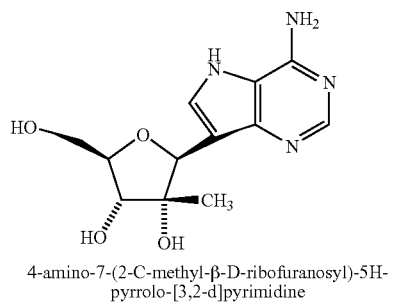

4-amino-7-(2-C-methyl-β-D-ribofuranosyl)-5H-pyrrolo-[3,2-d]pyrimidine

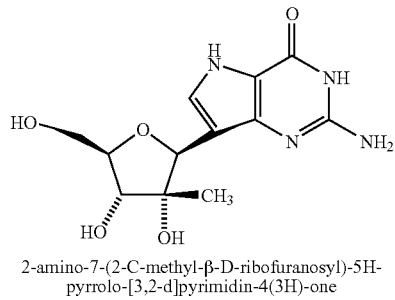

2-amino-7-(2-C-methyl-β-D-ribofuranosyl)-5H-pyrrolo-[3,2-d]pyrimidin-4(3H)-one

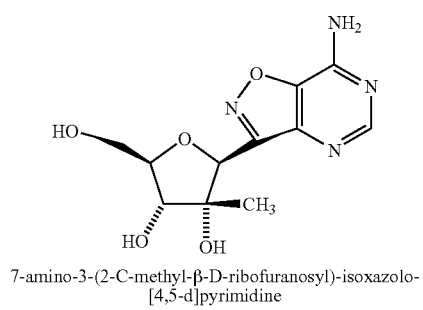

7-amino-3-(2-C-methyl-β-D-ribofuranosyl)-isoxazolo-[4,5-d]pyrimidine

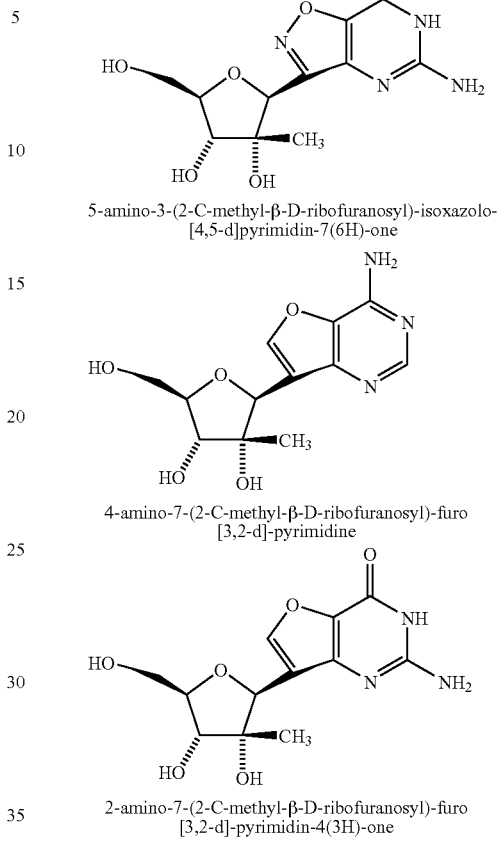

5-amino-3-(2-C-methyl-β-D-ribofuranosyl)-isoxazolo-[4,5-d]pyrimidin-7(6H)-one 4-amino-7-(2-C-methyl-β-D-ribofuranosyl)-furo[3,2-d]-pyrimidine 2-amino-7-(2-C-methyl-β-D-ribofuranosyl)-furo[3,2-d]-pyrimidin-4(3H)-one or a pharmaceutically acceptable salt thereof.

In one embodiment of the present invention, the C-nucleoside compounds of the present invention are useful as inhibitors of positive-sense single-stranded RNA-dependent RNA viral polymerase, inhibitors of positive-sense single-stranded RNA-dependent RNA viral replication, and/or for the treatment of positive-sense single-stranded RNA-dependent RNA viral infection. In a class of this embodiment, the positive-sense single-stranded RNA-dependent RNA virus is a Flaviviridae virus or a Picornaviridae virus. In a subclass of this class, the Picornaviridae virus is a rhinovirus, a poliovirus, or a hepatitis A virus. In a second subclass of this class, the Flaviviridae virus is selected from the group consisting of hepatitis C virus, yellow fever virus, dengue virus, West Nile virus, Japanese encephalitis virus, Banzi virus, and bovine viral diarrhea virus (BVDV). In a subclass of this subclass, the Flaviviridae virus is hepatitis C virus.

Another aspect of the present invention is concerned with a method for inhibiting RNA-dependent RNA viral polymerase, a method for inhibiting RNA-dependent RNA viral replication, and/or a method for treating RNA-dependent RNA viral infection in a mammal in need thereof comprising administering to the mammal a therapeutically effective amount of a compound of structural formula I.

In one embodiment of this aspect of the present invention, the RNA-dependent RNA viral polymerase is a positive-sense single-stranded RNA-dependent RNA viral polymerase. In a class of this embodiment, the positive-sense single-stranded RNA-dependent RNA viral polymerase is a Flaviviridae viral polymerase or a Picornaviridae viral polymerase. In a subclass of this class, the Picornaviridae viral polymerase is rhinovirus polymerase, poliovirus polymerase, or hepatitis A virus polymerase. In a second subclass of this class, the Flaviviridae viral polymerase is selected from the group consisting of hepatitis C virus polymerase, yellow fever virus polymerase, dengue virus polymerase, West Nile virus polymerase, Japanese encephalitis virus polymerase, Banzi virus polymerase, and bovine viral diarrhea virus (BVDV) polymerase. In a subclass of this subclass, the Flaviviridae viral polymerase is hepatitis C virus polymerase.

In a second embodiment of this aspect of the present invention, the RNA-dependent RNA viral replication is a positive-sense single-stranded RNA-dependent RNA viral replication. In a class of this embodiment, the positive-sense single-stranded RNA-dependent RNA viral replication is Flaviviridae viral replication or Picornaviridae viral replication. In a subclass of this class, the Picornaviridae viral replication is rhinovirus replication, poliovirus replication, or hepatitis A virus replication. In a second subclass of this class, the Flaviviridae viral replication is selected from the group consisting of hepatitis C virus replication, yellow fever virus replication, dengue virus replication, West Nile virus replication, Japanese encephalitis virus replication, Banzi virus replication, and bovine viral diarrhea virus replication. In a subclass of this subclass, the Flaviviridae viral replication is hepatitis C virus replication.

In a third embodiment of this aspect of the present invention, the RNA-dependent RNA viral infection is a positive-sense single-stranded RNA-dependent viral infection. In a class of this embodiment, the positive-sense single-stranded RNA-dependent RNA viral infection is Flaviviridae viral infection or Picornaviridae viral infection. In a subclass of this class, the Picornaviridae viral infection is rhinovirus infection, poliovirus infection, or hepatitis A virus infection. In a second subclass of this class, the Flaviviridae viral infection is selected from the group consisting of hepatitis C virus infection, yellow fever virus infection, dengue virus infection, West Nile virus infection, Japanese encephalitis virus infection, Banzi virus infection, and bovine viral diarrhea virus infection. In a subclass of this subclass, the Flaviviridae viral infection is hepatitis C virus infection.

Throughout the instant application, the following terms have the indicated meanings:

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The term "alkenyl" shall mean straight or branched chain alkenes of two to six total carbon atoms, or any number within this range (e.g., ethenyl, propenyl, butenyl, pentenyl, etc.).

The term "alkynyl" shall mean straight or branched chain alkynes of two to six total carbon atoms, or any number within this range (e.g., ethynyl, propynyl, butynyl, pentynyl, etc.).

The term "cycloalkyl" shall mean cyclic rings of alkanes of three to eight total carbon atoms, or any number within this range (i.e., cyclopropyl, cyclobutyl, cyclopentyl, cyclohexyl, cycloheptyl, or cyclooctyl).

The term "cycloheteroalkyl" is intended to include non-aromatic heterocycles containing one or two heteroatoms selected from nitrogen, oxygen and sulfur. Examples of 4-6-membered cycloheteroalkyl include azetidinyl, pyrrolidinyl, piperidinyl, morpholinyl, thiamorpholinyl, imidazolidinyl, tetrahydrofuranyl, tetrahydropyranyl, tetrahydrothiophenyl, piperazinyl, and the like.

The term "alkoxy" refers to straight or branched chain alkoxides of the number of carbon atoms specified (e.g., $C_{1-4}$ alkoxy), or any number within this range [i.e., methoxy (MeO—), ethoxy, isopropoxy, etc.].

The term "alkylthio" refers to straight or branched chain alkylsulfides of the number of carbon atoms specified (e.g., $C_{1-4}$ alkylthio), or any number within this range [i.e., methylthio (MeS—), ethylthio, isopropylthio, etc.].

The term "alkylamino" refers to straight or branched alkylamines of the number of carbon atoms specified (e.g., $C_{1-4}$ alkylamino), or any number within this range [i.e., methylamino, ethylamino, isopropylamino, t-butylamino, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl ($MeSO_2$—), ethylsulfonyl, isopropylsulfonyl, etc.].

The term "alkyloxycarbonyl" refers to straight or branched chain esters of a carboxylic acid derivative of the present invention of the number of carbon atoms specified (e.g., $C_{1-4}$ alkyloxycarbonyl), or any number within this range [i.e., methyloxycarbonyl (MeOCO—), ethyloxycarbonyl, or butyloxycarbonyl].

The term "aryl" includes both phenyl, naphthyl, and pyridyl. The aryl group is optionally substituted with one to three groups independently selected from $C_{1-4}$ alkyl, halogen, cyano, nitro, trifluoromethyl, $C_{1-4}$ alkoxy, and $C_{1-4}$ alkylthio.

The term "halogen" is intended to include the halogen atoms fluorine, chlorine, bromine and iodine.

The term "phosphoryl" refers to —$P(O)(OH)_2$.

The term "diphosphoryl" refers to the radical having the structure:

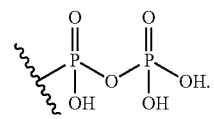

The term "triphosphoryl" refers to the radical having the structure:

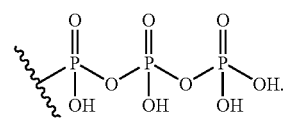

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally.

When $R^9$ in the amino acyl residue embodiment of $R^2$, $R^3$, and $R^5$ is other than hydrogen in the formula

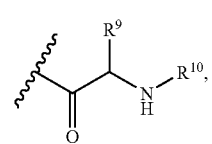

the amino acyl residue contains an asymmetric center and is intended to include the individual R— and S— stereoisomers as well as RS-diastereoisomeric mixtures.

The term "5'-triphosphate" refers to a triphosphoric acid ester derivative of the 5'-hydroxyl group of a C-nucleoside compound of the present invention having the following general structural formula II:

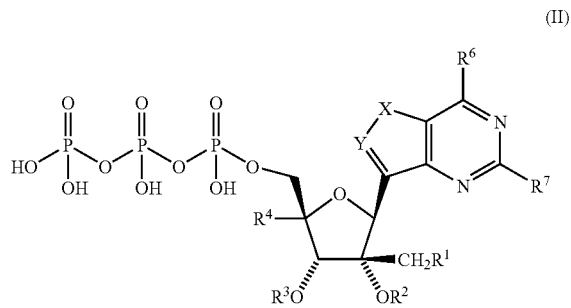

(II)

wherein X, Y, $R^1$-$R^4$, $R^6$ and $R^7$ are as defined above. The compounds of the present invention are also intended to include pharmaceutically acceptable salts of the triphosphate ester as well as pharmaceutically acceptable salts of 5'-monophosphate and 5'-diphosphate ester derivatives of the structural formulae III and IV, respectively,

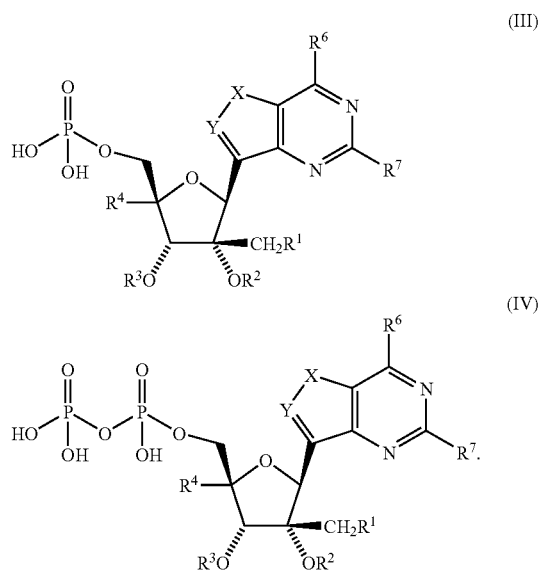

(III)

(IV)

The term "composition", as in "pharmaceutical composition," is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The terms "administration of" and "administering a" compound should be understood to mean providing a compound of the invention or a prodrug of a compound of the invention to the individual in need.

Another aspect of the present invention is concerned with a method of inhibiting HCV NS5B polymerase, inhibiting HCV replication, or treating HCV infection with a compound of the present invention in combination with one or more agents useful for treating HCV infection. Such agents active against HCV include, but are not limited to, ribavirin, levovirin, viramidine, thymosin alpha-1, interferon-β, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a (such as Roferon interferon available from Hoffmann-LaRoche, Nutley, N.J.), pegylated interferon-α2a (Pegasys™), interferon-α2b (such as Intron-A interferon available from Schering Corp., Kenilworth, N.J.), pegylated interferon-α2b (PegIntron™), a recombinant consensus interferon (such as interferon alphacon-1), and a purified interferon-α product. Amgen's recombinant consensus interferon has the brand name Infergen®. Levovirin is the L-enantiomer of ribavirin which has shown immunomodulatory activity similar to ribavirin. Viramidine represents an analog of ribavirin disclosed in WO 01/60379 (assigned to ICN Pharmaceuticals). In accordance with this method of the present invention, the individual components of the combination can be administered separately at different times during the course of therapy or concurrently in divided or single combination forms. The instant invention is therefore to be understood as embracing all such regimes of simultaneous or alternating treatment, and the term "administering" is to be interpreted accordingly. It will be understood that the scope of combinations of the compounds of this invention with other agents useful for treating HCV infection includes in principle any combination with any pharmaceutical composition for treating HCV infection. When a compound of the present invention or a pharmaceutically acceptable salt thereof is used in combination with a second therapeutic agent active against HCV, the dose of each compound may be either the same as or different from the dose when the compound is used alone.

For the treatment of HCV infection, the compounds of the present invention may also be administered in combination with an agent that is an inhibitor of HCV NS3 serine protease. HCV NS3 serine protease is an essential viral enzyme and has been described to be an excellent target for inhibition of HCV replication. Both substrate and non-substrate based inhibitors of HCV NS3 protease inhibitors are disclosed in WO 98/22496, WO 98/46630, WO 99/07733, WO 99/07734, WO 99/38888, WO 99/50230, WO 99/64442, WO 00/09543, WO 00/59929, GB-2337262, WO 02/48116, WO 02/48172, and U.S. Pat. No. 6,323,180. HCV NS3 protease as a target for the development of inhibitors of HCV replication and for the treatment of HCV infection is discussed in B. W. Dymock, "Emerging therapies for hepatitis C virus infection," *Emerging Drugs*, 6: 1342 (2001).

Ribavirin, levovirin, and viramidine may exert their anti-HCV effects by modulating intracellular pools of guanine nucleotides via inhibition of the intracellular enzyme inosine monophosphate dehydrogenase (IMPDH). IMPDH is the rate-limiting enzyme on the biosynthetic route in de novo guanine nucleotide biosynthesis. Ribavirin is readily phosphorylated intracellularly and the monophosphate derivative is an inhibitor of IMPDH. Thus, inhibition of IMPDH represents another useful target for the discovery of inhibitors of HCV replication. Therefore, the compounds of the present invention may also be administered in combination with an inhibitor of IMPDH, such as VX-497, which is disclosed in WO 97/41211 and WO 01/00622 (assigned to Vertex); another IMPDH inhibitor, such as that disclosed in WO 00/25780 (assigned to Bristol-Myers Squibb); or mycophenolate mofetil [see A. C. Allison and E. M. Eugui, *Agents Action*, 44 (Suppl.): 165 (1993)].

For the treatment of HCV infection, the compounds of the present invention may also be administered in combination with the antiviral agent amantadine (1-aminoadamantane) [for a comprehensive description of this agent, see J. Kirschbaum, *Anal. Profiles Drug Subs.* 12: 1-36 (1983)].

The compounds of the present invention may also be combined for the treatment of HCV infection with antiviral 2'-C-branched ribonucleosides disclosed in R. E. Harry-O'kuru, et al., *J. Org. Chem.* 62: 1754-1759 (1997); M. S. Wolfe, et al., *Tetrahedron Lett.*, 36: 7611-7614 (1995); U.S. Pat. No. 3,480, 613 (Nov. 25, 1969); International Publication Number WO 01/90121 (29 Nov. 2001); International Publication Number WO 01/92282 (6 Dec. 2001); and International Publication Number WO 02/32920 (25 Apr. 2002); and International Publication Number WO 04/002999 (8 Jan. 2004); and International Publication Number WO 04/003000 (8 Jan. 2004); and International Publication Number WO 04/002422 (8 Jan. 2004); the contents of each of which are incorporated by reference in their entirety. Such 2'-C-branched ribonucleosides include, but are not limited to, 2'-C-methyl-cytidine, 2'-C-methyl-uridine, 2'-C-methyl-adenosine, 2'-C-methyl-guanosine, and 9-(2-C-methyl-β-D-ribofuranosyl)-2,6-diaminopurine, and the corresponding amino acid ester of the ribose C-2', C-3', and C-5'hydroxyls and the corresponding optionally substituted cyclic 1,3-propanediol esters of the 5'-phosphate derivatives.

The compounds of the present invention may also be combined for the treatment of HCV infection with other nucleosides having anti-HCV properties, such as those disclosed in WO 02/51425 (4 Jul. 2002), assigned to Mitsubishi Pharma Corp.; WO 01/79246, WO 02/32920, and WO 02/48165 (20 Jun. 2002), assigned to Pharmasset, Ltd.; WO 01/68663 (20 Sep. 2001), assigned to ICN Pharmaceuticals; WO 99/43691 (2 Sep. 1999); WO 02/18404 (7 Mar. 2002), assigned to Hoffmann-LaRoche; U.S. 2002/0019363 (14 Feb. 2002); WO 02/100415 (19 Dec. 2002); WO 03/026589 (3 Apr. 2003); WO 03/026675 (3 Apr. 2003); WO 03/093290 (13 Nov. 2003): US 2003/0236216 (25 Dec. 2003); US 2004/0006007 (8 Jan. 2004); WO 04/011478 (5 Feb. 2004); WO 04/013300 (12 Feb. 2004); US 2004/0063658 (1 Apr. 2004); and WO 04/028481 (8 Apr. 2004).

The compounds of the present invention may also be combined for the treatment of HCV infection with non-nucleoside inhibitors of HCV polymerase such as those disclosed in WO 01/77091 (18 Oct. 2001), assigned to Tularik, Inc.; WO 01/47883 (5 Jul. 2001), assigned to Japan Tobacco, Inc.; WO 02/04425 (17 Jan. 2002), assigned to Boehringer Ingelheim; WO 02/06246 (24 Jan. 2002), assigned to Istituto di Ricerche di Biologia Moleculare P. Angeletti S. P. A.; and WO 02/20497 (3 Mar. 2002).

By "pharmaceutically acceptable" is meant that the carrier, diluent, or excipient must be compatible with the other ingredients of the formulation and not deleterious to the recipient thereof.

Also included within the present invention are pharmaceutical compositions comprising the C-nucleoside compounds and derivatives thereof of the present invention in association with a pharmaceutically acceptable carrier. Another example of the invention is a pharmaceutical composition made by combining any of the compounds described above and a pharmaceutically acceptable carrier. Another illustration of the invention is a process for making a pharmaceutical composition comprising combining any of the compounds described above and a pharmaceutically acceptable carrier.

Also included within the present invention are pharmaceutical compositions useful for inhibiting RNA-dependent RNA viral polymerase in particular HCV NS5B polymerase comprising an effective amount of a compound of the present invention and a pharmaceutically acceptable carrier. Pharmaceutical compositions useful for treating RNA-dependent RNA viral infection in particular HCV infection are also encompassed by the present invention as well as a method of inhibiting RNA-dependent RNA viral polymerase in particular HCV NS5B polymerase and a method of treating RNA-dependent viral replication and in particular HCV replication. Additionally, the present invention is directed to a pharmaceutical composition comprising a therapeutically effective amount of a compound of the present invention in combination with a therapeutically effective amount of another agent active against RNA-dependent RNA virus and in particular against HCV. Agents active against HCV include, but are not limited to, ribavirin, levovirin, viramidine, thymosin alpha-1, an inhibitor of HCV NS3 serine protease, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a (such as Roferon interferon available from Hoffmann-LaRoche, Nutley, N.J.), interferon-α2b (such as Intron-A interferon available from Schering Corp., Kenilworth, N.J.), a consensus interferon, and a purified interferon-α product. For a discussion of ribavirin and its activity against HCV, see J. O. Saunders and S. A. Raybuck, "Inosine Monophosphate Dehydrogenase: Consideration of Structure, Kinetics, and Therapeutic Potential," *Ann. Rep. Med. Chem.*, 35: 201-210 (2000).

Another aspect of the present invention provides for the use of the C-nucleoside compounds and derivatives thereof and their pharmaceutical compositions for the manufacture of a medicament for the inhibition of RNA-dependent RNA viral replication, in particular HCV replication, and/or the treatment of RNA-dependent RNA viral infection, in particular HCV infection. Yet a further aspect of the present invention provides for the C-nucleoside compounds and derivatives thereof and their pharmaceutical compositions for use as a medicament for the inhibition of RNA-dependent RNA viral replication, in particular HCV replication, and/or for the treatment of RNA-dependent RNA viral infection, in particular HCV infection.

The pharmaceutical compositions of the present invention comprise a compound of structural formula I as an active ingredient or a pharmaceutically acceptable salt thereof, and may also contain a pharmaceutically acceptable carrier and optionally other therapeutic ingredients.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of structural formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of structural formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of structural formula I are administered orally.

For oral administration to humans, the dosage range is 0.01 to 1000 mg/kg body weight in divided doses. In one embodiment the dosage range is 0.1 to 100 mg/kg body weight in divided doses. In another embodiment the dosage range is 0.5 to 20 mg/kg body weight in divided doses. For oral administration, the compositions are preferably provided in the form of tablets or capsules containing 1.0 to 1000 milligrams of the active ingredient, particularly, 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated.

The effective dosage of active ingredient employed may vary depending on the particular compound employed, the mode of administration, the condition being treated and the severity of the condition being treated. Such dosage may be ascertained readily by a person skilled in the art. This dosage regimen may be adjusted to provide the optimal therapeutic response.

The compounds of the present invention contain one or more asymmetric centers and can thus occur as racemates and racemic mixtures, single enantiomers, diastereomeric mixtures and individual diastereomers. The present invention is meant to comprehend C-nucleoside compounds having the β-D stereochemical configuration for the five-membered furanose ring as depicted in the structural formula below, that is, C-nucleoside compounds in which the substituents at C-1 and C-4 of the five-membered furanose ring have the β-stereochemical configuration ("up" orientation as denoted by a bold line).

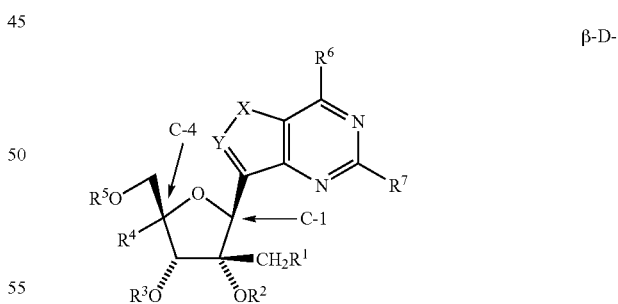

Some of the compounds described herein contain olefinic double bonds, and unless specified otherwise, are meant to include both E and Z geometric isomers.

Some of the compounds described herein may exist as tautomers such as keto-enol tautomers. The individual tautomers as well as mixtures thereof are encompassed with compounds of structural formula I. Example of keto-enol tautomers which are intended to be encompassed within the compounds of the present invention are illustrated below:

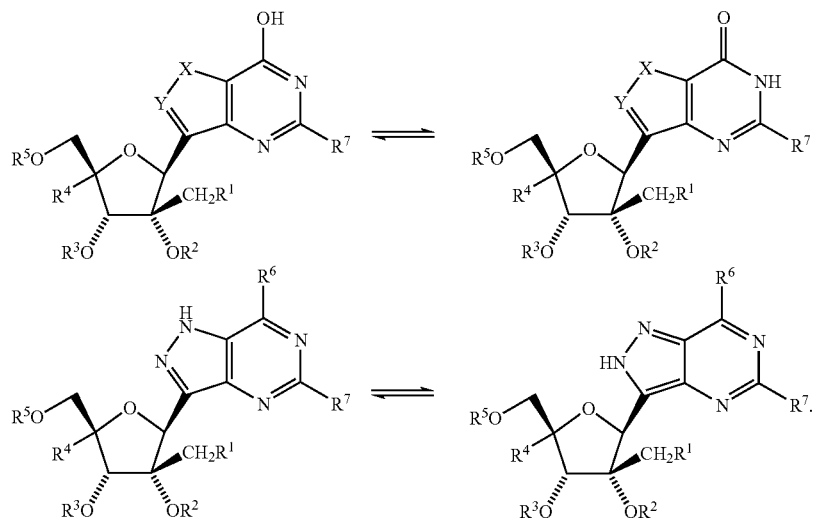

Compounds of structural formula I may be separated into their individual diastereoisomers by, for example, fractional crystallization from a suitable solvent, for example methanol or ethyl acetate or a mixture thereof, or via chiral chromatography using an optically active stationary phase.

Alternatively, any stereoisomer of a compound of the structural formula I may be obtained by stereospecific synthesis using optically pure starting materials or reagents of known configuration.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH), phosphoric acid [—OP(O)(OH)$_2$], or alcohol group being present in the compounds of the present invention, pharmaceutically acceptable prodrug esters of carboxylic acid derivatives, such as methyl, ethyl, or pivaloyloxymethyl esters; pharmaceutically acceptable prodrug esters of 5'-phosphoric acid derivatives (including 5'-monophosphate, 5'-diphosphate, and 5'-triphosphate) of the C-nucleosides; or prodrug acyl derivatives of the ribose C-2', C-3', and C-5' hydroxyls, such as O-acetate and O-maleate, can be employed. Included are those esters and acyl groups known in the art for modifying the bioavailability, tissue distribution, solubility, and hydrolysis characteristics for use as sustained-release or prodrug formulations. The contemplated derivatives are readily convertible in vivo into the required compound. Thus, in the methods of treatment of the present invention, the terms "administering" and "administration" is meant to encompass the treatment of the viral infections described with a compound specifically disclosed or with a compound which may not be specifically disclosed, but which converts to the specified compound in vivo after administration to the mammal, including a human patient. Conventional procedures for the selection and preparation of suitable prodrug derivatives are described, for example, in "Design of Prodrugs," ed. H. Bundgaard, Elsevier, 1985, which is incorporated by reference herein in its entirety.

Preparation of the C-Nucleoside Compounds and Derivatives of the Invention:

The C-nucleoside compounds and derivatives thereof of the present invention can be prepared applying synthetic methodologies well-established in the practice of nucleoside and nucleotide chemistry as well as variations thereof.

The preparation of C-nucleosides having a 7-amino-1H-pyrazolo[4,3-d]pyrimidin-3-yl nucleobase at the C-1 position of the 2-C-Me-ribofuranose ring can be accomplished as depicted in Schemes 1 and 2 and detailed in the description below.

SCHEME 1

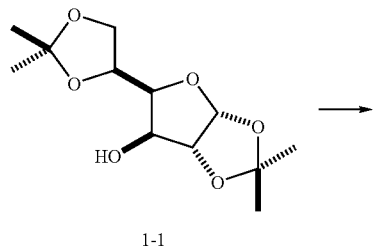

1-1

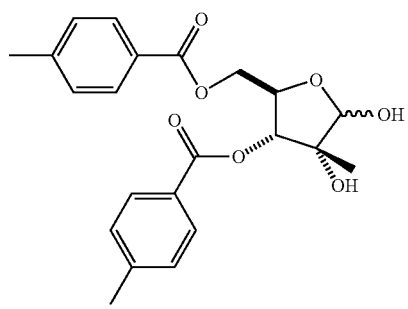

1-2

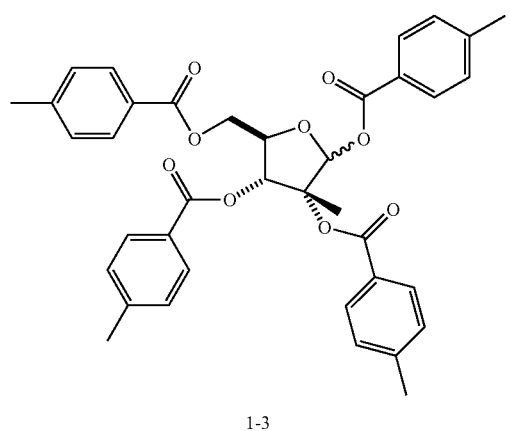

1-3

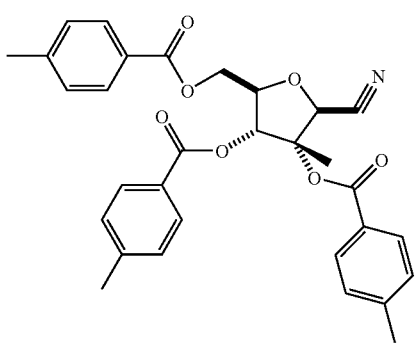

1-4

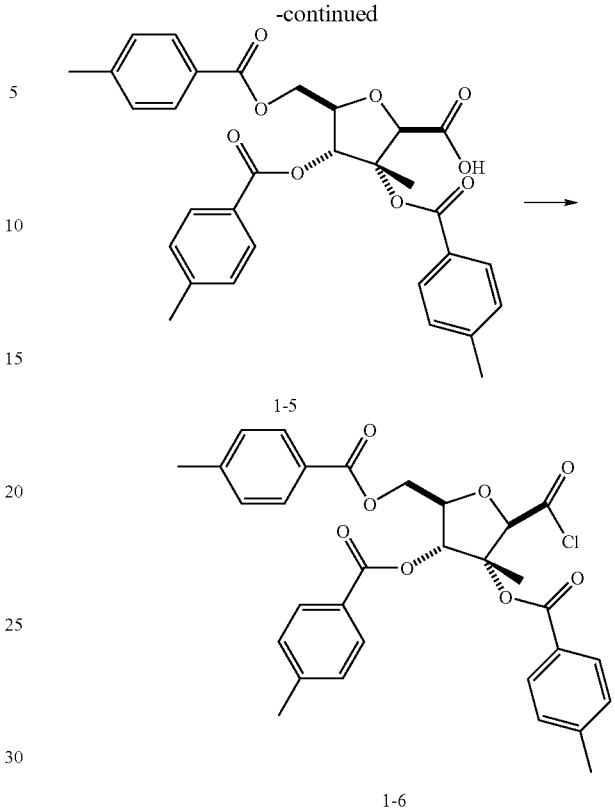

1-5

1-6

Diacetone glucose 1-1 can be converted into 3,5-di-O-(p-toluoyl)-2-C-methyl-D-ribofuranose 1-2 following the procedures described by M. Bio et al. in "Practical Synthesis of a Potent Hepatitis Virus C Polymerase Inhibitor," J. Org. Chem., 69: 6257-6266 (2004). The C-1 and C-2 hydroxyls present in diol 1-2 are protected as their p-toluoyl ester derivatives. However, other protecting groups, such as a different ester, an ether, and a silyl ether can also be employed. In the subsequent step, a cyano group can be attached at the anomeric C-1 position of the furanose ring providing the foundation of the nucleobase framework. This can be accomplished by a procedure which incorporates the cyano group in a β-stereochemical orientation. Alternatively, the isomer with the proper steric orientation can be separated from a mixture using chromatographic or other suitable methods. This can be achieved by reacting a cyanide source, such as trimethylsilyl cyanide, with the tetraester 1-3 in the presence of a Lewis acid, for example, boron trifluoride, tin tetrachloride, and titanium tetrachloride, at ambient, elevated or reduced temperature, optionally in the presence of a solvent, such as a halogenated hydrocarbon, such as dichloromethane, 1,2-dichloroethane, and chloroform. Examples of such transformations can be found in Utimoto et al., Tetrahedron, 39: 967 (1983).

In the subsequent step, the cyano group can be hydrolyzed to the corresponding acid 1-5 directly or via the intermediate amide. The desired transformation can be accomplished using an acid-catalyzed hydrolysis in the presence of a limited amount of water at mildly elevated temperatures. In the next step, the acid 1-5 can be converted into the corresponding acyl chloride 1-6 using standard conditions, such as by treatment of a solution of acid 1-5 with oxalyl chloride in the presence of a catalytic amount of N,N-dimethylformamide (DMF) in a suitable solvent, such as dichloromethane and tetrahydrofuran.

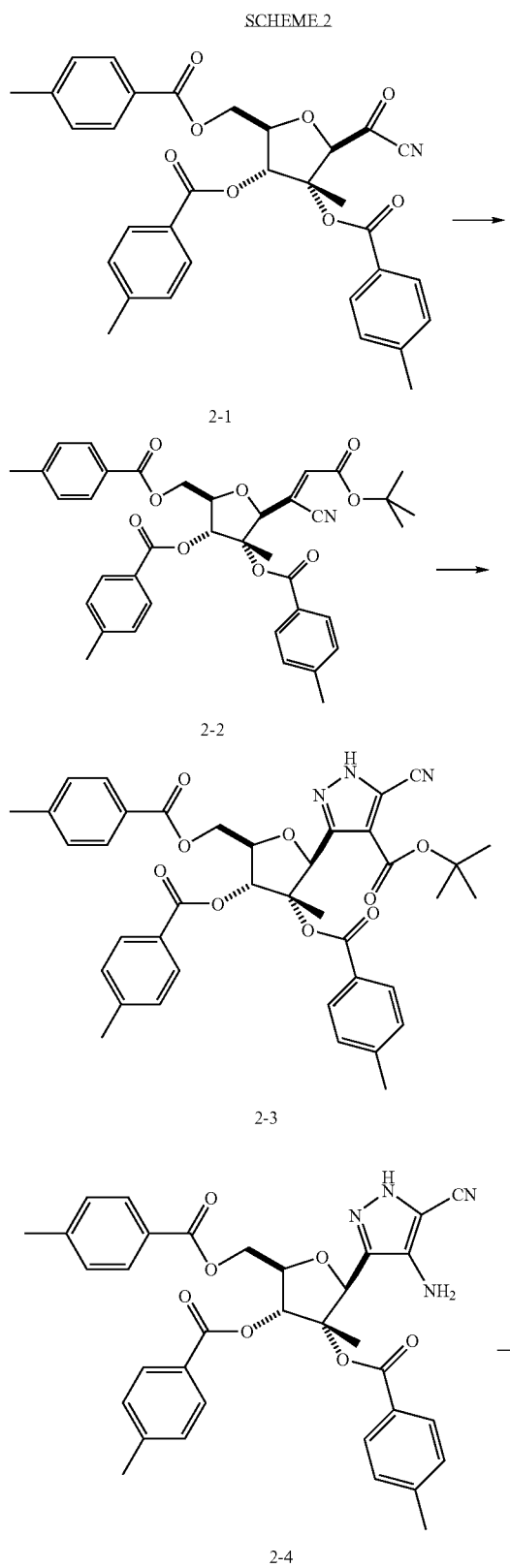

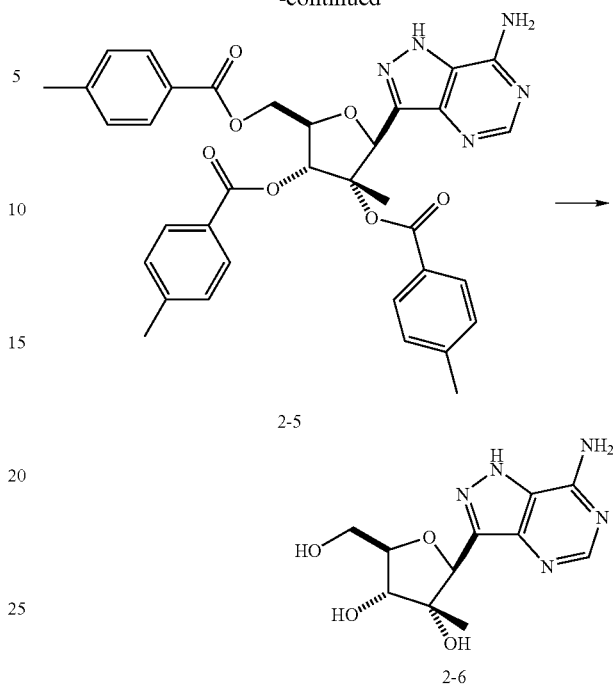

The construction of the 7-amino-1H-pyrazolo[4,3-d]pyrimidine ring system can be accomplished as depicted in Scheme 2 via the α-ketonitrile 2-1. Such transformations are well-known in the scientific literature; for example, see Herrman, K. and Simchen, G., *Synthesis* 204 (1979) or Rosowski, A., Ghoshal, M., Solan, V. C., *Carbohyd. Res.*, 176: 47-58 (1988). The α-ketonitrile 2-1 can be reacted with a Wittig reagent, such as tert-butoxycarbonylmethylenetriphenylphosphorane, under standard reaction conditions [Wittig, G., Schollkopf, U., *Chem. Ber.*, 87: 1318 (1954)] to afford the ester nitrite 2-2. An analogous transformation has been described by L. Kalvoda in *Coll. Czech. Chem. Comm.*, 43: 1431-1437 (1978) as part of a synthesis of formycin. The subsequent steps are similar to those described in the Kalvoda publication. A dipolar cycloaddition of diazoacetonitrile and the unsaturated ester 2-2 furnishes, after elimination of hydrogen cyanide, the pyrazole ring system in 24. Alternative diazoacetates can be used, but it is advantageous to choose esters which allow for selective manipulations of the ester groups present in structures, such as 2-3. In the next step, the tert-butyl ester group can be cleaved under standard acidic conditions, such as those found in Greene, T. W., Wuts, P. G. M., "Protective Groups in Organic Synthesis," John Wiley & Sons, Inc., 3$^{rd}$ Edition, 1999. The liberated acid can then be subjected to a Curtius rearrangement [Curtius, T., *Chem. Ber.*, 23: 3023 (1890)]. A number of conditions are suitable for the formation of the intermediate azide, and reagents such as diphenylphosphoryl azide [Milari, B. L., Beyer, T. A., Siegel, T. W., *J. Med. Chem.*, 34: 1011 (1991)] can be employed. The isocyanate can be converted into the desired amine 2-4, or a urethane intermediate can be formed with an alcohol. The urethane, however, must be hydrolyzed to afford the desired amine. The completion of the heterocylic ring construction can be accomplished by reacting the aminonitrile 2-4 with formamidine acetate in a suitable solvent, such as ethanol. An example of an analogous transformation can be found in the published synthesis of formycin by Buchanan, J. G., Smith, D. and Wightman, R. H. in *Tetrahedron,* 40: 119-123 (1984). The desired C-nucleoside 2-6 can be obtained by solvolytic cleavage of the ester protecting groups, which can be accomplished by a number of methods found in Greene, T. W., Wuts, P. G. M., "Protective Groups in Organic Synthesis", John Wiley & Sons, Inc., 3$^{rd}$ Edition, 1999. Particularly suitable for the ester cleavage step are basic conditions, such as exposure of the tri-ester 2-5 to a methanolic solution of sodium methoxide.

The preparation of the C-nucleosides having a 4-aminofuro[3,2-d]pyrimidin-7-yl nucleobase at the C-1 position of the 2-C-Me-ribofuranose ring can be accomplished as depicted in Schemes 3, 4A, and 4B and detailed in the description below.

SCHEME 3

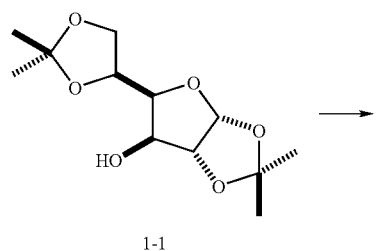

1-1

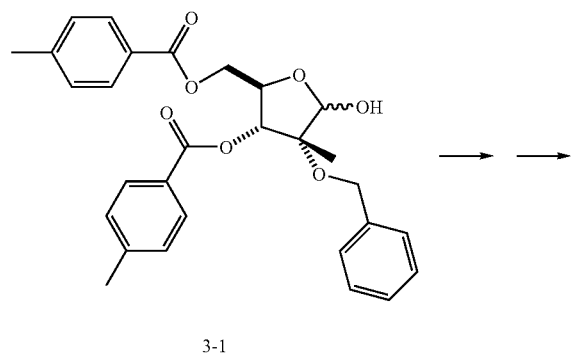

3-1

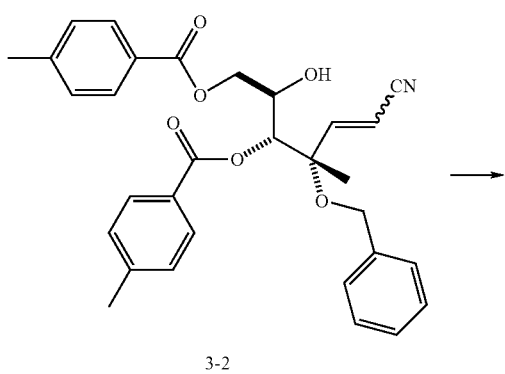

3-2

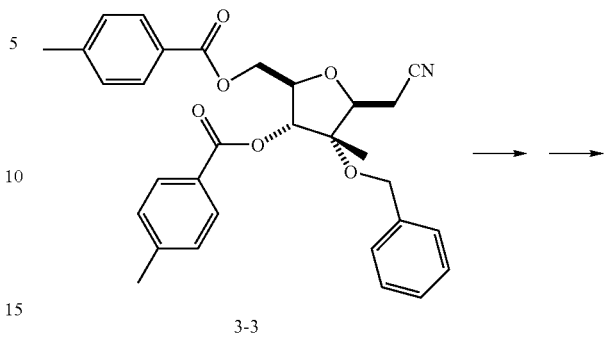

3-3

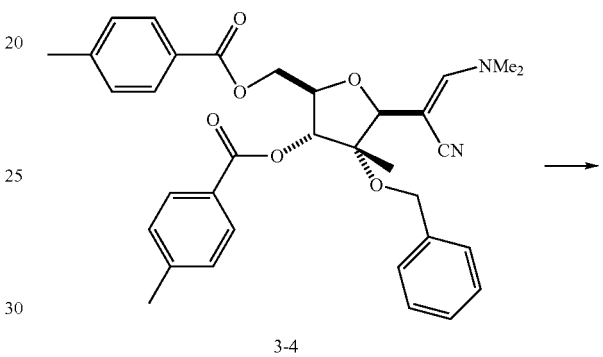

3-4

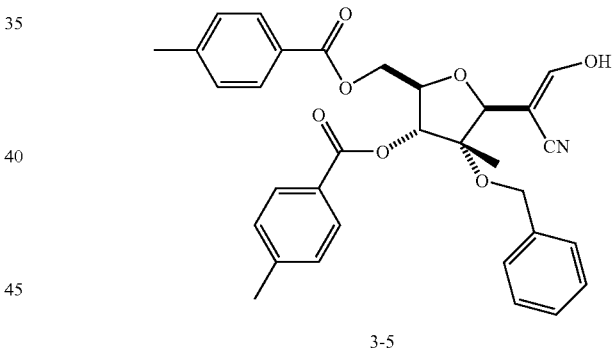

3-5

The starting material is diacetone glucose 1-1 which is converted into benzyl ether 3-1 as described by M. Bio, et al., "Practical Synthesis of a Potent Hepatitis Virus C Polymerase Inhibitor," *J. Org. Chem.,* 69: 6257-6266 (2004). This lactol 3-1 is then subjected to a Homer-modification of the Wittig reaction using diethyl cyanomethylphosphonate [Wadsworth, W. S., Emmons, W. D., *J. Am. Chem. Soc.,* 83: 1733 (1961)]. The initial product 3-2 spontaneously closes to afford a mixture of α- and β-isomers, from which the desired β-isomer 3-3 is isolated using chromatographic methods. When nitrile 3-3 is exposed to bis(dimethylamino)tertbutoxymethane in a suitable solvent, such as N,N-dimethylformamide, a condensation takes place similar to that described by Liang, C., et al. in *Carbohyd. Res.,* 303: 33-38 (1997). A controlled hydrolysis of the enamine product 34, similar to that described by Battacharya, B. E., et al., in *Tetrahedron Lett.,* 27: 815-818 (1986), affords the enol nitrile 3-5.

SCHEME 4A

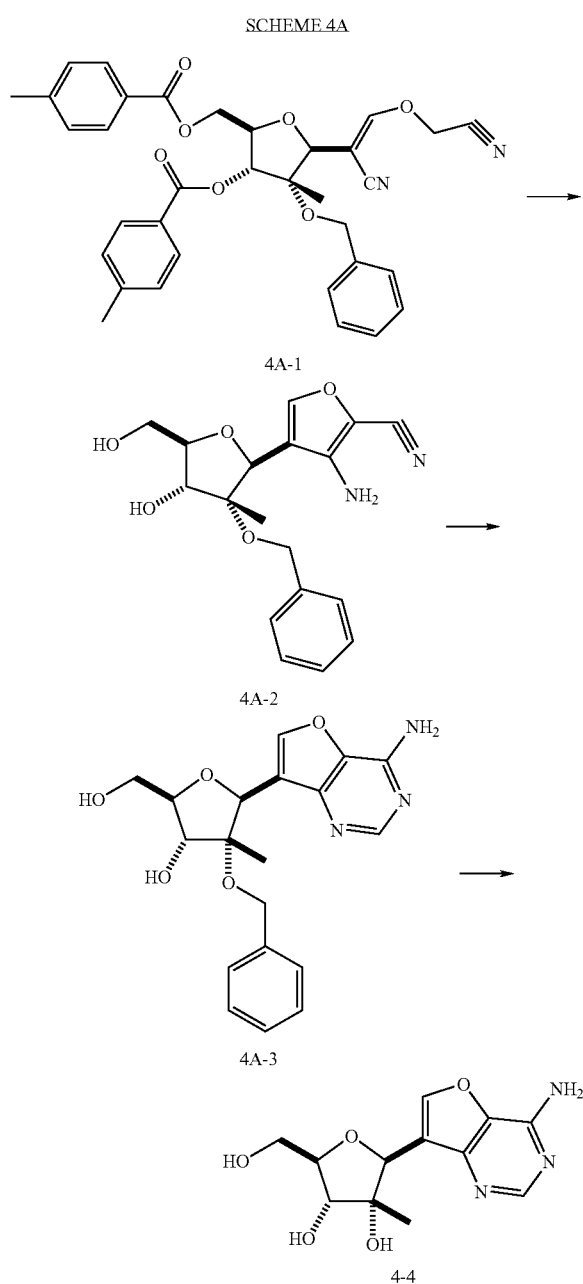

Alkylation of enolate 3-5 with chloroacetonitrile affords the ether 4A-1. Exposure of this nitrile to a strong base, such as lithium N,N-diisopropylamide and sodium ethoxide, results in the formation of an intermediate carbanion followed by ring closure, as shown in Scheme 4A. An example of a similar closure can be found in *Tetrahedron Lett.*, 27: 815-818 (1986). Under these conditions, the ester protecting groups are also cleaved affording aminonitrile 4A-2. Aminonitrile 4A-2 is then converted to the furo[3,2-d]pyrimidine ring system in a similar manner as described above for the elaboration of 2-4. Removal of the benzyl group under hydrogenolytic conditions yields the desired final compound 4-4.

Alternatively, compound 4-4 can be also prepared following a procedure depicted in Scheme 4B. According to this modification, the diol 4B-8 is subjected to a Horner-modification of the Wittig reaction using diethyl cyanomethylphosphonate [Wadsworth, W. S., Emmons, W. D., *J. Am. Chem. Soc.*, 83: 1733 (1961)], as described above. Under these conditions, the predominant α-isomer is acylated with p-toluoyl chloride to yield the triester 4B-2. This intermediate is then subjected to a series of steps analogous to those described in Schemes 3 and 4 leading eventually to intermediate 4B-6. The last step in this sequence requires the use of a strong base, which induces an epimerization at C-1 of the ribofuranose ring. The desired isomer 4B-6 is separated from a mixture of isomers by suitable chromatographic methods. The synthesis of the heterocyclic nucleobase and removal of the ester protecting groups are accomplished as described in the Kalvoda publication [*Coll. Czech. Chem. Comm.*, 43: 1431-1437 (1977)].

Scheme 4B

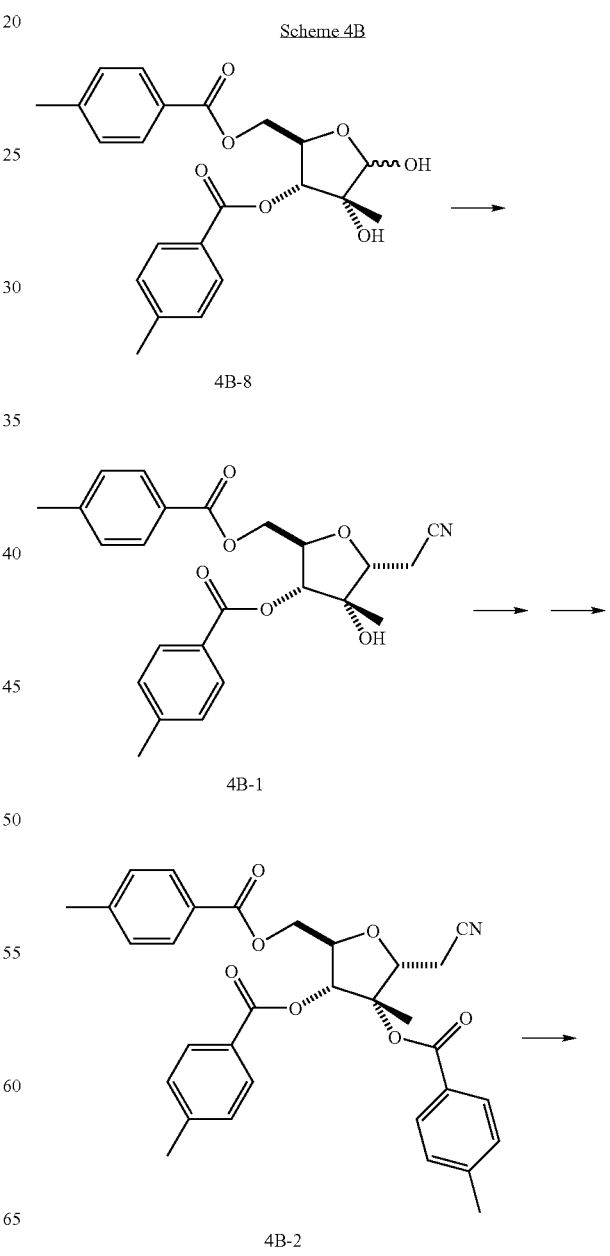

-continued

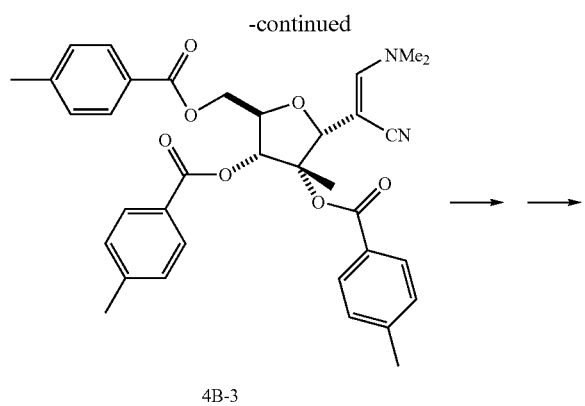

4B-3

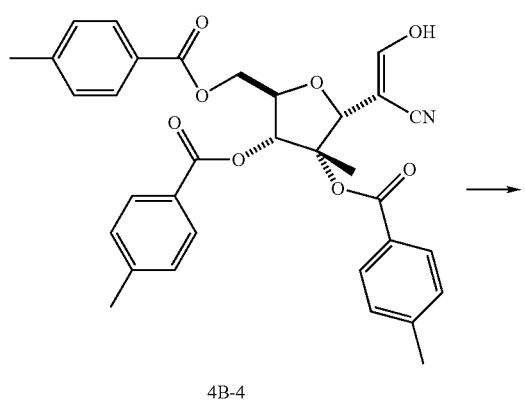

4B-4

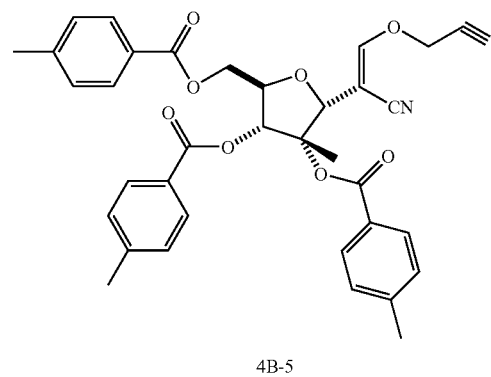

4B-5

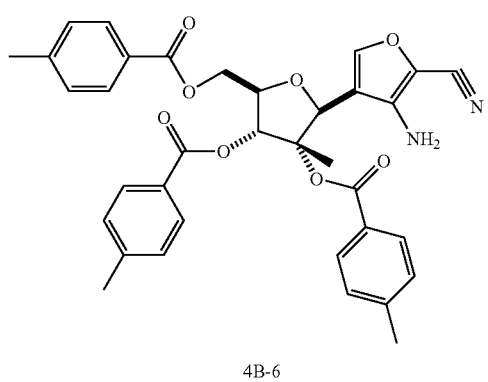

4B-6

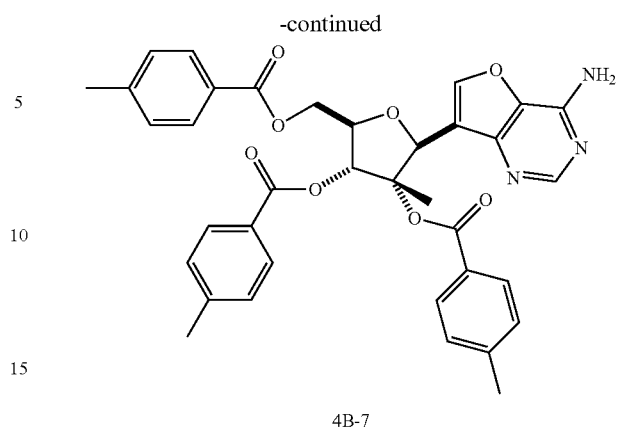

4B-7

Alternatively, the C-nucleoside having a 4-aminofuro[3,2-d]pyrimidin-7-yl nucleobase at the C-1 position of the 2-C-Me-ribofuranose ring (4-4) can be also accomplished as depicted in Schemes 4C, 4D and 4E detailed in the description below. According to this variant of the synthesis, an acid-labile set of protecting groups is introduced first. This transformation can be performed following the synthetic steps depicted in Scheme 4C.

Scheme 4C

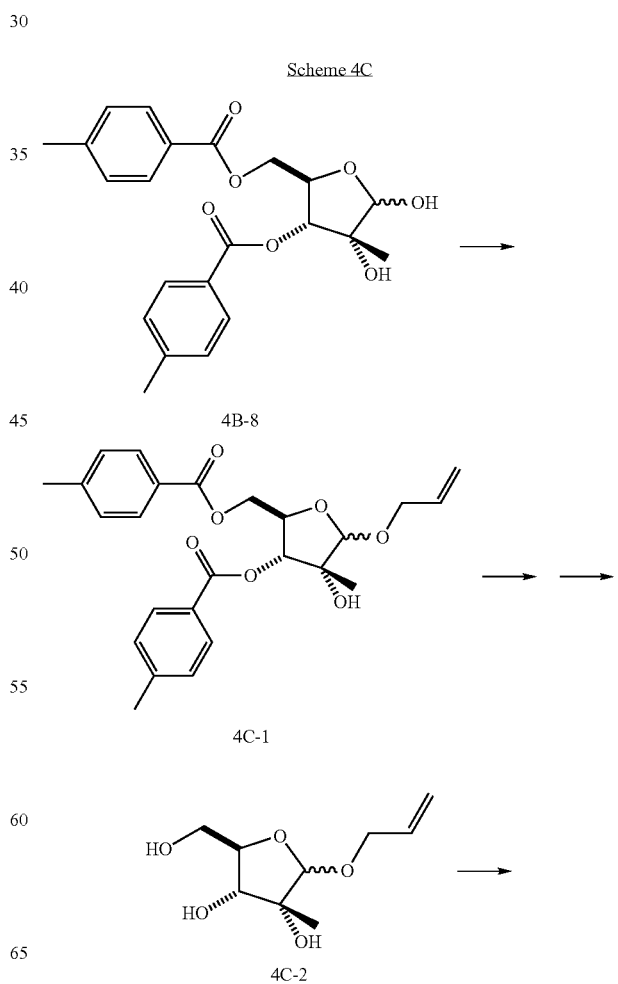

-continued

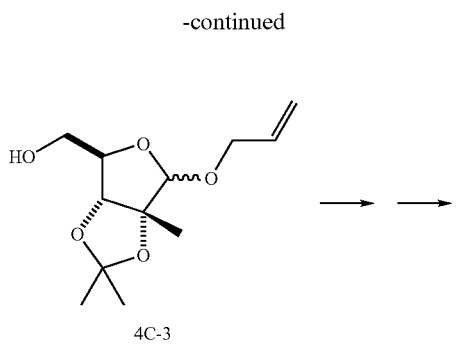
4C-3

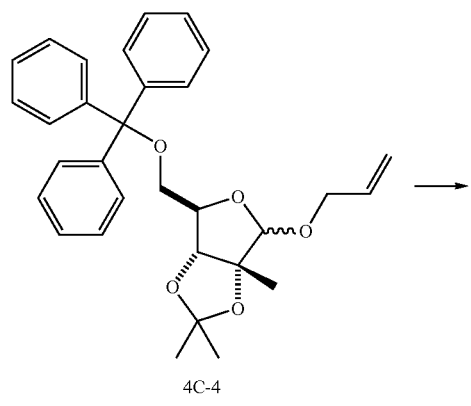
4C-4

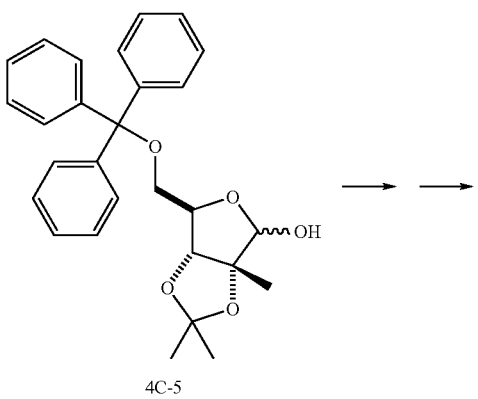
4C-5

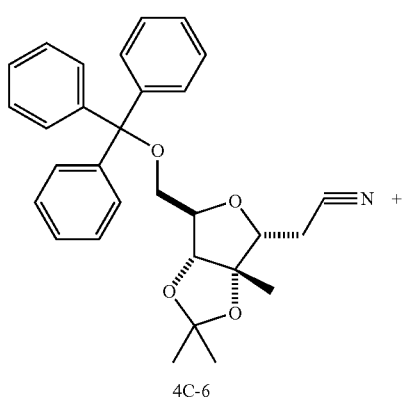
4C-6

-continued

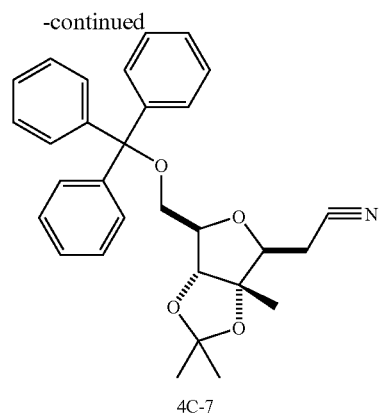
4C-7

In order to facilitate further transformations, it is advantageous to protect the C-1 hydroxyl of intermediate 4B-8. A number of protecting groups can be considered (see Greene, T. W., Wuts, P. G. M., "Protective Groups in Organic Synthesis", John Wiley & Sons, Inc., $3^{rd}$ Edition, 1999) and the C-1 O-allyl ether is particularly attractive since it is stable under both acidic and basic conditions. It can be readily introduced by reacting 4B-8 with allyl alcohol. This reaction can be performed with or without a solvent, at ambient or elevated temperature. Usually, an acidic catalyst is employed to facilitate the acetal formation. In this case, a facile preparation of compound 4C-1 can be accomplished using allyl alcohol as a solvent and pyridinium p-toluenesulfonate as catalyst at elevated temperatures. The toluoyl protecting groups for the C-3 and C-5 hydroxyls can be removed at this time by means of base-catalyzed transesterification with methanol to afford compound 4C-2. The introduction of the base-robust protecting groups can be accomplished by protecting the C-2 and C-3 hydroxyls first. Once again a number of options is available, but five-membered cyclic acetals are particularly advantageous. Thus, compound 4C-3 can be obtained by reacting 2,2-dimethoxypropane with the triol 4C-2. This reaction can be performed with or without a solvent, under acid catalysis, such as p-toluenesulfonic acid. The primary hydroxyl at position C-5 can be protected with a number of base-robust protecting groups, such as aryl (or alkyl)silyl-, (substituted)trityl- or other suitable groups. The use of an unsubstituted trityl protecting group is particularly advantageous, and it can be introduced, for example, by reaction of 4C-3 with trityl chloride in pyridine as solvent. At this point the C-1 allyl group can be removed, and a number of conditions are available. The double bond contained within the allyl group can be isomerized with base, and the resulting enol-ether then hydrolyzed under neutral conditions. Such procedures are well known in the literature, and an overview by F. Guibe is presented in *Tetrahedron*, 53: 13509-13557 (1997). However, a particularly attractive approach is that described by T. Taniguchi and K. Ogarasawa in *Angew. Chem. Int. Ed.*, 110: 1137-1139 (1998). Following this procedure, the allyl group can be removed efficiently using nickel (II) chloride and DIBAL-H at 0° C. using diethyl ether as solvent. A two-carbon chain in the form of a cyanomethylene group can be attached at this point. The two carbons are eventually elaborated to carbons 4 and 9 of the complete C-nucleoside, and this transformation can be accomplished by using the above-mentioned Homer-Emmons reaction. As this reaction proceeds through the open (aldehyde) form of the sugar, a spontaneous ring closure yields the desired C-1 cyanomethyl sugar. This ring closure will cause the absolute stereochemistry at C-1 to scramble, and as a result of this, two C-1 epimers 4C-6 and 4C-7 are formed. If desired, these can be separated by various column chromatography methods, however, further manipulations of this intermediate will cause epimerization at this center. It is therefore advantageous to proceed with the reaction sequence without separation of isomers.

The construction of the furan ring can be accomplished by a variation of the Kirsch reaction [G. Kirsch et al., *J. Heterocyclic Chem.*, 19: 443 (1982)]. A Claisen condensation between the epimeric mixture 4C-6 and 4C-7 and methyl formate can be used to introduce the hydroxymethylene functionality at the α-carbon relative to the nitrile group. However, alternative procedures to accomplish this transformation are also known [for example, see De Bernado, S., Weigele, M., *J. Org. Chem.*, 42: 109 (1977)].

Scheme 4D

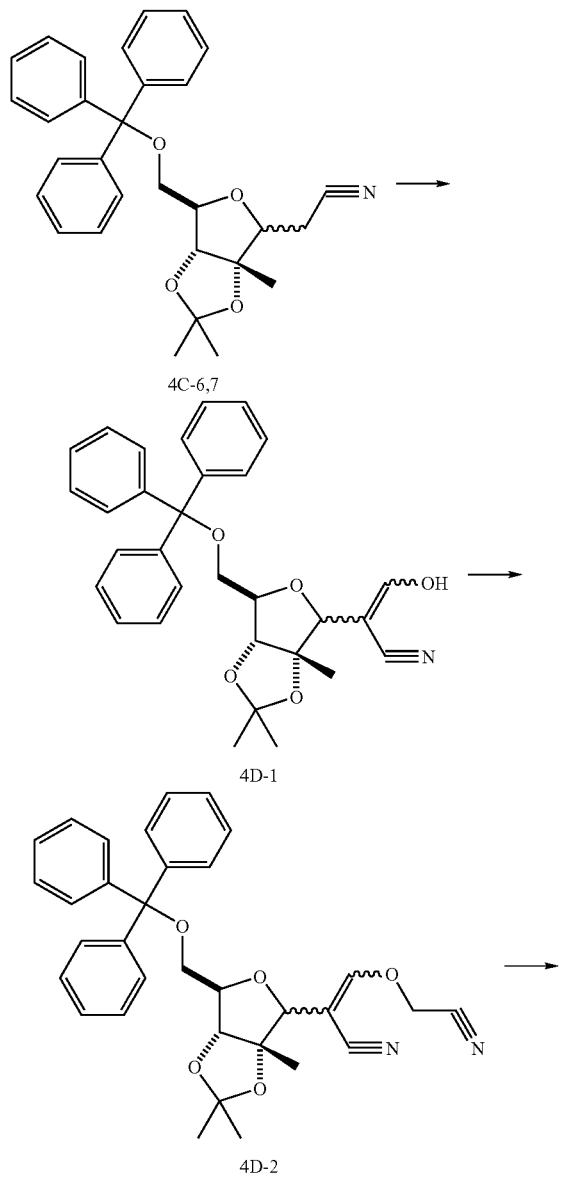

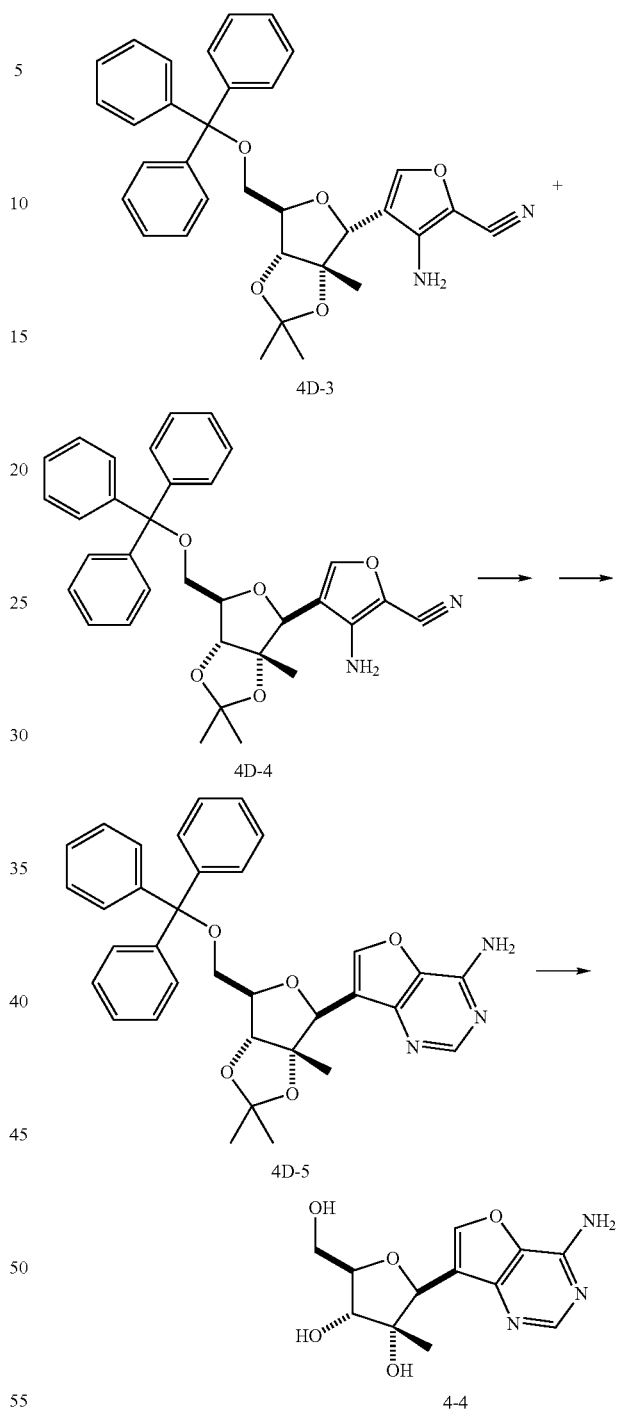

Alkylation of the enolate 4D-1 with chloroacetonitrile can be performed using a base, such as cesium carbonate, in DMF. The furan ring is then formed by a base-catalyzed ring closure as described above. The final C-nucleoside can then be obtained by an acid-catalyzed removal of the protecting groups. Any number of acids can be used, such as dry hydrogen chloride in dioxane.

The preparation of C-nucleosides having a 7-aminoisoxazolo[4,5-d]pyrimidin-3-yl nucleobase at the C-1 position of the 2-C-Me-D-ribofuranose ring can be accomplished as depicted in Schemes 5A and 5B and detailed in the description below.

The nitrile 3-3 is nitrosated under conditions well-known in the chemical literature [see, for example, Cook et al., *J. Chem. Soc.*, 3227 (1949) or Wamhof et al., *J. Org. Chem.*, 58: 5181 (1993)] to form oxime 5A-1. If epimerization at the C-1 position of the ribofuranose ring system occurs, the desired β-epimer can be separated by suitable chromatographic methods. Oxime 5A-1 is then alkylated with chloroacetonitrile in a manner analogous to that disclosed in German patent DE 2808317 (Ciba Geigy, 1978). The subsequent steps are then performed as described previously for the synthesis of 2-4 and 4A-4. The isoxazole ring is constructed by exposing 5A-2 to a strong base and the formation of the pyrimidine ring is then effected by heating the aminonitrile 5A-3 with formamidine acetate in a suitable solvent, such as ethyl alcohol. The ester protecting groups are removed during the base-induced cyclization, and the remaining benzyl ether protecting group is cleaved by hydrogenolysis to afford the desired isoxazolo[4,5-d]pyrimidine 5-5.

SCHEME 5A

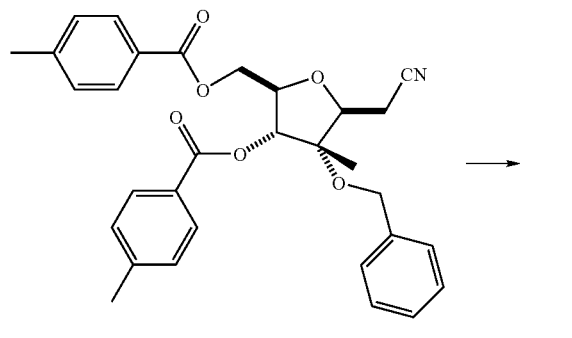

3-3

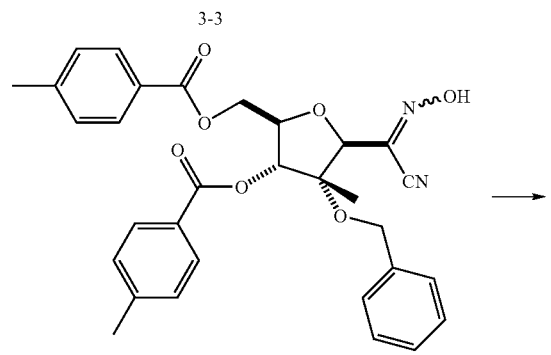

5A-1

5A-2

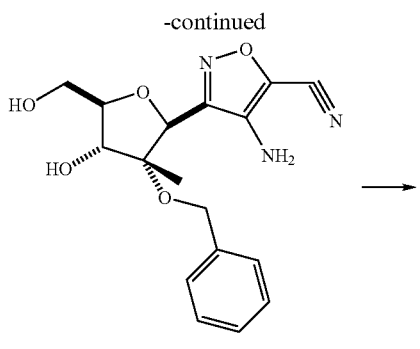

5A-3

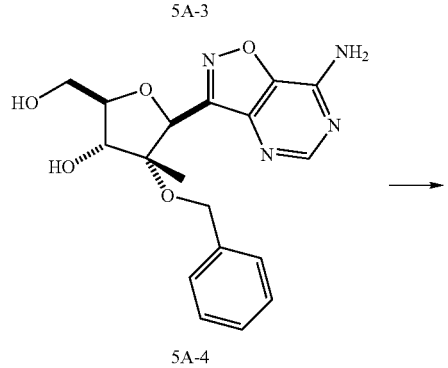

5A-4

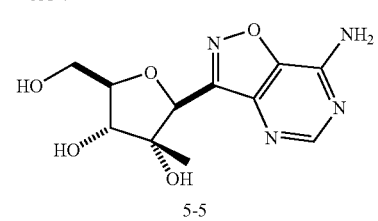

5-5

Alternatively, the target nucleoside 5-5 can be prepared as illustrated in Scheme 5B. According to this approach, the triester intermediate 4B-2 is reacted with isopentyl nitrite as described by H. Wamhof et al. in *J. Org. Chem.*, 58: 5181-5185 (1993) to afford the nitrile-oxime 5B-1. The remaining synthetic steps are analogous to those described for the chemistry illustrated in Scheme 4B.

Scheme 5B

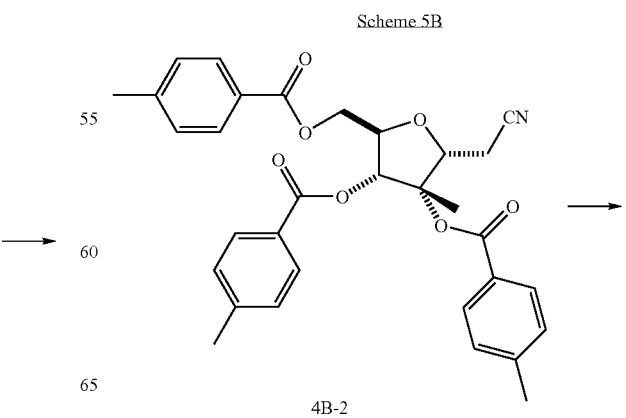

4B-2

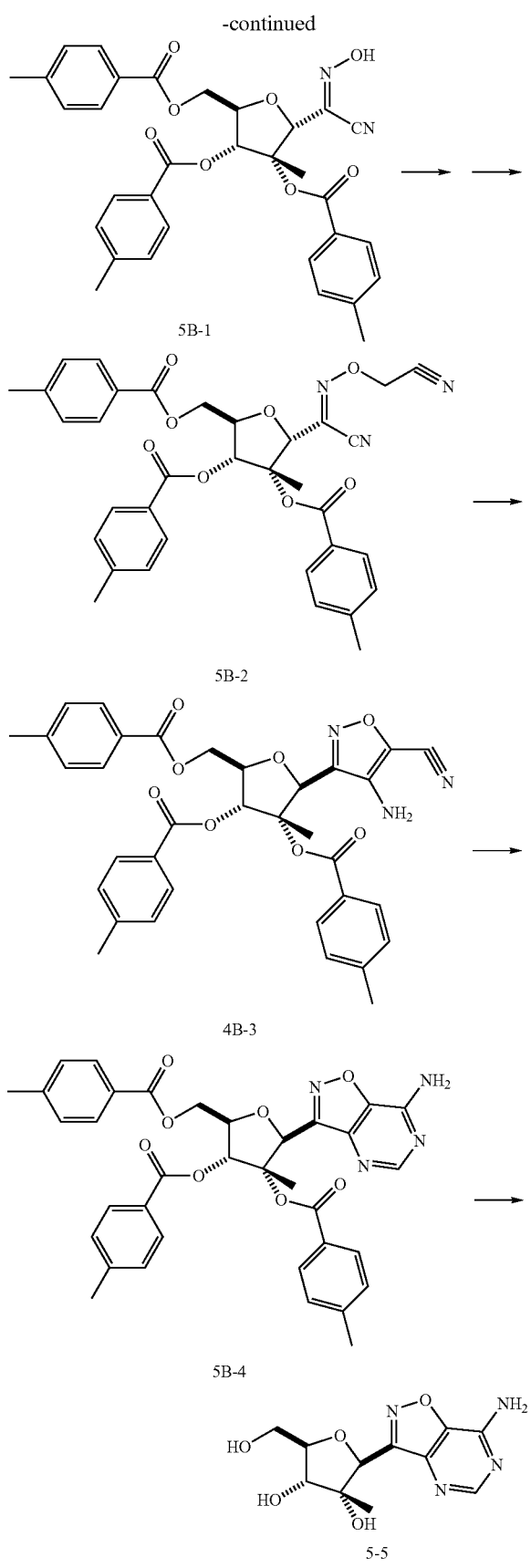

The preparation of C-nucleosides of the present invention having a 4-amino-5H-pyrrolo[3,2-d]pyrimidin-7-yl nucleobase at the C-1 position of the 2-C-Me-D-ribofuranose ring can be accomplished as depicted in Schemes 6A and 6B and detailed in the description below.

The α-hydroxymethylenenitrile 3-5, the preparation of which is depicted in Scheme 3, is reacted with aminoacetonitrile hydrochloride in a suitable solvent, such as water and aqueous methanol, in the presence of a mild base, such as sodium acetate. Reference is made to the following publications for related chemistry: Klein, R. S., Lim, M. I., *Tetrahedron Lett.* 22: 25-28 (1981) and Liang, C., et al., *Carbohyd. Res.*, 303: 33-38 (1997).

The amine functionality in 6A-1 is preferably protected as an alkylcarbamate derivative (see Greene, T. W., Wuts, P. G. M., "Protective Groups in Organic Synthesis", John Wiley & Sons, Inc., 3$^{rd}$ Edition, 1999). The dinitrile 6A-2 is then treated with a base, such as 1,5-diazabicyclo[4.3.0]non-5-ene, to facilitate the cyclization. The desired β-isomer is obtained using chromatographic methods, if necessary. The ester as well as carbamate protecting groups are removed by exposure to a mild base (e.g. potassium or sodium carbonate) in alcohol to afford 6A-4. The pyrimidine ring is then constructed as described above. The final removal of the ether protecting group affords the desired 5H-pyrrolo[3,2-d]pyrimidine nucleoside 6-6.

SCHEME 6A

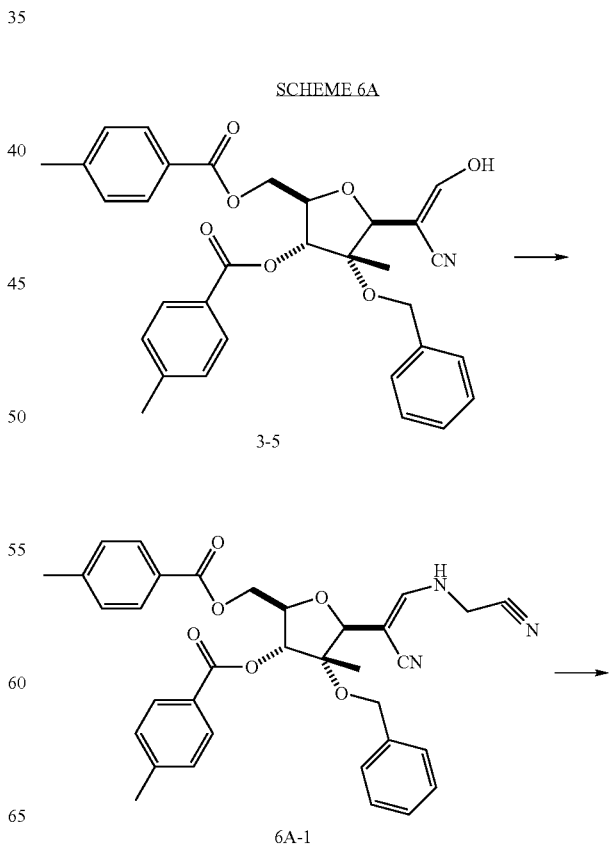

-continued

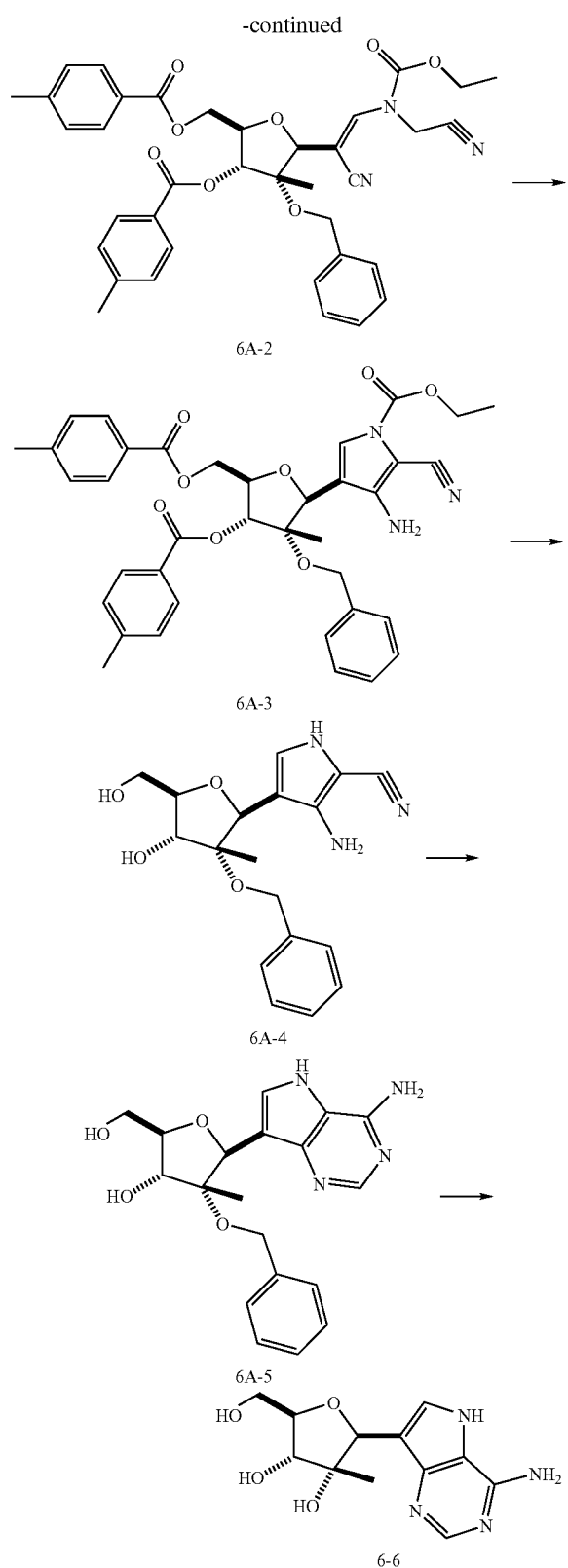

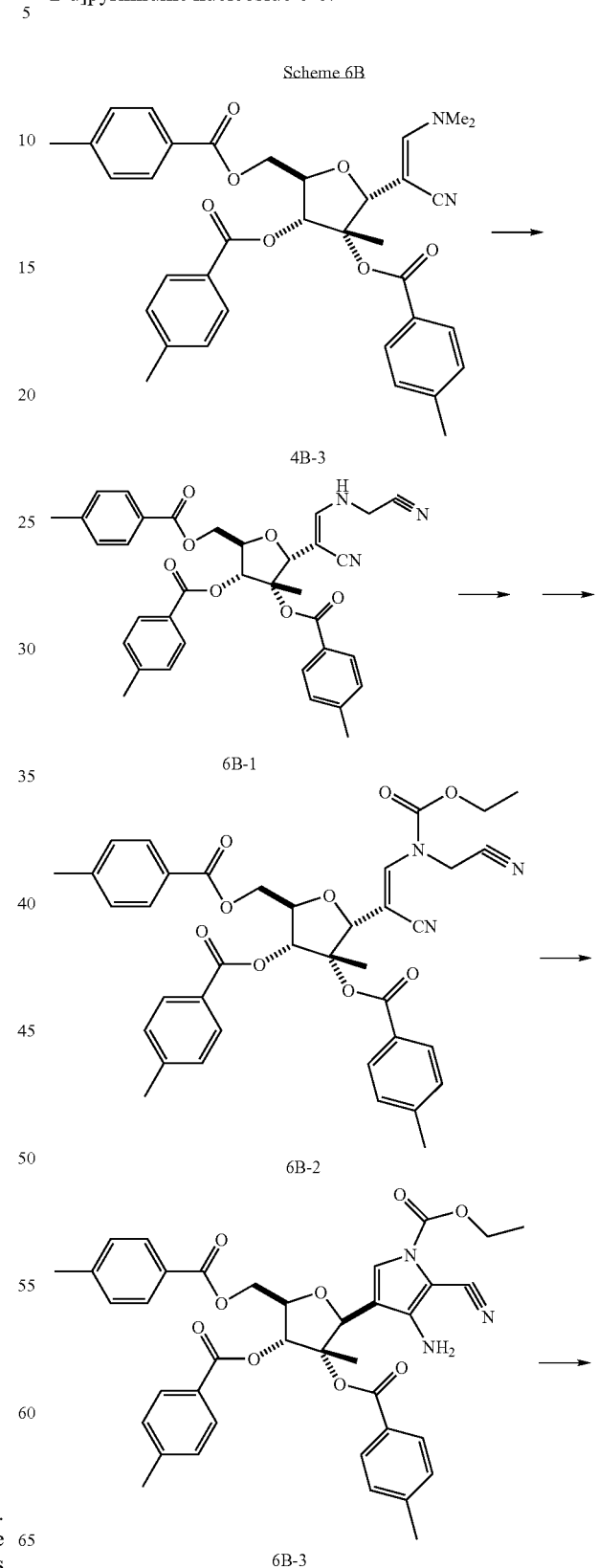

The basic nitrogen in 6B-1 is protected and the urethane 6B-2 is then carried through a sequence of steps analogous to those described in Scheme 4B to afford the desired 5H-pyrrolo[3,2-d]pyrimidine nucleoside 6-6.

An alternative synthesis of 6-6 is described in Scheme 6B. According to this approach, the dimethylamino derivative 4B-3, the preparation of which is described in Scheme 4B, is reacted with aminoacetonitrile to afford the enamine 6B-1.

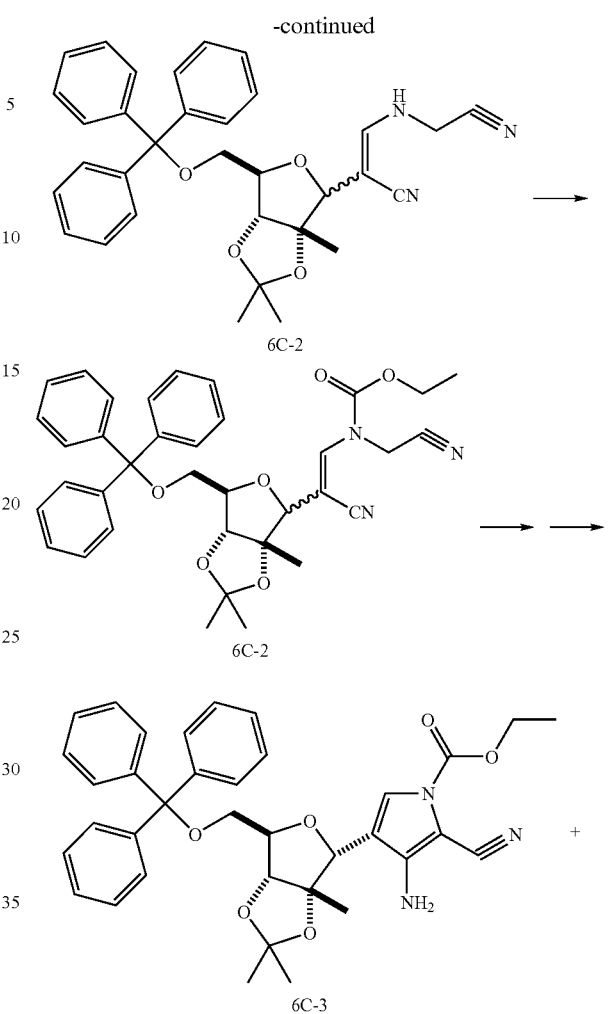

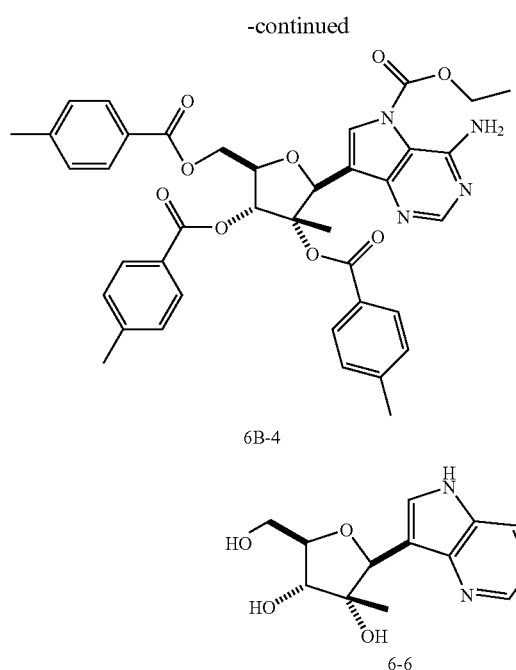

The C-nucleoside 6-6 can also be prepared by a variation of the above-described sequence, which utilizes a base-robust protecting group system, as described in the case of the furan-analog 44. This procedure is illustrated in Scheme 6C.

Starting from the cyanomethylene sugar 4C-6,7, the preparation of which was described above, the dimethylaminomethylene group a to the nitrile can be introduced following a procedure described by De Bernado, S., Weigele, M. in *J. Org. Chem.*, 42:109 (1977).

Scheme 6C

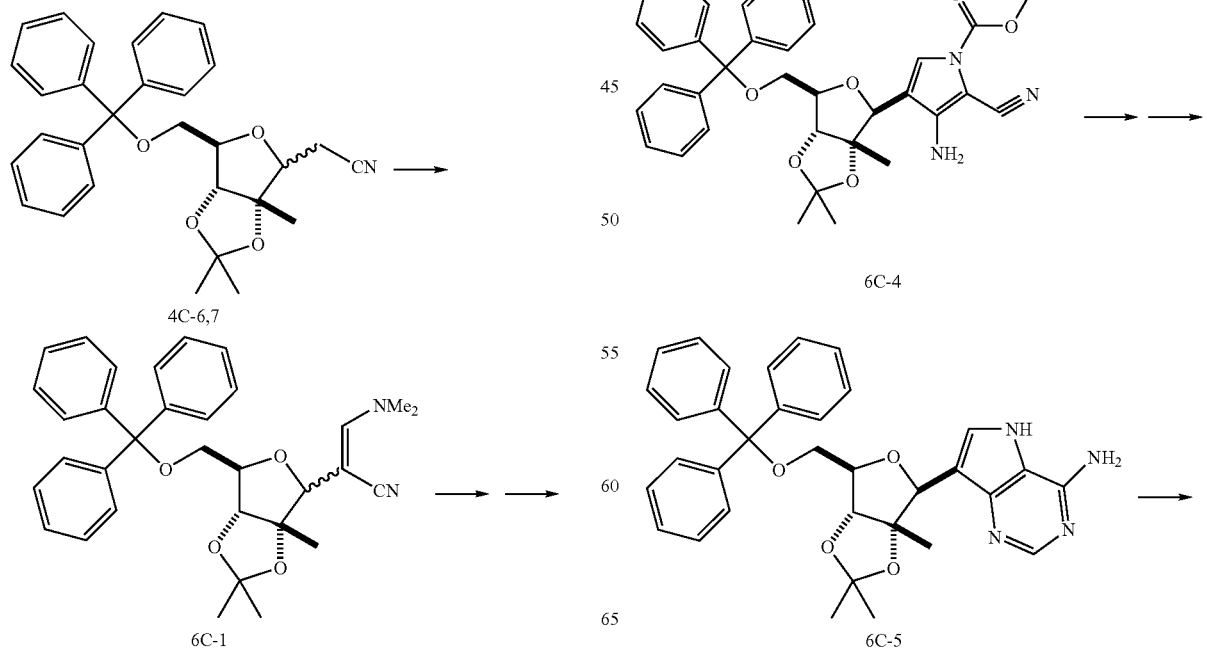

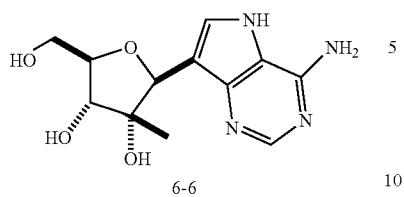

6-6

It is advantageous to proceed without purification and displace the dimethylamino group with a cyanomethylamino moiety, as described for 6B-1 above. The carbamate 6C-2 can then be synthesized following standard procedures, and the subsequent ring closure accomplished by the use of a strong base, such as DBU. The remaining steps are analogous to those described in Scheme 6B and the final C-nucleoside 6-6 can be obtained as detailed in the case of the furan analog 44.

The synthetic procedures employed in preparation of C-nucleosides of the present invention which contain an aminopyrimidinone fused to the pyrazole, furan, isoxazole, pyrrole, and thiophene rings of general formula 7-8 are detailed in Schemes 7A and 7B.

The 3,5-diol functionality in the respective aminonitriles of general formula 7A-1 is first protected with a suitable protecting group, for example, as a cyclic silyl ether. Examples of such protecting groups can be found in Greene, T. W., Wuts, P. G. M., "Protective Groups in Organic Synthesis," John Wiley & Sons, Inc., 3$^{rd}$ Edition, 1999. The nitrile group is then hydrolyzed, preferably under mildly acidic conditions, and the aromatic amino group is reacted with benzoyl thioisocyanate to form a benzoyl thiourea derivative of general formula 7A-4. When methyl iodide is allowed to react with 7A4, methylation takes place at the sulfur atom affording the thioenolether 7A-5. Ammonolysis is performed in a polar solvent which results in the formation of the fused aminopyrimidinone ring system in formula 7-7, and the final compounds are obtained after hydrogenolysis of the benzyl ether protecting group.

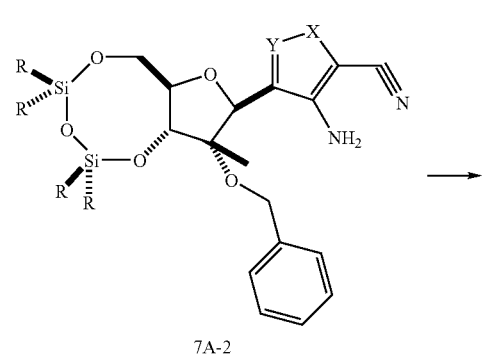

7A-2

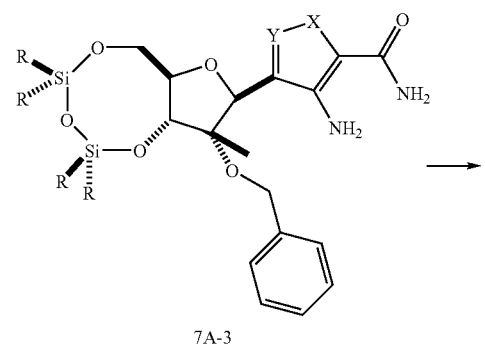

7A-3

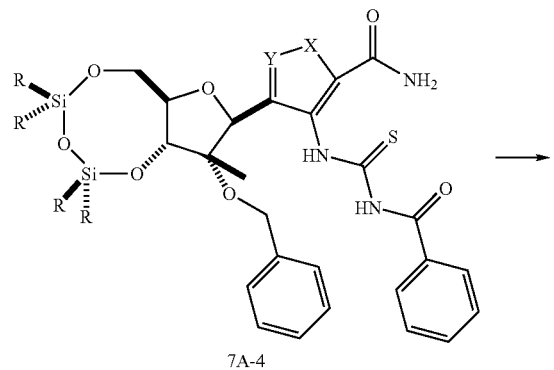

7A-4

SCHEME 7A

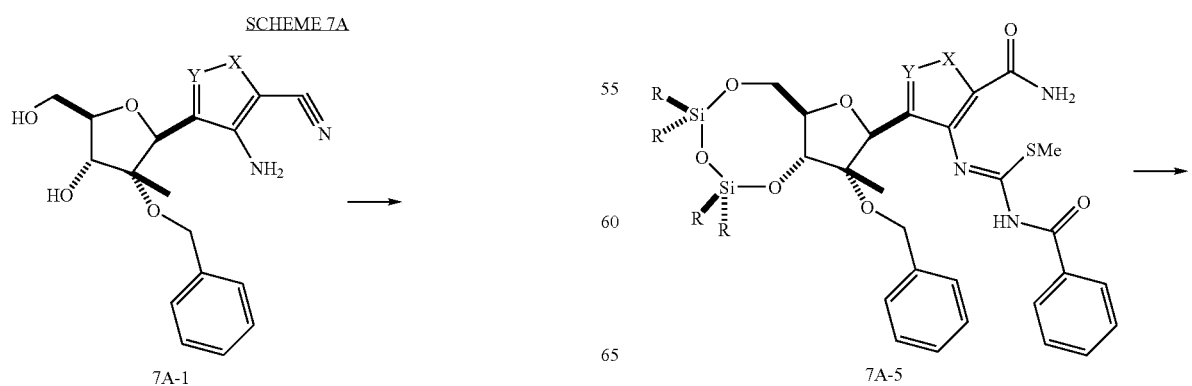

7A-1    7A-5

-continued

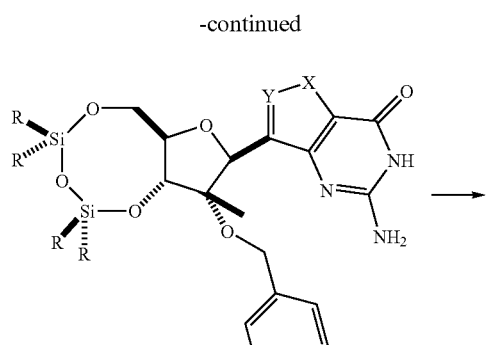

7A-6

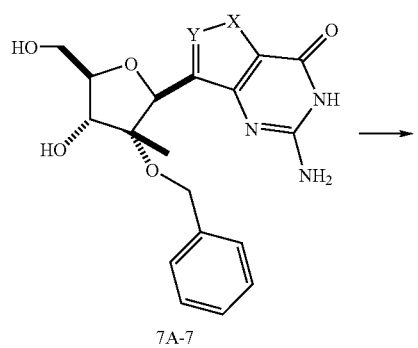

7A-7

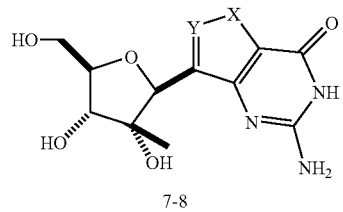

7-8

An alternative synthetic approach to aminopyrimidinones fused to the pyrazole, furan, isoxazole, pyrrole, and thiophene rings is shown in Scheme 7B.

Scheme 7B

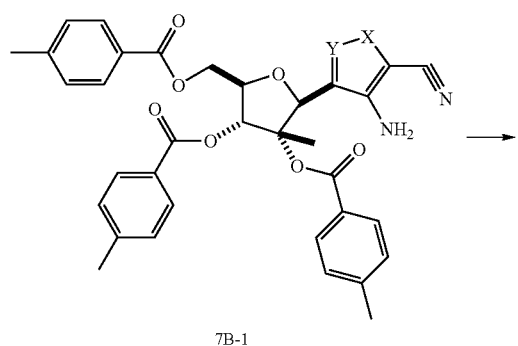

7B-1

-continued

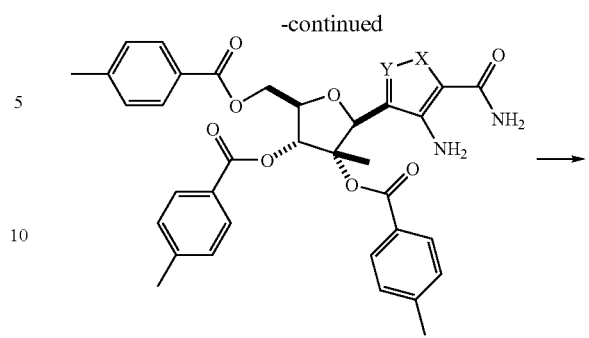

7B-2

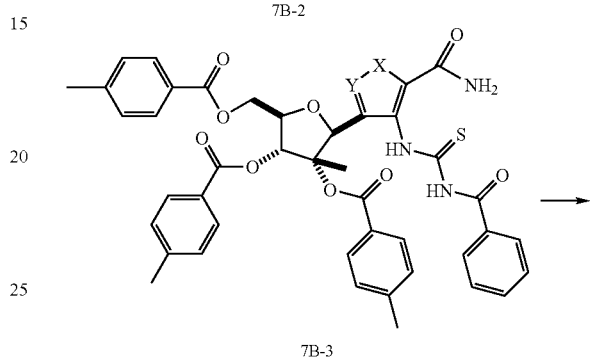

7B-3

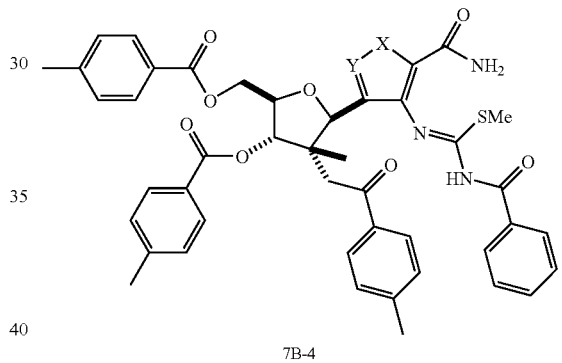

7B-4

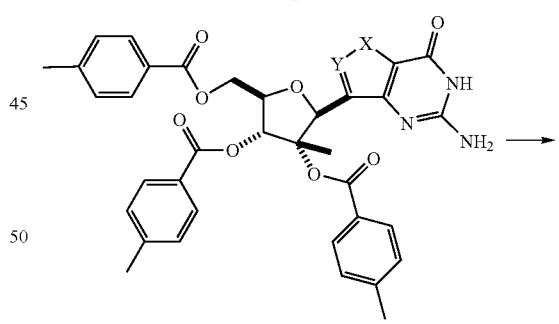

7B-5

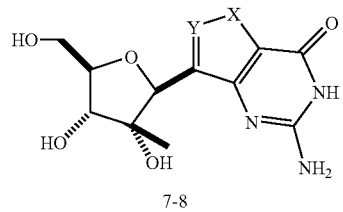

7-8

According to this approach, the aminonitriles of general formula 7B-1 are carefully hydrolyzed to afford the respective amides 7B-2 and these are then subjected to a series of steps analogous to those described in Scheme 7A. The final compounds are then obtained by removal of the protecting groups following procedures known to those skilled in the art.

The examples below provide citations to literature publications which contain details for the preparation of intermediates employed in the preparation of final compounds of the present invention. The C-nucleoside compounds of the present invention are prepared according to procedures detailed in the following examples. The examples are not intended to be limitations on the scope of the instant invention in any way, and they should not be so construed. Those skilled in the art of nucleoside and nucleotide synthesis will readily appreciate that known variations of the conditions and processes of the following preparative procedures can be used to prepare these and other compounds of the present invention. All temperatures are degrees Celsius unless otherwise noted. HPLC analyses were performed at ambient temperature using a Waters XTerra C18 reverse-phase column under following conditions: flow rate: 1.25 mL/min; eluent: acetonitrile (0.1% TFA) and water (0.1% TFA) in a three point gradient starting at 10% acetonitrile reaching 50% acetonitrile in $3^{rd}$ minute, 90% in $9^{th}$ minute and finally 100% in $10^{th}$ minute and maintained until $13^{th}$ minute at which time the eluent composition was reset to initial conditions; detector: UV at 220 nm. The LC-MS analyses were performed under identical conditions, except that the column temperature was maintained at 30° C. and the detection was performed with a diode-array Agilent 1100 detector in conjunction with a Waters Micromass ZQ mass spectrometer.

EXAMPLE 1

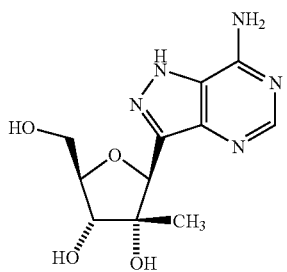

7-Amino-3-(2-C-methyl-β-D-ribofuranosyl)-1H-pyrazolo[4,3-d]pyrimidine

Step A:

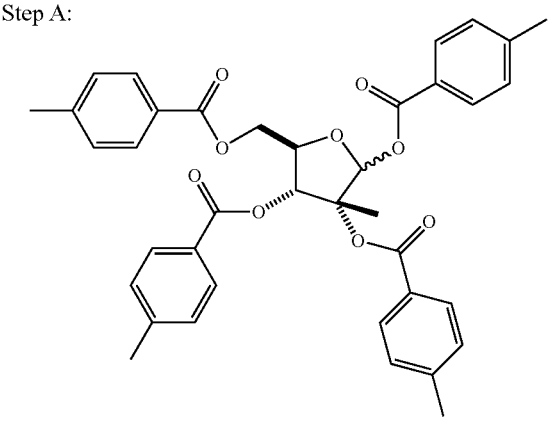

To a solution of 2-C-methyl-3,5-di-O-(4-methylbenzoyl)-D-ribofuranose [prepared following procedures described in M. Bio et al. in "Practical Synthesis of a Potent Hepatitis Virus C Polymerase Inhibitor," *J. Org. Chem.*, 69: 6257-6266 (2004)] (24.00 g, 60.00 mmol), 4-dimethylaminopyridine (1.46 g, 12.00 mmol) and triethylamine (55.00 mL, 396 mmol) in 1,2-dimethoxyethane (250 mL) at 0° C. was added p-toluoyl chloride (17.50 mL, 132.00 mmol) dropwise over a period of approximately 30 min. The cooling bath was removed, and stirring at room temperature was continued for 18 h. The reaction mixture was poured onto ice (400 g) and stirred until all the ice had melted. The solid was filtered off, the cake was washed with water (3×100 mL) and methyl t-butyl ether (MTBE) (2×100 mL). The white solid was then dried under vacuum until no more loss of weight was observed. LCMS: for $C_{38}H_{36}O_9$ calculated: 636.24; found 637.30[M+H]$^+$, 659.30 [M+Na]$^+$, and 501.20 [M−CH$_3$PhCOO]$^+$.

$^1$H NMR (500 MHz, CDCl$_3$): δ 7.96 (d, J=7.6 Hz, 4H), 7.88 (d, J=7.6 Hz, 2H), 7.68 (d, J=7.6 Hz, 2H), 7.40 m(m, 4H), 7.30 (d, J=7.3 Hz, 2H), 7.0 (d, J=7.30 Hz, 2H), 6.82 (s, 1H), 5.88 (d, J=8.2 Hz, 1H), 4.78 (m, 1H), 4.64 (bd, J=12.6 Hz, 1H), 4.42 (bd, J=12.6 Hz, 1H), 2.40 (bs, 9H), 2.28 (s, 3H), 1.83 (s, 3H). $^{13}$C NMR (500 MHz, CDCl$_3$): δ 166.1, 165.7, 164.9, 164.6, 144.6, 144.3, 144.2, 143.4, 130.0, 129.8, 129.6, 129.2, 128.8, 127.6, 126.7, 126.5, 126.2, 97.7, 86.5, 78.6, 76.0, 63.7, 21.7, 21.6, 16.8.

Step B:

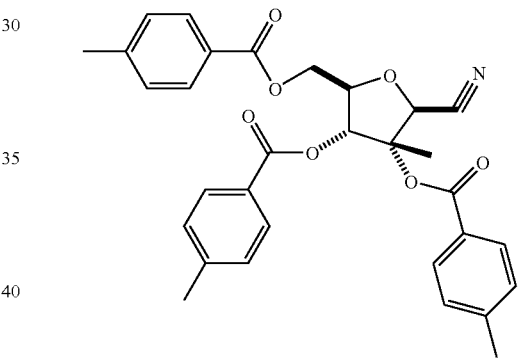

A solution of 2-C-methyl-1,2,3,5-tetra-O-(4-methylbenzoyl)-D-ribofuranose (15.00 g, 23.35 mmol) from Step A, trimethylsilyl cyanide (12.6 mL, 94.24 mmol) in 1,2-dichloroethane (200 mL) was treated with tin tetrachloride (neat, 2.71 mL) and stirring at ambient temperature was continued for 6 h. The dark mixture was then poured onto a saturated solution of sodium bicarbonate (400 mL). Chloroform (300 mL) was added, and the suspension was vigorously stirred for 1 h and then filtered through a plug of Celite. The cake was washed with additional chloroform (3×100 mL), and the organic layer was separated. The aqueous phase was washed twice with chloroform, the organic extracts were combined, back-washed with a saturated brine solution (1×200 mL) and concentrated in vacuo. The dark brown residue (16.70 g) was purified by gradient chromatography on silica gel using a mixture of hexanes and ethyl acetate as the eluent. The concentration of ethyl acetate was gradually increased from 0% at the beginning to 50% at the end of the separation. Evaporation of the appropriate fractions gave the desired compound. LCMS: for $C_{31}H_{29}O_7$ calculated: 527.19; found 528.40 [M+H]$^+$, 550.40 [M+Na]$^+$.

$^1$H NMR (500 MHz, CDCl$_3$): δ 8.00 (d, J=8.0 Hz, 2H), 7.87 (bt, J=8.23 Hz, 4H), 7.23 (bm, 6H), 5.67 (d, J=6.4 Hz,

1H), 5.27 (s, 1H), 4.76 (dd, J=12.4, 3.4 Hz, 1H), 4.63 (dd, J=12.3, 4.8 Hz, 1H) 4.53 (m, 1H), 2.44 (s, 3H), 2.43 (s, 3H), 2.42 (s, 3H), 2.03 (s, 3H). $^{13}$C NMR (500 MHz, CDCl$_3$): δ 166.2, 165.2, 164.9, 144.7, 144.0, 129.9, 129.8, 129.3, 129.2, 129.1, 126.6, 126.5, 125.8, 115.3, 83.9, 81.1, 76.1, 72.8, 62.9, 21.7, 21.6, 21.6, 19.8.

Step C:

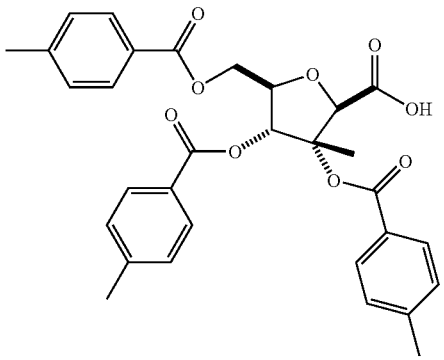

A solution of the nitrile from Step B (5.30 g, 10 mmol) in dry 1,4-dioxane (10.0 mL) was treated with 4N solution of HCl in dioxane (5.0 mL) and 540 μL (30 mmol) of water in a thick-walled tube and heated to 50° C. for 4 days. The reaction mixture was evaporated to dryness, and the residue (7.63 g) was purified by preparative medium-pressure liquid chromatography (dichloromethane+MeOH, gradient dichloromethane: 100% to 85%) to afford the desired acid. LCMS: for C$_{31}$H$_{30}$O$_7$ calculated: 546.19; found 547.30 [M+H]$^+$, 569.30 [M+Na]$^+$.

$^1$H NMR (500 MHz, CDCl$_3$): δ 7.90 (m, 4H), 7.70 (m, 2H), 7.10 (bm, 6H), 5.6 (bd, J=4.80 Hz, 1H), 5.05 (bs, 1H), 4.80 (bm, 2H), 4.50 (bs, 1H), 2.35 (m, 9H), 1.88 (bs, 3H).

Step D:

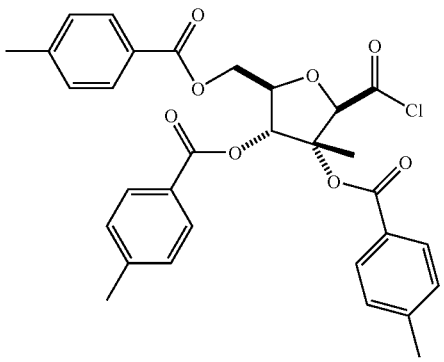

A solution of the acid from Step C (1.65 g mg, 3.01 mmol) in dichloromethane (40 mL) was cooled in an ice bath, oxalyl chloride (368 μL, 4.22 mmol) was added, followed by three drops of N,N-dimethylformamide. The cooling bath was removed, and stirring at ambient temperature was continued for 1 h. The solvent was removed in vacuo, and the residue was coevaporated with toluene (2×50 mL). The crude acid chloride was used in the subsequent step E without any additional purification.

Step E:

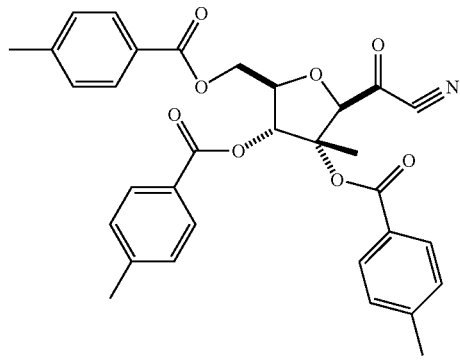

The crude acid chloride from Step D (3.01 mmol) was dissolved in dry toluene (20 mL) and neat trimethylsilyl cyanide (1.60 mL, 12.05 mmol) was added via syringe. Several drops of trimethylsilyl chloride were added to initiate the reaction, and stirring at ambient temperature was continued for 2 h. The solvent was removed in vacuo and the residue was coevaporated with toluene (2×100 mL). The crude product was used in the subsequent step F without any additional purification.

Step F:

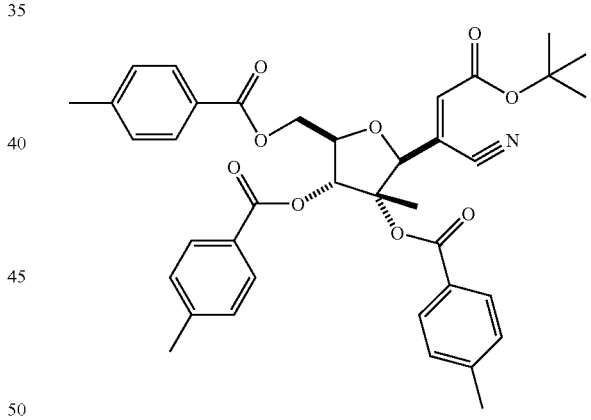

To the solution of the crude α-keto nitrile from Step E (3.01 mmol) was added solid tert-butoxycarbonylmethylene triphenylphosphorane (2.26 g, 6.027 mmol) and stirring at ambient temperature was continued overnight. The solvent was removed in vacuo, and the residue was purified using gradient flash chromatography on silica gel (eluent:ethyl acetate-hexanes (0% to 80% of ethyl acetate). Evaporation of the appropriate fractions afforded the desired product. LCMS: for C$_{38}$H$_{39}$O$_9$ calculated: 653.26; found 654.60 [M+H]$^+$, 598.5 [M−tBu]$^+$.

$^1$H NMR (500 MHz, CDCl$_3$): δ 8.02 (bt, J=7.6 Hz, 4 H), 7.72 (d, J=7.8 Hz, 2H), 7.28 (d, J=7.8 Hz, 4H), 7.08 (d, J=7.8 Hz, 2H), 6.77 (s, 1H), 5.68 (bd, J=3.2 Hz, 1H), 5.01 (s, 1H), 4.86 (bdd, J=11.9, 1.8, 1H), 4.74 (dd, J=12.1, 5.5 Hz, 1H), 4.45 (bs, 1H), 2.44 (s, 3H), 2.43 (s, 3H), 2.36 (s,3H), 1.72 (s, 3H), 1.58 (s, 9H). $^{13}$C NMR (CDCl$_3$, 500 MHz): δ 166.32, 135.28, 165.11, 161.58, 144.27, 144.19, 143.95, 136.75, 129.97, 129.80, 129.69, 129.22, 129.16, 129.04, 126.9, 126.72, 126.08, 120.92, 115.00, 114.13, 83.41, 83.28, 82.59, 82.00, 77.11, 63.45, 29.67, 27.91, 21.70, 21.65, 21.60, 18.66.

Step G:

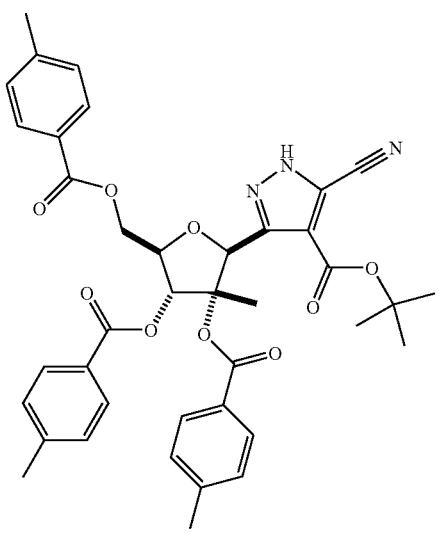

A suspension of aminoacetonitrile hydrochloride (1.56 g, 16.80 mmol) in diethyl ether (20 mL) was cooled to 0° C. and was treated dropwise with a cold solution of sodium nitrite (1.06 g, 15.3 mmol) in water (4.0 mL). The cooling bath was removed, and the reaction mixture was vigorously stirred at ambient temperature for 2 h. The yellow organic phase containing the diazoacetonitrile was separated, washed with brine, and carefully concentrated to a volume of not less than 10 mL. This solution was then combined with a solution of the ester-nitrile from Step F (1.00 g, 1.5297 mmol) in dichloromethane (4 mL). The reaction mixture was kept at ambient temperature in darkness for 4 weeks. After this time, the entire reaction mixture was loaded onto a silica-gel column, and eluted with a mixture of hexanes and ethyl acetate (gradient, 0 to 80% of EtOAc). Evaporation of the appropriate fractions afforded the desired product. LCMS for C$_{39}$H$_{39}$N$_3$O$_9$ calculated: 693.27, found 694.60 [M+H]$^+$. $^1$H NMR (500 MHz, CDCl$_3$): δ 12.04 (bs, 1H), 8.90 (d, J=8.0 Hz, 2H), 8.0 (d, J=8.2 Hz, 2H), 7.72 (d, J=8.24Hz, 2H), 7.24 (m, 5H), 7.04 (d, J=8.0Hz, 2H), 6.21 (s, 1H), 5.65 (m, 1H), 5.13 (dd, J=11.7, 0.4 Hz, 1H), 4.74 (m, 1H), 4.58 (dt, J=9.2, 2.5 Hz, 1H), 2.45 (s, 3H), 2.42 (s, 3H), 2.33 (s, 3H), 1.71 (s, 9H), 1.65 (s, 3H). $^{13}$C NMR (CDCl$_3$, 500 MHz): δ 165.6, 165.4, 159.8, 144.7, 144.3, 144.0, 143.3, 130.2, 130.0, 129.7, 129.3, 129.0, 126.7, 126.4, 125.9, 112.9, 84.3, 83.1, 83.0, 77.8, 77.2, 77.1, 76.7, 64.1, 31.5, 28.2, 22.6, 21.7, 21.7, 21.6, 19.5, 14.1.

Step H:

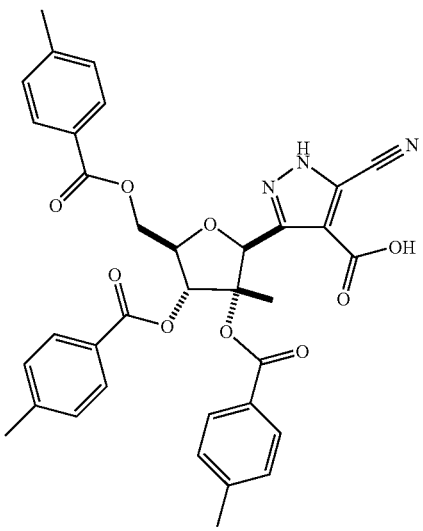

A solution of the tert-butyl ester from Step G (390 mg, 0.563 mmol) in neat formic acid (4 mL) was stirred at 75° C. for 30 min. The mixture was allowed to cool to ambient temperature, diluted with a mixture of toluene and dioxane (1:1, 50 mL), and the solvent was removed in vacuo. The residue was taken up in the toluene/dioxane mixture again, and the volatiles were distilled off. The crude material was used as obtained in the next step. LCMS for C$_{35}$H$_{31}$N$_3$O$_9$ calculated: 637.21, found 638.47 [M+H]$^+$.

Step I:

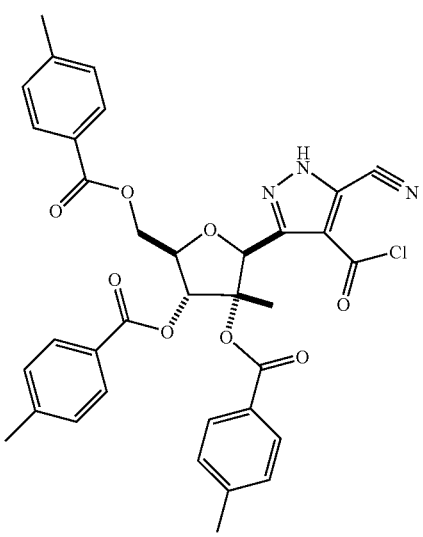

A solution of the acid from Step H (298 mg, 0.4673 mmol) in dry dichloromethane (10 mL) was cooled to 0° C. and treated with oxalyl chloride (60 μL, 0.70 mmol), followed by three drops of dry DMF. The cooling bath was removed, and the reaction mixture was stirred for 2 h. The solvent was removed at reduced pressure and the residue was co-distilled two times with toluene (50 mL). The crude acid chloride was used in the next step without any additional purification. It was characterized by LCMS as its methyl ester derivative, after a sample was quenched with methanol. LCMS for $C_{36}H_{33}N_3O_9$ calculated: 651.22, found 652.60 $[M+H]^+$.

Step J:

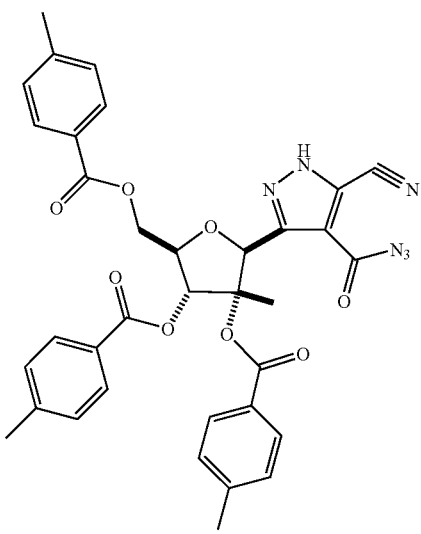

A solution of the chloride from Step I (102 mg, max 0.4673 mmol) in dichloromethane (4 mL) was cooled to 0° C. and an aqueous (4 mL) solution of sodium azide (303 mg, 4.67 mmol) containing a spatula tip of tetra-n-butylammonium chloride and vigorously stirred in the cold for 1 h. The organic phase was separated, and the aqueous layer was washed with dichloromethane (3×25 mL). The combined organic phases were back washed with brine, dried (magnesium sulfate) and the solvent was removed under reduced pressure.

LCMS for $C_{35}H_{30}N_6O_8$ calculated: 662.21, found 663.60 $[M+H]^+$.

Step K:

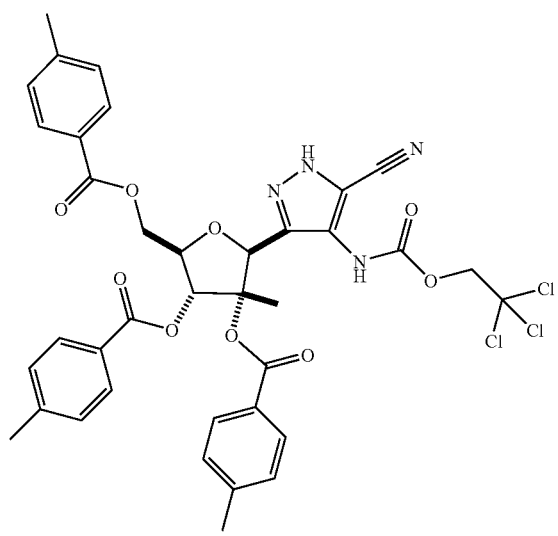

A solution of the crude acyl azide from Step J (338 mg, max. 0.4673 mmol) in toluene (6 mL) was heated to 80° C. for 3 h. The solvent was removed in vacuo, and the residue was purified by flash chromatography (silica-gel, mixture of ethyl acetate/hexanes, gradient 0 to 60% of ethyl acetate) to yield the desired compound. LCMS for $C_{37}H_{33}Cl_3N_4O_9$ calculated: 782.13, found 785.61 $[M+H]^+$.

$^1$H NMR (500 MHz, CDCl$_3$): δ 7.97 (d, 7.6 Hz, 2H), 7.92 (d, J=11.0 Hz, 2H), 7.86 (bs, 2H), 7.20 (bm, 6H), 5.69 (s, 1H), 5.54 (m, 1H), 4.74 (m, 1H), 4.59 (m, 1H), 2.45 (s, 3H), 2.44 (s, 3H), 2.41 (s, 3H), 1.58 (s, 3H). $^{13}$C NMR (500 MHz, CDCl$_3$): δ 144.8, 144.7, 144.5, 129.9, 129.8, 129.7, 129.4, 129.3, 129.2, 126.4, 125.8, 122.2, 76.9, 75.0, 63.7, 31.6, 22.6, 21.7, 21.6, 19.6, 14.0.

Step L:

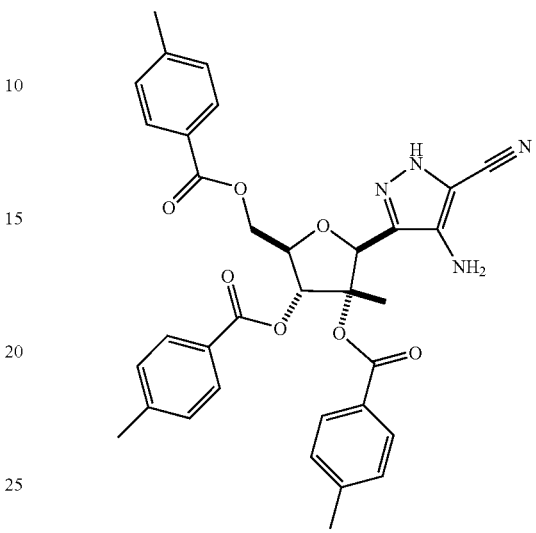

A solution of the urethane from Step K (170 mg, 0.217 mmol) in methanol (10 mL) was treated with ammonium chloride (787 mmol) and metallic zinc (2.00 g). The resulting suspension was heated to 80° C. in a sealed tube. The solvent was evaporated to dryness, and the slurry was partitioned between water (20 mL) and toluene (20 mL). After addition of 2.0 mL of concentrated ammonium hydroxide, the organic layer was separated, and the aqueous layer was extracted two more times with toluene. The combined organic extracts were back-washed with brine, dried (magnesium sulfate), filtered and evaporated to dryness to afford the desired product. The crude product was used in the subsequent step without any additional purification. LCMS for $C_{34}H_{32}N_4O_7$ calculated: 608.23, found 609.50 $[M+H]^+$.

Step M:

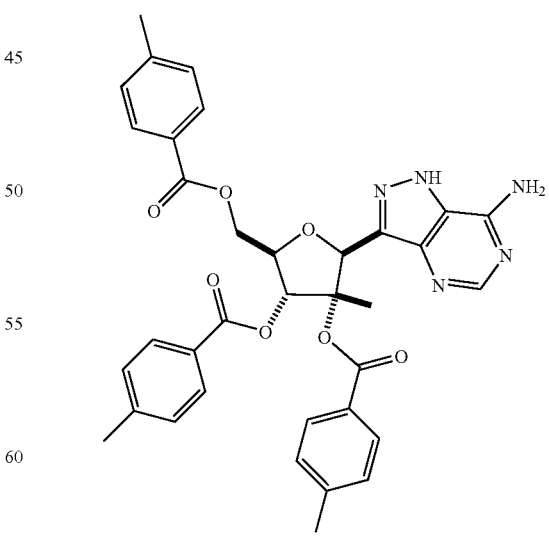

A solution of the aminonitrile from Step L (100 mg, 0.164 mmol) and formamidine acetate (300 mg, 2.88 mol) in ethyl alcohol (4 mL) was heated in a sealed tube to 105° C. for 4 h.

The reaction mixture was allowed to cool to ambient temperature and the solvent was removed in vacuo. The crude product was further purified by preparative TLC using ethyl acetate as the eluent. LCMS for $C_{35}H_{33}N_5O_9$ calculated: 635.24, found 636.70 [M+H]$^+$. $^1$H NMR (500 MHz, CDCl$_3$): δ 8.43 (s, 1H), 8.08 (d, J=6.9 Hz, 2H), 7.92 (d, J=7.1 Hz, 2H), 7.84 (d, J 7.1 Hz, 2H), 7.25 (d, H=7.1 Hz, 2H), 7.13 (t, J=8.0 Hz, 4H), 6.15 (s, 1H), 6.02 (s, 1H), 4.95 (m, 3H), 4.65 (s, 1H), 2.25 (s, 3H), 2.35 (s, 3H), 1.57 (s, 3H). $^{13}$C NMR (500 MHz, CDCl$_3$): δ 166.00, 135.69, 144.54, 144.29, 130.32, 130.12, 130.09, 129.40, 127.62, 126.89, 126.59, 79.47, 77.54, 64.91, 51.77, 21.97, 21.93, 21.89, 19.15.

Step N:

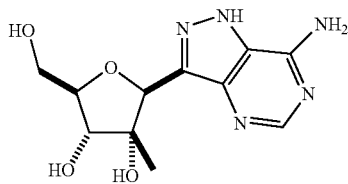

A solution of the tri-ester from Step M (17 mg, 0.0267 mmol) in anhydrous methanol (6 mL) was treated with a solution of sodium methoxide in methanol (0.5M, 900 μL) and stirring at ambient temperature was continued overnight. The reaction was quenched with addition of 1 mL of glacial acetic acid, toluene (20 mL) was added and the solution was evaporated to dryness. The residue was partitioned between water (6 mL) and t-butyl methyl ether (TBME) (20 mL). The aqueous phase was washed with TBME (10 mL) one more time and the combined organic extracts were back washed with water (6 mL). The combined aqueous extracts were micro-filtered and vaporated to dryness. The pure product was obtained by a mass-directed (m=282) preparative LC, using Waters Atlantis (21×150 mm) column and a 90:10 mixture of water and methanol, buffered with 10 mM ammonium formate. The combined fractions containing the product were evaporated to dryness, and the ammonium formate was removed by repeated lyophilization. LCMS for $C_{11}H_{15}N_5O_4$ calculated: 281.11, found 282.40 [M+H]$^+$. $^1$H NMR (600 MHz, CD$_3$CN): δ 8.16 (s, 1H, 2-H), 5.26 (s, 1H, 1'-H), 4.20 (d, J=8.4 Hz, 1H, 3'-H), 3.97 (dd, J=12.2, 2.1 Hz, 1H, 5''-H), 3.92 (dt, J=8.7, 2.1 Hz, 1H, 3'-H), 3.71 (dd, J12.4, 2.1 Hz, 1H, 5'-H), 0.82 (s, 3H, C$_2$'-Me). $^{13}$C NMR (600 MHz, CD$_3$CN): δ 152.0 (C6), 151.6 (C2), 143.2(C9), 138.5 (C4), 84.3 (C1'), 82.8 (C4'), 79.8 (C2'), 73.4 (C3') and 60.7 (C5').

EXAMPLE 2

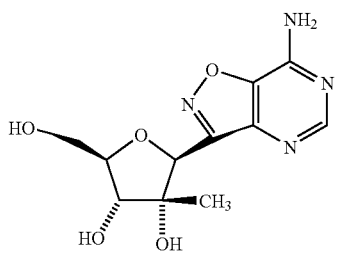

7-amino-3-(2-C-methyl-β-D-ribofuranosyl)-isoxazolo[4,5-d]pyrimidine

Step A:

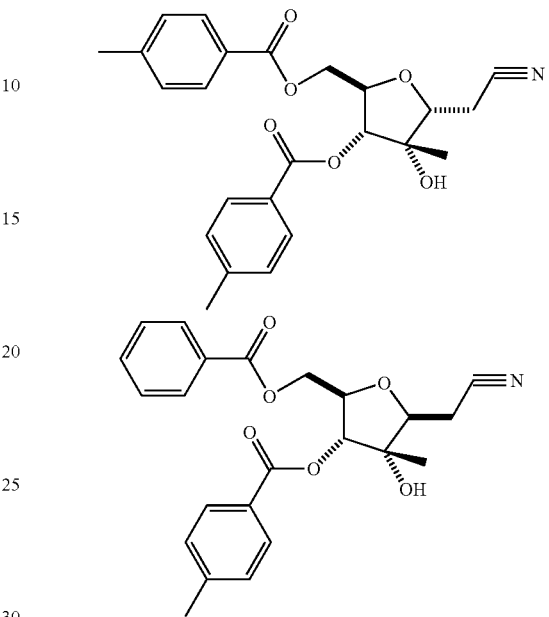

A suspension of sodium hydride (2.38 g, 59.61 mmol, 60% dispersion in oil) in anhydrous 1,2-dimethoxyethane (10 mL) was cooled in an ice bath and treated dropwise with a solution of diethyl cyanomethylphosphonate (11.73 g, 66.25 mL) in anhydrous 1,2-dimethoxyethane (10 mL) during a period of 30 min. Stirring in the cold was continued for another 30 min. To the reaction mixture, a solution of 2-C-methyl-3,5-di-O-(4-methylbenzoyl)-D-ribofuranose (6.63 g, 16.56 mmol) in dry 1,2-dimethoxyethane (20 mL) was added dropwise over 45 min. At the end of the addition the cooling bath was removed, and the reaction mixture was stirred for an additional 2 h. The reaction was quenched by pouring onto 100 mL of water, and the crude product was extracted with MTBE (3×100 mL). The combined ethereal extracts were backwashed with brine, evaporated to dryness, and the crude material (13.7 g) was purified by gradient flash silica gel chromatography (ethyl acetate-hexanes, 0% to 100%). In this manner, both the α- and the β-isomers at C-1 of the ribofuranose moiety were obtained. α-Isomer: LCMS: for $C_{24}H_{26}O_6$ calculated: 423.17; found 424.30 [M+H]$^+$, 446.30 [M+Na]$^+$.

$^1$H NMR (500 MHz, CDCl$_3$): δ 7.94 (d, J=8.2 Hz, 2H), 7.88 (d, J=8.2 Hz, 2H), 7.26 (d, J=8.0 Hz, 2H), 7.18 (d, J=8.0Hz, 2H), 5.42 (d, J=7.4 Hz, 1H), 4.57 (m, 1H), 4.50 (m, 2H), 4.23 (t, J=6.5 Hz, 1H), 2.83 (dd, J=17.0, 6.6 Hz, 1H), 2.76 (d, J=17.0, 6.6 Hz, 2H), 2.45 (s, 3H), 2.40 (s, 3H), 1.50 (s, 3H). $^{13}$C NMR (500 MHz, CDCl$_3$): δ 166.21, 165.52, 144.78, 143.82, 129.86, 129.64, 129.31, 129.06, 126.80, 125.84, 117.30, 80.42, 77.89, 77.56, 77.19, 64.03, 23.24, 21.70, 21.62, 17.90.

β-Isomer: LCMS: for $C_{24}H_{26}O_6$ calculated: 423.17; found 424.30 [M+H]$^+$, 446.20 [M+Na]$^+$.

$^1$H NMR (500 MHz, CDCl$_3$): δ 7.30 (t, J=7.8 Hz, 4H), 7.26 (d, J=8.0 Hz, 2H), 7.22 (J=8.0 Hz, 2H), 5.08 (d, J=5.0, 1H), 4.63 (dd, J=12.1, 3.9 Hz, 1H), 4.53 (dd, J=12.0, 5.3 Hz, 2H), 4.41 (dd, J=9.2, 5.0 Hz, 1H), 4.09 (dd, J=7.6, 5.0 Hz, 1H), 2.67 (dd, J=16.9, 5.0 Hz, 1H), 2.59 (dd, J=16.9, 7.8 Hz, 2 H), 2.56 (m, 1H), 2.44 (s, 3H), 2.41 (s, 3H), 1.44 (s, 3H). $^{13}$C NMR (500 MHz, CDCl$_3$): δ 166.23, 166.10, 144.66, 143.91, 129.79, 129.66, 129.27, 129.03, 126.73, 125.99, 116.88, 80.02, 78.39, 76.95, 63.62, 21.67, 21.60, 20.84, 18.52.

Step B:

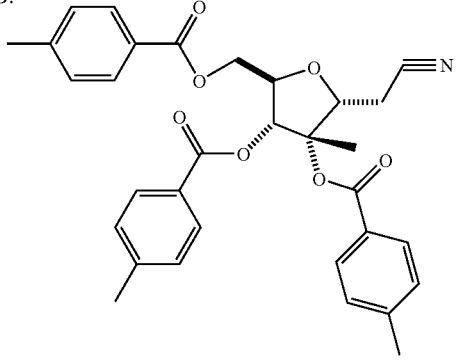

A solution of p-toluoyl chloride (451 μL, 3.415 mmol) in dichloromethane (10 mL) was added dropwise to a solution of the α-isomer from Step A (1.2051 g, 2.846 mmol), triethylamine (1.19 mL, 8.54 mmol), and 4-dimethylaminopyridine (347 mg, 2.845 mmol) in 1,2-dimethoxyethane (20 mL) and the resulting mixture was stirred at 75° C. for 18 h. The solvent was removed in vacuo, the residue was taken up into a saturated solution of sodium bicarbonate (20 mL) and extracted with dichloromethane (4×80 mL). The combined organic extracts were back-washed with brine, dried (anhydrous magnesium sulfate) and the solvent was removed in vacuo. The crude material was purified by gradient column chromatography (silica-gel, ethyl acetate/hexanes (0% to 60%) to give the desired product. LCMS: for $C_{32}H_{31}NO_7$ calculated: 541.21, found 542.60 [M+H]$^+$.

$^1$H NMR (500 MHz, CDCl$_3$): δ 7.98 (d, J=8.0 Hz, 2H), 7.86 (d, J=8.2 Hz, 2H), 7.76, (d, J=8.2 Hz, 2H), 7.26 (d, J=8.0 Hz, 2H), 7.21 (d, 8.0 Hz, 2H)m 7.14 (d, J=8.0 Hz, 2H), 5.64 (d, J=3.9 Hz, 1H), 4.80 (dd, J=11.9, 3.4 Hz, 1H, 4.69 (dd, J=12.1, 5.3 Hz, 1H), 4.63 (t, J=6.6Hz, 1H), 4.54 (m, 1H), 2.96 (m, 2H), 2.43 (s, 6H), 2.39 (s, 3H), 1.95 (s, 3H). $^{13}$C NMR (500 MHz, CDCl$_3$): δ 166.23, 165.18, 164.95, 144.43, 143.93, 129.77, 129.61, 129.24, 129.21, 129.14, 126.80, 126.64, 126.06, 116.96, 114.98, 83.31, 81.36, 76.92, 63.6822.86, 21.66, 21.64, 19.16.

Step C:

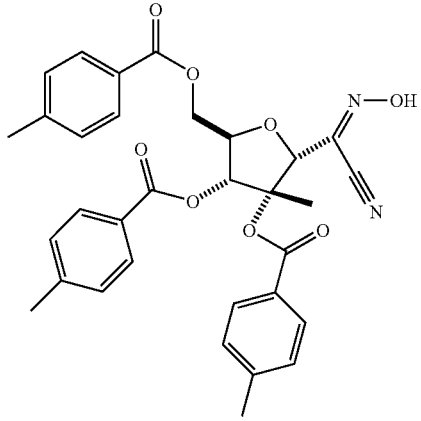

This compound is synthesized from the intermediate of Step B using a procedure analogous to that described by H. Wamhof et al. in *J. Org. Chem.*, 58: 5181-5185 (1993).

Step D:

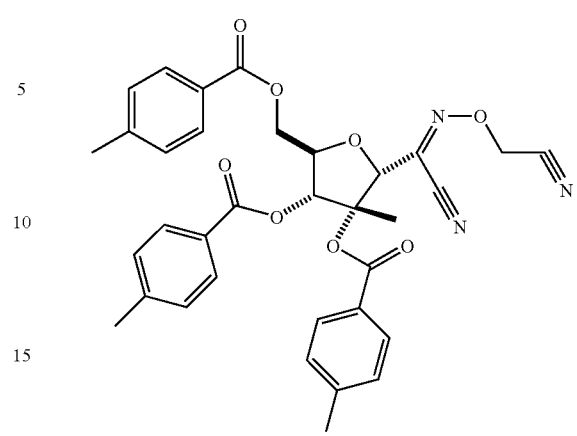

This compound is synthesized from the intermediate of Step C using a procedure analogous to that described by B. Bhattacharya et al. in *Tetrahedron Lett.*, 27: 815-818 (1986).

Step E:

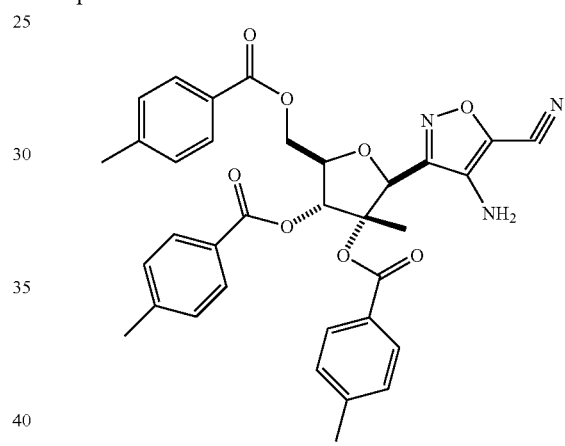

This compound is synthesized from the intermediate of Step D using a procedure analogous to that described by B. Bhattacharya et al. in *Tetrahedron Lett.*, 27: 815-818 (1986). The α- and β-isomers at C-1 of the ribofuranose moiety are isolated using chromatography on silica gel.

Step F:

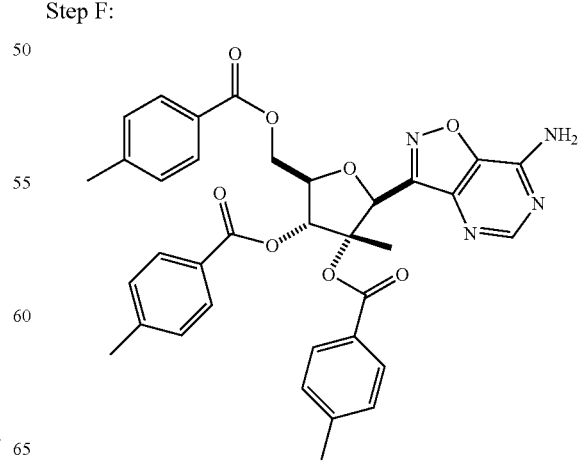

This compound is synthesized from the intermediate of Step E using a procedure analogous to that described by L. Kalvoda in *Coll. Czech. Chem. Comm.*, 43: 1431-1437 (1977).

Step G:

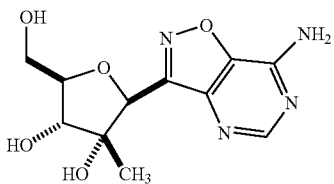

This compound is synthesized from the intermediate of Step F using a procedure analogous to that described by L. Kalvoda in *Coll. Czech. Chem. Comm.*, 43: 1431-1437 (1977).

EXAMPLE 3

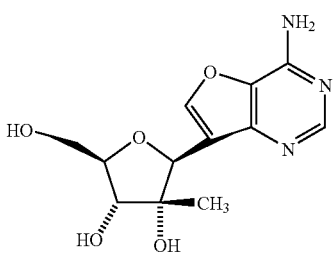

4-Amino-7-(2-C-methyl-β-D-ribofuranosyl)-furo[3,2-d]pyrimidine

Step A:

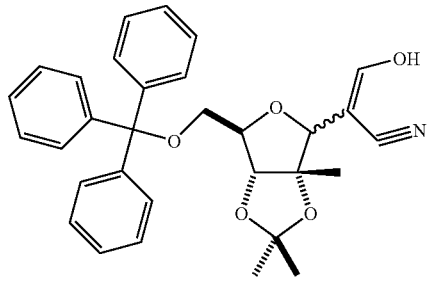

A solution of the nitrile from Step F of Example 4 (minor isomer, 232 mg, 0.5 mmol) in THF (3 mL) was added to a −78° C. cold solution of LDA (generated from 142 μL of diisopropylamine, and 400 μL of n-BuLi (2.5 M in hexanes)) in THF (3 mL), and stirring at cold was continued for 30 min. Neat methyl formate (60 μL, 1 mmol) was then added via syringe and stirring at −78° C. was continued for another 1 h. The cooling bath was removed, and the temperature of the reaction mixture was allowed to come into equilibrium with an ice-water bath, and this temperature was maintained for 15 min. The reaction was quenched with an aqueous solution of citric acid (10 mL, 10%) and the product was extracted with chloroform (3×30 mL). The combined extracts were washed with brine (1×20 mL), dried (sodium sulfate) and the solvent was removed in vacuo. The crude product was used in the subsequent step without any additional purification. LCMS for $C_{31}H_{31}NO_5$ calculated: 497.22, found 498.30 [M+H]$^+$.

Step B:

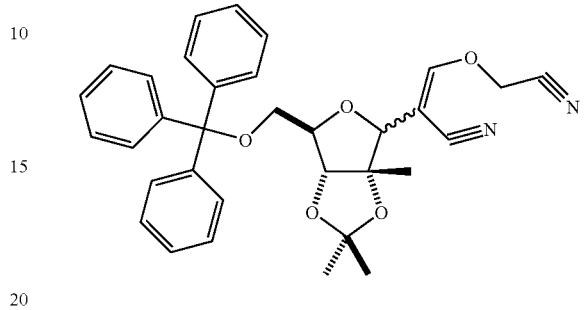

The solution of the crude product from Step A (260 mg, max. 0.50 mmol) in DMF (4 mL) was treated with chloroacetonitrile (300 μL). Cesium carbonate (700 mg) was added and stirring at ambient temperature was continued overnight. The reaction mixture was poured into water (20 mL) and extracted with TBME (3×30 mL). The combined organic phases were backwashed with brine, dried (sodium sulfate) and the solvent was evaporated to dryness. The crude product was used in the next step without any additional purification. LCMS for $C_{33}H_{32}N_2O_5$ calculated: 536.23, found 559.30 [M+Na]$^+$.

Step C:

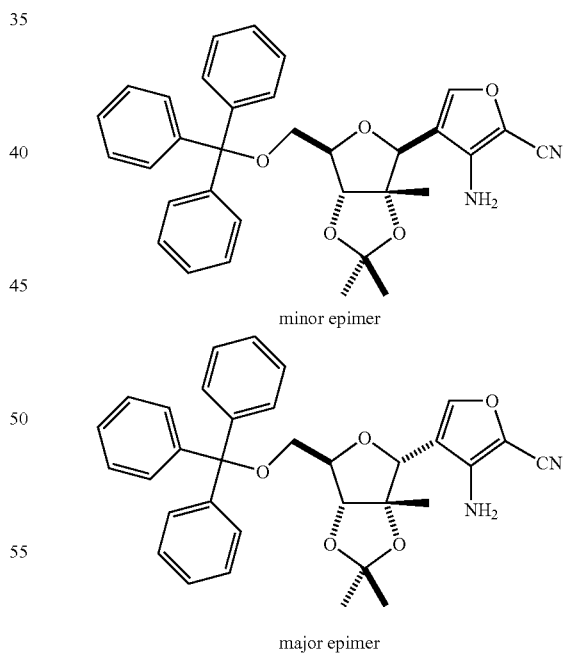

minor epimer major epimer

A solution of lithium diisopropylamide was generated from nBuLi (2.5 M in hexanes, 2.1 mL, 5.20 mmol) and diisopropylamine (730 μL, 5.20 mmol) in THF (6 mL) at −78° C. To this solution was added via syringe a solution of the crude dinitrile preparation from Step B (465 mg, 0.867 mmol) in THF (4 mL). The reaction mixture was stirred at −78° C. for an additional 2 h, after which time it was quenched with a saturated solution of ammonium chloride (20 mL). The crude product was extracted with TBME (4×30 mL), the combined organic extracts were backwashed with brine (1×30 mL), dried with anhydrous magnesium sulfate, and the solvent was removed in vacuo. The residue was passed through a silica gel column, using a gradient of ethyl acetate in hexanes (0 5 to 70%) to obtain the two respective C-1 epimers.

Major (Low Rf) Epimer: $^1$H NMR (500 MHz, CD$_3$OD): δ 7.48 (m, 6H), 7.35 (m, 6H), 7.30 (m, 4H), 4.74 (s, 1H), 4.52 (d, J=0.7 Hz, 1H), 4.35 (m, 3H), 3.38 (dd, J=10.3, 5.0 Hz, 1H), 3.30 (dd, J=10.1, 5.0 Hz, 1H), 1.52 (s, 3H), 1.47 (s, 3H), 1.46 (s, 3H). $^{13}$C NMR (600 MHz, CD$_3$OD): δ 145.62, 144.69, 143.36, 128.67, 128.58, 127.92, 127.82, 127.24, 127.17, 113.84, 113.13, 112.76, 110.41, 90.34, 88.12, 87.33, 83.35, 80.87, 63.48, 31.52, 27.83, 27.56, 22.40. LCMS for C$_{33}$H$_{32}$N$_2$O$_6$ calculated: 536.23, found 559.20 [M+Na]$^+$.

Minor (High Rf) Epimer: $^1$H NMR (500 MHz, CDCl$_3$): δ 7.48 (m, 6H), 7.34 (m, 6H), 7.28 (m, 3H), 7.22 (s, 1H), 4.74 (s, 1H), 4.31 (m,3H), 3.41 (dd, J=10.3, 3.9 Hz, 1H), 3.36 (dd, J=10.5, 4.6 Hz, 1H), 1.62 (s, 3H), 1.41 (s, 3H), 1.24 (s, 3H). $^{13}$C NMR (600 MHz, CDCl$_3$): δ 143.61, 143054, 143.44, 128.70, 127.85, 127.20, 115.43, 114.76, 112.81, 89.00, 87.00, 86.91, 82.77, 81.00, 63.54, 29.67, 28.11, 26.53, 19.55. LCMS for C$_{33}$H$_{32}$N$_2$O$_6$ calculated: 536.23, found 559.20 [M+Na]$^+$.

Step D:

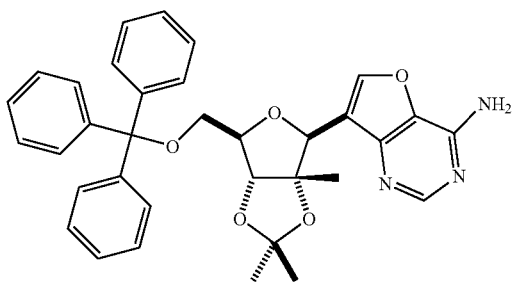

A solution of the amino nitrile from Step C (Minor epimer, 37 mg, 0.069 mmol) in ethanol (3 mL) was treated with formamidine acetate (214 mg, 2.07 mmol) and heated to 85° C. in a sealed tube for 12 h. The solvent was removed in vacuo, and the crude product was purified by preparative TLC (dichloromethane+MeOH/9:1) to obtain the desired product. $^1$H NMR (500 MHz, CD$_3$OD): δ 8.24 (s, 1H), 7.88 (s, 1H), 7.50 (m, 6H), 7.31 (m, 6H), 7.25 (m, 3H), 5.17 (s, 1H), 4.30 (d, J=3.0 Hz, 1H), 4.25 (m, 1H), 3.34 (d, J=5.04 Hz, 2H), 1.63 (s, 3H), 1,37 (s, 3H), 1.17 (s, 3H). $^{13}$C NMR (500 MHz, CD$_3$OD): δ 154.42, 148.51, 145.23, 129.95, 128.87, 128.25, 120.04, 115.85, 90.70, 89.18, 88.23, 83.78, 82.65, 65.21, 28.64, 27.31, 21.69. LCMS for C$_{34}$H$_{33}$N$_3$O$_5$ calculated: 563.24, found 564.40 [M+H]$^+$.

Step E:

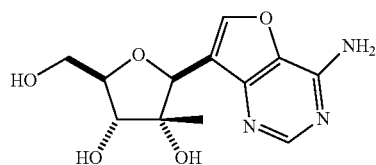

A solution of the protected nucleoside from Step D (15.7 mg, 0.028 mmol) in methanol (3 mL) was treated with a solution of HCl in dioxane (4N, 1 mL) and stirred at ambient temperature for 2 h. The solvent was removed in vacuo, and the residue was partitioned between water (10 mL) and dichloromethane (20 mL). The aqueous phase was extracted with dichloromethane two more times, the combined organic layers treated with charcoal and filtered through Celite. The filtrate was concentrated to a volume of about 5 mL and micro-filtered. The filtrate was evaporated to dryness, and the residue was triturated with acetonitrile. After crystallization, the supernatant was removed with a pipette, the solid was washed with small amount of acetonitrile and dried under high vacuum. LCMS for C$_{12}$H$_{15}$N$_3$O$_5$ calculated: 281.10, found 282.50 [M+H]$^+$. $^1$H NMR (500 MHz, CD$_3$OD): δ 8.47 (s, 1H), 8.26 (s, 1H), 5.09 (s, 1H), 4.02 (d, J=13.0 Hz, 1H), 3.96 (bs, 1H), 3.87 (d, J=11.7 Hz, 1H), 3.82 (d, J=7.4 Hz, 1H), 1.00 (s, 3H).

EXAMPLE 4

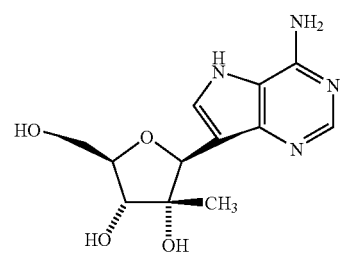

4-Amino-7-(2-C-methyl-β-D-ribofuranosyl)-5H-pyrrolo[3,2-d]pyrimidine

Step A:

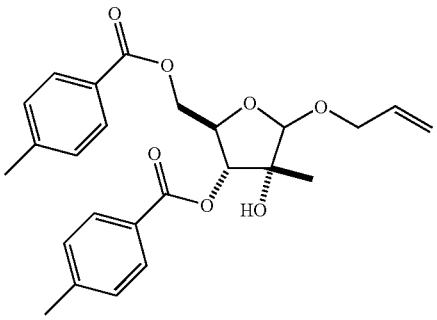

A solution of 2-C-methyl-3,5-di-O-(4-methylbenzoyl)-D-ribofuranose [preparation of which is described in M. Bio, et al. in "Practical Synthesis of a Potent Hepatitis Virus C Polymerase Inhibitor," *J. Org. Chem.*, 69: 6257-6266 (2004)] (2.00 g, 5.00 mmol), and pyridinium p-toluenesulfonate (627 mg, 2.5 mmol) in allyl alcohol (10 mL) was heated to 100° C. for 24 h. The volatile allyl alcohol was removed in vacuo, and the residue was purified by gradient column chromatography, using a mixture of ethyl acetate (EA) and hexanes as solvent (EA: 0 to 30%). In this fashion, the pure product was obtained. $^1$H NMR (500 MHz, CDCl$_3$): δ 7.93 (d, J=8.2 Hz, 2H), 7.88 (d, J=8.0 Hz, 2H), 7.23 (d, J=8.0 Hz, 2H), 7.15 (d, J=8.0 Hz, 2H), 5.85 (m, 1H), 5.56 (d, J=7.1 Hz, 1H), 5.26 (dd, J=17.4, 1.8 Hz, 1H), 5.18 (dd, J=10.5, 1.6 Hz, 1H), 4.88 (s, 1H), 4.43 to 4.60 (bm, 3H), 4.25 (ddt, J=13.3, 5.0, 1.6 Hz, 1H), 4.0 (dt, J=13.3, 5.7, 1.4 Hz, 1H), 2.42 (s, 3H), 2.28 (s, 3H), 1.41 (s, 3H). $^{13}$C NMR (500 MHz, CDCl$_3$): δ 166.29, 165.57, 144.41, 143.54, 133.76, 129.83, 129.73, 129.22, 128.93, 127.02, 126.28, 119.98, 107.01, 79.64, 78.32, 77.16, 68.23, 65.22, 21.66, 21.59, 20.00.

Step B:

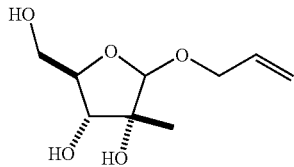

The diester from Step A (3.55 g, 8.059 mmol) was dissolved in anhydrous methanol (20 mL) and treated with a methanolic solution of sodium methoxide (5 mL, 0.5 M solution). Stirring at room temperature was continued for 2 h after which time the reaction was quenched by addition of 1N HCl (3 mL). The solvent was removed in vacuo, and the residue was purified by flash chromatography (SiO$_2$ column, 100% ethyl acetate, isocratic) to obtain the desired product in a form of a white powder.

$^1$H NMR (500 MHz, CDCl$_3$): δ 5.88 (m, 1H), 5.29 (dd, J=17.2, 1.4 Hz, 1H), 5.20 (dd, J=10.3, 1.2 Hz, 1H), 4.80 (s, 1H), 4.23 (dd, J=13.0, 5.0 Hz, 1H), 4.02 (m, 3H), 3.82 (dd, J=11.7, 2.5 Hz, 1H), 3.66 (dd, J=11.9, 3.7 Hz, 1H), 1.33 (s, 3H). $^{13}$C NMR (500 MHz, CDCl$_3$): δ 133.73, 117.46, 107.24, 83.64, 79.18, 74.86, 68.97, 62.97, 19.33.

Step C:

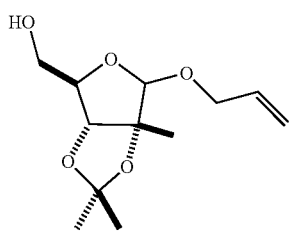

A solution of the triol from Step B (1.125 g, 5.51 mmol) in dichloromethane (6 mL) was treated with 2,2-dimethoxypropane (4 mL) and p-toluenesulfonic acid (187 mg) and the resulting mixture was stirred at room temperature for 2 h. The reaction mixture was then poured onto saturated aqueous sodium bicarbonate (20 mL) and extracted with dichloromethane (3×50 mL). The combined organic extracts were dried, and the solvent was removed at reduced pressure at ambient temperature. The resulting volatile product was used in the next step without additional purification. $^1$H NMR (500 MHz, CDCl$_3$): δ 5.90 (m, 1H), 5.30 (dd, J=15.6, 1.4 Hz, 1H), 5.22 (dd, J=10.5, 1.4 Hz, 1H), 4.49 (s, 1H), 4.26 (m, 2H), 3.69 (dd, J=12.4, 2.5 Hz, 1H), 3.61 (dd, J=12.4, 3.7 Hz, 1H), 1.46 (bs, 6H), 1.41 (s, 3H).

Step D:

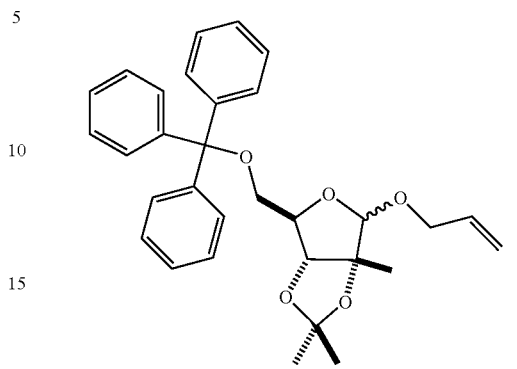

A solution of the alcohol from Step C (1.77 g, max 5.51 mmol) and trityl chloride (1.536 g, 5.51 mmol) in pyridine (6 mL) was stirred at 60° C. overnight. The solvent was removed in vacuo and the residue was purified by gradient chromatography using a mixture of ethyl acetate and hexanes (0% to 30% of ethyl acetate). The desired product was obtained in the form of a C-1 epimeric mixture (2:1). LCMS for C$_{31}$H$_{34}$O$_5$ calculated: 486.24, found 509.40 [M+Na]$^+$.

Step E:

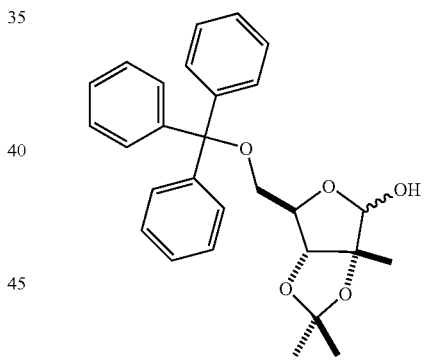

A solution of the allyl ether from Step D (800 mg, 1.6441 mmol), 1,3-bis(diphenylphosphino)propane nickel (II) dichloride (27 mg, 0.05 mmol) in diethyl ether (16 mL) was cooled to 0° C. and Dibal-H (2 mL, 1M solution in hexanes) was added dropwise. The mixture was stirred in the cold for 30 min and the reaction was then quenched with 2 mL of water. It was stirred at ambient temperature for 30 min, anhydrous magnesium sulfate was added (about 2 g), and the stirring was continued for another 30 min. The drying agent was filtered, the solvent was removed in vacuo, and the residue was purified by gradient column chromatography using ethyl acetate and hexanes as eluent (EA 0% to 70%). The desired product was obtained in the form of a C-1 epimeric mixture. LCMS for C$_{28}$H$_{30}$O$_5$ calculated: 446.21, found 469.30 [M+Na]$^+$.

Step F:

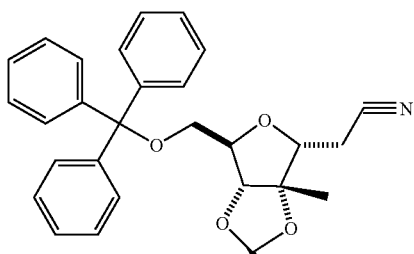

major

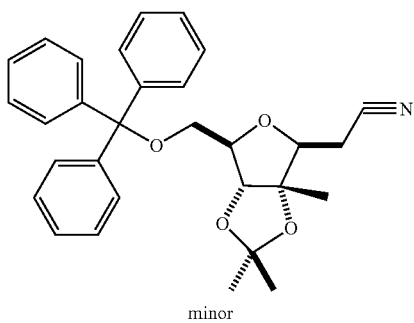

minor

A suspension of sodium hydride (120 mg, 3.0 mmol, 60% in mineral oil) in dimethoxyethane (DME, 5 mL) was cooled to 0° C. A solution of diethyl cyanomethylphosphonate (550 μL, 3.40 mmol) in DME was added dropwise, and the stirring was continued for 10 min at 0° C. A solution of the protected ribose from Step D (760 mg, 1.70 mmol) in DME (5.0 mL) was then added, cooling was removed and stirring continued for 4 h. The reaction mixture was partitioned between water (20 mL) and TBME (60 mL), and the aqueous phase was extracted with TBME two more times. The combined organic extracts were washed with brine, dried with anhydrous magnesium sulfate, filtered, and the solvent was removed in vacuo. The crude product was purified by gradient chromatography, using ethyl acetate and hexanes as eluent (EA 0% to 50%). Two C-1 epimers were obtained:

Major Epimer: $^1$H NMR (500 MHz, CDCl$_3$): δ 7.46 (m, 6H), 7.35 (m, 6H), 7.27 (m, 3H), 4.43 (d, J=0.9 Hz, 1H), 4.25 (t, J=4.80 Hz, 1H), 4.03 (dd, J=7.3, 5.7 Hz, 1H), 3.29 (dd, J=10.1, 5.3 Hz, 1H), 3.22 (dd, J 10.3, 4.6 Hz, 1H), 2.68 (ABq, J=16.7, 7.3 Hz, 2H), 1.50 (s, 3H), 1.44 (s, 3H) 1.43 (s, 3H). $^{13}$C NMR (500 MHz, CDCl$_3$): δ 143.37, 128.62, 127.94, 127.21, 117.59, 113.32, 89.21, 89.07, 87.39, 83.56, 81.62, 63.68, 27.73, 27.32, 22.98, 27.32, 22.97, 18.60. LCMS for C$_{30}$H$_{31}$O$_4$ calculated: 469.23, found 492.26 [M+Na]$^+$.

Minor Epimer: $^1$H NMR (500 MHz, CDCl$_3$): δ 7.48 (m, 6H), 7.34 (m, 6H), 7.28 (m, 3H), 4.20 (m, 2H), 4.05 (dd, J=7.8, 5.3 Hz, 1H), 3.33 (d, J=4.1 Hz, 1H), 2.61 (dd, J=16.7, 5.3 Hz, 1H), 2.52 (dd, J=16.7, 8.0 Hz, 1H), 1.55 (s, 3H), 1.38 (s, 3H), 1.37 (s, 3H). $^{13}$C NMR (500 MHz, CDCl$_3$): δ 143.58, 128.73, 127.83, 127.12, 116.95, 114.56, 87.61, 87.32, 87.00, 82.28, 80.94, 63.52, 28.11, 26.62, 18.69, 18.39.

LCMS for C$_{30}$H$_{31}$O$_4$ calculated: 469.23, found 492.26 [M+Na]$^+$.

Step G:

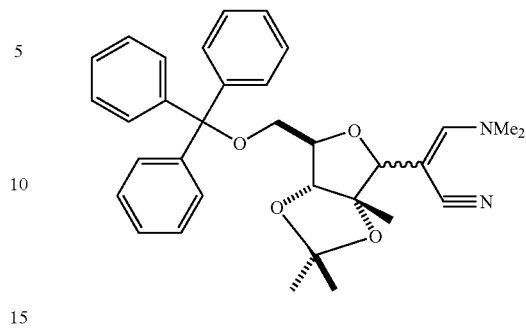

The solution of the nitrile from Step F (major isomer, 2.27 g, 4.83 mmol) in DMF (15 mL) was treated with bis(dimethylamino)methyl-tert-butyl-ether (5.05 g, 29 mmol) and stirred at 50° C. for 30 min. The reaction was quenched with water (30 mL) and the product was extracted with TBME (3×50 mL). The combined organic extracts were back-washed with brine, dried (sodium sulfate) and the solvent was removed in vacuo. The product so obtained was used in the subsequent step without any additional purification.

Step H:

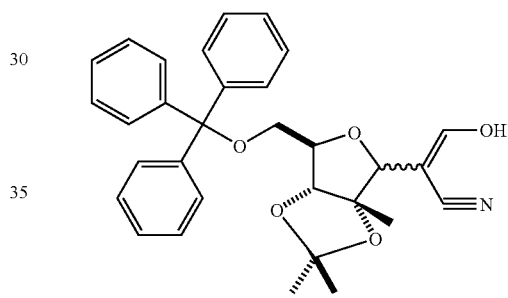

The crude product from Step G (2.50 g, 4.76 mmol) was vigorously stirred in a mixture of THF, acetic acid and water (1:1:1) for 1 h. The mixture was diluted with chloroform and washed with saturated solution of sodium bicarbonate. The aqueous phase was back-washed with chloroform, the combined organic extracts were dried (magnesium sulfate) and the solvent was removed in vacuo. The crude product was used in the subsequent step without any additional purification.

Step I:

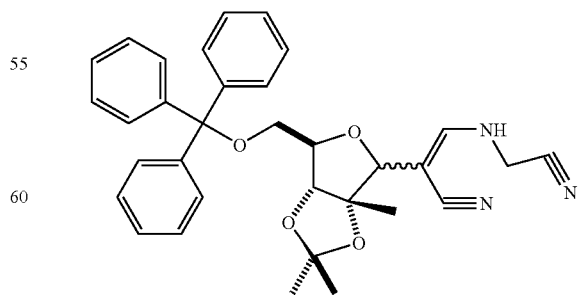

The crude product from Step H (2.19 g, 4.40 mmol) was dissolved in methanol (20 mL) and water was added (2.0 mL)

followed by sodium acetate (540 mg, 6.60 mmol) and aminoacetonitrile hydrochloride (610 mg, 6.60 mmol). The reaction mixture was stirred at ambient temperature over the weekend. It was then diluted with chloroform and washed with water. The aqueous phase was back-washed with chloroform, the combined organic phases were dried and the solvent was removed in vacuo. The crude product was used in the next step without purification.

Step J:

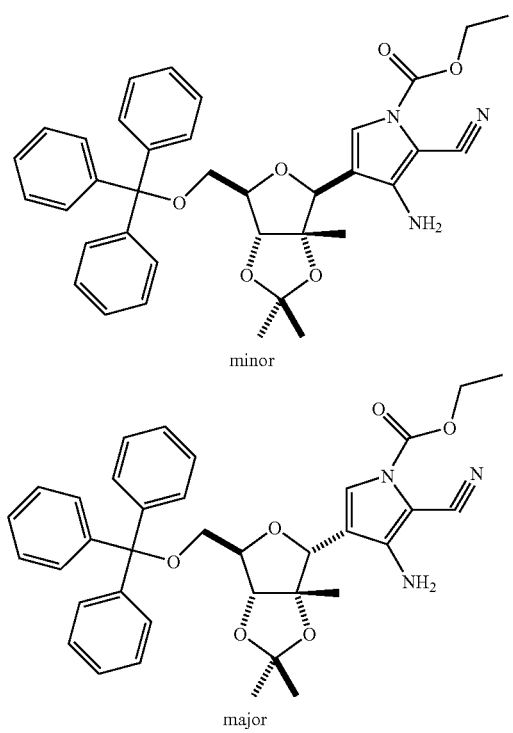

The solution of the crude product from Step I (2.44 g, 4.40 mmol) was dissolved in dichloromethane (20 mL), and DBU (1.34 g, 8.80 mmol) was added. To this mixture ethyl chloroformate (716 μL, 6.60 mmol) was added via syringe, and stirring at room temperature was continued for 2 h. At this time, LC-MS indicated full formation of the urethane, and additional DBU (1.34 g, 8.80 mmol) was added to induce the cyclization. The stirring at room temperature was continued overnight. The reaction mixture was diluted with chloroform (50 mL) and extracted with an aqueous solution of citric acid (10%, 2×50 mL). The combined aqueous phases were washed with chloroform, the combined organic extracts were dried (anhydrous sodium sulfate) and the solvent was removed in vacuo. The crude product was purified by column chromatography, using a mixture of dichloromethane and diethyl ether (98:2) as the eluent. Two epimers could be separated:

Major Epimer (Lower Rf): $^1$H NMR (500 MHz, CDCl$_3$): δ 7.48 (m, 6H, 7.34 (m, 6H), 7.26 (m, 3H), 5.31 (s, 1H), 4.71 (s, 1H), 4.47 (m, 3H), 4.33 (t, J=5.0 Hz, 1H), 3.33 (dd, J=10.3, 5.3 Hz, 1H), 3.27 (dd, J=10.3, 5.0 Hz, 1H), 1.57 (s, 3H), 1.45 (m, 9H). $^{13}$C NMR (500 MHz, CDCl$_3$): δ 143.39, 128.61, 127.94, 127.25, 123.55, 123.00, 90.40, 88.07, 87.35, 83.19, 82.59, 64.29, 63.37, 27.63, 27.53, 14.08. LCMS for C$_{36}$H$_{37}$N$_3$O$_6$ calculated: 607.27, found 630.50 [M+Na]$^+$.

Minor Epimer (Higher Rf): $^1$H NMR (500 MHz, CDCl$_3$): δ 7.52, (m, 6H), 7.36 (m, 6H), 7.30 (m, 3H), 4.76 (s, 1H), 4.57 (bs, 2H), 4.44 (q, J=7.1 Hz, 2H), 4.40 (d, J=2.50Hz, 1H), 4.32 (dd, J=6.7, 3.9 Hz, 1H), 3.43 (dd, J=10.5, 3.5 Hz, 1H), 3.36 (dd, J=10.5, 4.5 Hz, 1H), 1.63 (s, 3H), 1.47 (t, J=7.1 Hz, 2H), 1.43 (s, 3H), 1.24 (s, 3H). $^{13}$C NMR (500 MHz, CDCl$_3$): δ 146.11, 143.57, 128.72, 127.81, 127.15, 122.20, 114.69, 89.15, 86.95, 86.90, 82.68, 81.68, 64.18, 63.78, 31.54, 28.08, 26.50, 22.60, 19.62, 14.10, 14.07. LCMS for C$_{36}$H$_{37}$N$_3$O$_6$ calculated: 607.27, found 630.40 [M+Na]$^+$.

Step K:

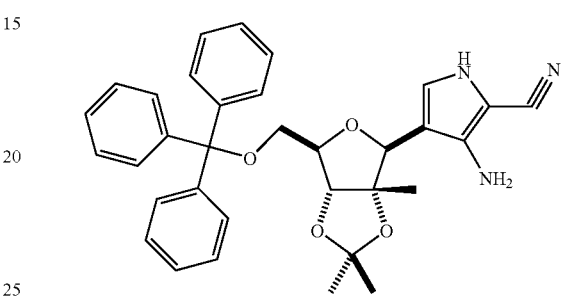

A solution of the urethane from Step J (minor isomer, 207 mg, 0.341 mmol) in ethanol (6 mL) was treated with potassium carbonate (100 mg) and stirred at ambient temperature for 1 h. The reaction mixture was diluted with 85:15 chloroform/iPrOH (10 mL) and shaken up with water (5 mL). The aqueous layer was separated and extracted twice with 85:15 chloroform/iPrOH. The combined organic extracts were dried with anhydrous sodium sulfate, and the solvent was removed in vacuo. The crude product was used in the next step without any additional purification. $^1$H NMR (500 MHz, CDCl$_3$): δ 8.0 (s, 1H), 7.56 (m, 6H), 7.33 (m, 6H), 7.27 (m, 3H), 6.68 (d, J=2.1 Hz, 1H), 4.82 (s, 1H), 4.33 (d, J=2.80 1H), 4.29 (m, 1H), 4.12 (s, 2H), 3.42 (dd, J=10.3, 3.9 Hz, 1H), 3.35 (dd, J=10.3, 4.6 Hz, 1H), 1.63 (s, 3H), 1.41 (s, 3H), 1.21 (s, 3H). $^{13}$C NMR (500 MHz, CDCl$_3$): δ 143.68, 141.72, 128.73, 127.83, 127.13, 120.84, 114.94, 114.51, 109.47, 89.54, 87.04, 86.89, 86.43, 82.59, 82.41, 63.71, 31.57, 28.21, 26.69, 22.63, 19.80, 14.10.

Step L:

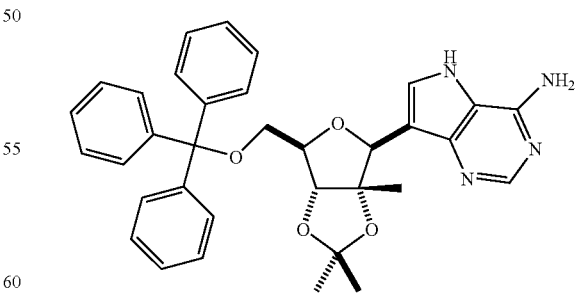

A solution of the aminonitrile preparation from Step K (182 mg, 0.339 mmol), formamidine acetate (354 mg, 3.40 mmol) in ethanol (6 mL) was heated with stirring in a sealed tube to 90° C. for 5 h. The reaction vessel was allowed to cool to ambient temperature, the reaction mixture was transferred into a 10-mL flask and the solvent was removed in vacuo. The residue was partitioned between water (10 mL) and TBME (30 mL), and the aqueous phase was washed with TBME (3×30 mL). The combined organic extracts were back-washed with brine, dried and the solvent was removed in vacuo to yield crude desired product. It was further purified by preparative TLC (9:1 dichloromethane/methanol as eluent) to yield pure product. LCMS for $C_{34}H_{34}N_4O_4$ calculated: 562.26, found 563.40 $[M+H]^+$. $^1H$ NMR (500 MHz, $CD_3OD$): δ 8.16 (s, 1H), 7.50 (m, 6H), 7.32 (m, 6H), 7.26 (m, 4H), 5.29 (s, 1H), 4.30 (d, J=3.0 Hz, 1H), 4.23 (m, 1H), 3.40 (dd, J=5.0, 1.6 Hz, 2H), 1.64 (s, 3H), 1.38 (s, 3H), 1.15 (s, 3H). $^{13}C$ NMR (500 MHz, $CD_3OD$): δ 149.92, 145.22, 129.95, 129.90, 129.19, 128.88, 128.25, 115.84, 112.41, 90.66, 89.07, 88.26, 83.31, 83.22, 65.27, 28.59, 27.29, 21.77.

Step M:

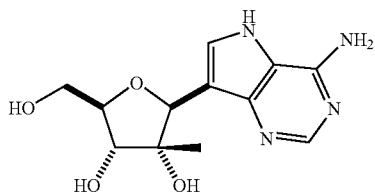

A solution of the protected nucleoside from Step L (105 mg, 0.1966 mmol) was dissolved in dry methanol (2.0 mL) and treated with a dioxane solution of hydrogen chloride (4N, 200 µL). Stirring at ambient temperature was continued for 24 h, after which time the solvent was removed in vacuo. The residue was distributed between water (6 mL) and chloroform (20 mL), and after separation, the aqueous phase was extracted with chloroform three more times. The aqueous phase was heated briefly to reflux with a spatula tip of charcoal, micro-filtered, and the solvent was evaporated to dryness. The residue was picked up into 2 mL of acetonitrile, and after crystallization, the supernatant was removed with a pipette. The solid was washed two more times with acetonitrile, and dried on high-vacuum to afford the desired product. $^1H$ NMR (600 MHz, $CD_3OD$): δ 8.36 (s, 1H, 2-H), 7.73 (s, 1H, 8-H), 5.11 (s, 1H, 1'-H), 4.05 (dd, J=11.8, 2.5Hz, 1H, 5''-H), 3.97 (dt, J=7.7, 2.5 Hz, 1H, 4'-H), 3.93 (dd, J=11.7, 2.6 Hz, 5'-H), 3.82 (d, J=7.6 Hz, 1H, 3'-H), 2.04 (s, 3H, $C_2$'-$CH_3$). $^{13}C$ NMR (600 MHz, $CD_3OD$): δ 154.50 ($C_6$), 145.91 ($C_7$), 133.59, 130.49 ($C_2$), 84.66 ($C_1$'), 83.87 ($C_4$'), 79.74 ($C_2$'), 75.36 ($C_3$'), 61.16 ($C_5$'), 22.60 ($C_2$'-$CH_3$). LCMS for $C_{12}H_{16}N_4O_4$ calculated: 280.12, found 281.30 $[M+H]^+$.

EXAMPLE 5

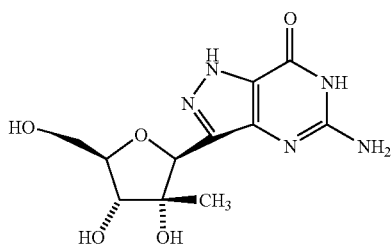

5-Amino-3-(2-C-methyl-β-D-ribofuranosyl)-1H-pyrazolo[4,3-d]pyrimidin-7(6H)-one

Step A:

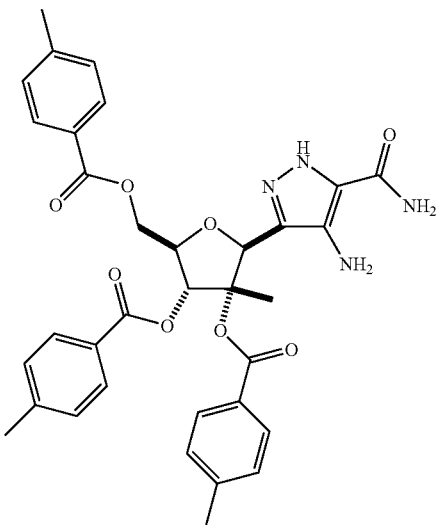

This compound is synthesized from the intermediate of Example 1, Step H following a procedure analogous to that described in Example 1, Step C.

Step B:

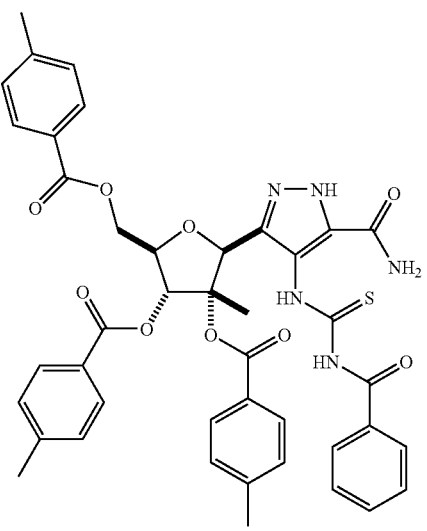

This compound is synthesized from the intermediate of Step A following a procedure analogous to that described by L. B. Townsend et al. in *J. Am. Chem. Soc.*, 104:1073-1077 (1982).

Step C:

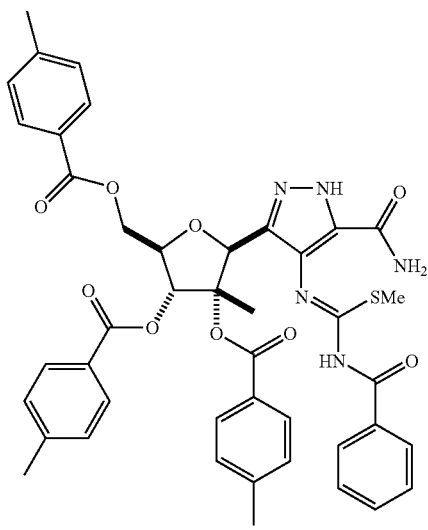

This compound is synthesized from the intermediate of Step B following a procedure analogous to that described by L. B. Townsend et al. in *J. Am. Chem. Soc.*, 104:1073-1077 (1982).

Step D:

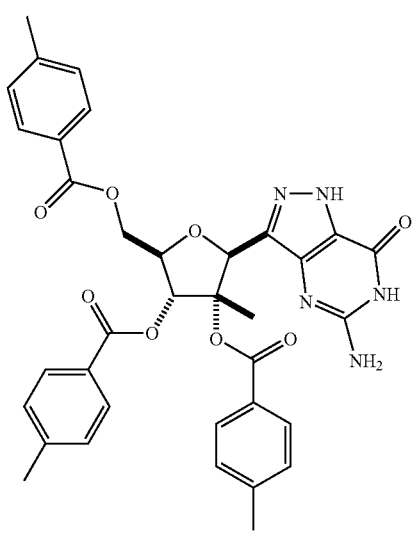

This compound is synthesized from the intermediate of Step C following a procedure analogous to that described by L. B. Townsend et al. in *J. Am. Chem. Soc.*, 104: 1073-1077 (1982).

Step E:

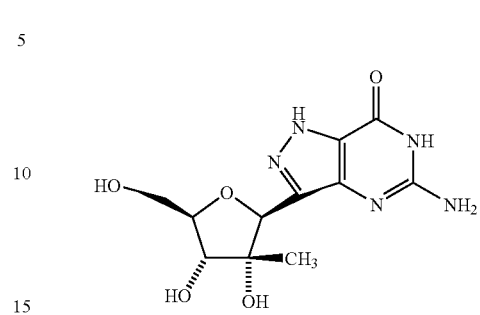

This compound is synthesized from the intermediate of Step D using a procedure analogous to that described by L. Kalvoda in *Coll. Czech. Chem. Comm.*, 43: 1431-1437 (1977).

EXAMPLE 6

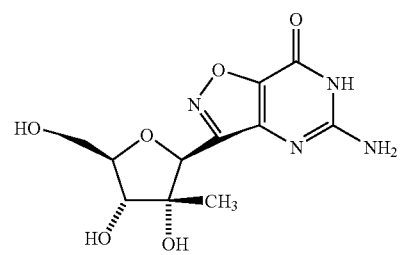

5-Amino-3-(2-C-methyl-β-D-ribofuranosyl)-isoxazolo[4,5-d]pyrimidin-7(6H)-one

This compound is synthesized from the intermediate of Example 2, Step E following the methods described for Example 5.

EXAMPLE 7

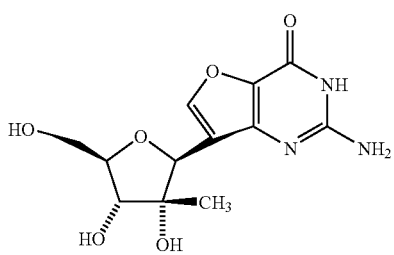

2-Amino-7-(2-C-methyl-β-D-ribofuranosyl)-furo[3,2-d]pyrimidin-4(3H)-one

This compound is synthesized from the intermediate of Example 3, Step D following the methods described for Example 5.

EXAMPLE 8

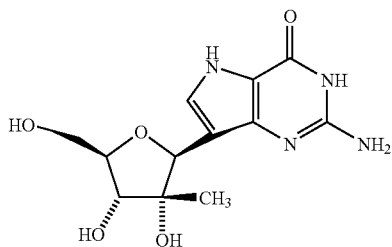

2-Amino-7-(2-C-methyl-β-D-ribofuranosyl)-5H-pyrrolo[3,2-d]pyrimidin-4(3H)-one

This compound is synthesized from the intermediate of Example 4, Step C following the methods described for Example 5.

Biological Assays:

The assays employed to measure the inhibition of HCV NS5B polymerase and HCV replication are described below.

The effectiveness of the compounds of the present invention as inhibitors of HCV NS5B RNA-dependent RNA polymerase (RdRp) was measured in the following assay.

A. Assay for Inhibition of HCV NS5B Polymerase:

This assay was used to measure the ability of the nucleoside derivatives of the present invention to inhibit the enzymatic activity of the RNA-dependent RNA polymerase (NS5B) of the hepatitis C virus (HCV) on a heteromeric RNA template.

Procedure:

Assay Buffer Conditions: (50 µL-total/reaction)
  20 mM Tris, pH 7.5
  50 µM EDTA
  5 mM DTT
  2 mM MgCl$_2$
  80 mM KCl
  0.4 U/µL RNAsin (Promega, stock is 40 units/µL)
  0.75 µg t500 (a 500-nt RNA made using T7 runoff transcription with a sequence from the NS2/3 region of the hepatitis C genome)
  1.6 µg purified hepatitis C NS5B (form with 21 amino acids C-terminally truncated)
  1 µM A,C,U,GTP (Nucleoside triphosphate mix)
  [alpha-$^{32}$P]-GTP or [alpha-$^{33}$P]-GTP The compounds were tested at various concentrations up to 100 µM final concentration.

An appropriate volume of reaction buffer was made including enzyme and template t500. Nucleoside derivatives of the present invention were pipetted into the wells of a 96-well plate. A mixture of nucleoside triphosphates (NTP's), including the radiolabeled GTP, was made and pipetted into the wells of a 96-well plate. The reaction was initiated by addition of the enzyme-template reaction solution and allowed to proceed at room temperature for 1-2 h.

The reaction was quenched by addition of 20 µL 0.5M EDTA, pH 8.0. Blank reactions in which the quench solution was added to the NTPs prior to the addition of the reaction buffer were included.

50 µL of the quenched reaction were spotted onto DE81 filter disks (Whatman) and allowed to dry for 30 min. The filters were washed with 0.3 M ammonium formate, pH 8 (150 ml/wash until the cpm in 1 mL wash is less than 100, usually 6 washes). The filters were counted in 5-mL scintillation fluid in a scintillation counter.

The percentage of inhibition was calculated according to the following equation:

% Inhibition=[1−(cpm in test reaction−cpm in blank)/(cpm in control reaction−cpm in blank)]×100.

Representative compounds tested in the HCV NS5B polymerase assay exhibited IC$_{50}$'s less than 100 micromolar.

B. Assay for Inhibition of HCV RNA Replication:

The compounds of the present invention were also evaluated for their ability to affect the replication of Hepatitis C Virus RNA in cultured hepatoma (HuH-7) cells containing a subgenomic HCV Replicon. The details of the assay are described below. This Replicon assay is a modification of that described in V. Lohmann, F. Korner, J-O. Koch, U. Herian, L. Theilmann, and R. Bartenschlager, "Replication of a Subgenomic Hepatitis C Virus RNAs in a Hepatoma Cell Line," Science 285:110 (1999).

Protocol:

The assay was an in situ Ribonuclease protection, Scintillation Proximity based-plate assay (SPA). 10,000-40,000 cells were plated in 100-200 µL of media containing 0.8 mg/mL G418 in 96-well cytostar plates (Amersham). Compounds were added to cells at various concentrations up to 100 µM in 1% DMSO at time 0 to 18 h and then cultured for 24-96 h. Cells were fixed (20 min, 10% formalin), permeabilized (20 min, 0.25% Triton X-100/PBS) and hybridized (overnight, 50° C.) with a single-stranded $^{33}$P RNA probe complementary to the (+) strand NS5B (or other genes) contained in the RNA viral genome. Cells were washed, treated with RNAse, washed, heated to 65° C. and counted in a Top-Count. Inhibition of replication was read as a decrease in counts per minute (cpm).

Human HuH-7 hepatoma cells, which were selected to contain a subgenomic replicon, carry a cytoplasmic RNA consisting of an HCV 5' non-translated region (NTR), a neomycin selectable marker, an EMCV IRES (internal ribosome entry site), and HCV non-structural proteins NS3 through NS5B, followed by the 3' NTR.

Representative compounds tested in the replication assay exhibited EC$_{50}$'s less than 100 micromolar.

The nucleoside derivatives of the present invention were also evaluated for cellular toxicity and anti-viral specificity in the counterscreens described below.

C. Counterscreens:

The ability of the C-nucleoside derivatives of the present invention to inhibit human DNA polymerases was measured in the following assays.

a. Inhibition of Human DNA Polymerases alpha and beta:

Reaction Conditions:

50 µL reaction volume

Reaction Buffer Components:
20 mM Tris-HCl, pH 7.5

200 μg/mL bovine serum albumin
100 mM KCl
2 mM β-mercaptoethanol
10 mM MgCl$_2$
1.6 μM dA, dG, dC, dTTP
α-$^{33}$P-dATP Enzyme and Template:
0.05 mg/mL gapped fish sperm DNA template
0.01 U/μL DNA polymerase α or β

Preparation of Gapped Fish Sperm DNA Template:
Add 5 μL 1M MgCl$_2$ to 500 μL activated fish sperm DNA (USB 70076);
Warm to 37° C. and add 30 μL of 65 U/μL of exonuclease II (GibcoBRL 18013-011);
Incubate 5 min at 37° C.;
Terminate reaction by heating to 65° C. for 10 min;
Load 50-100 μL aliquots onto Bio-spin 6 chromatography columns (Bio-Rad 732-6002) equilibrated with 20 mM Tris-HCl, pH 7.5;
Elute by centrifugation at 1,000×g for 4 min;
Pool eluate and measure absorbance at 260 nm to determine concentration.

The DNA template was diluted into an appropriate volume of 20 mM Tris-HCl, pH 7.5 and the enzyme was diluted into an appropriate volume of 20 mM Tris-HCl, containing 2 mM β-mercaptoethanol, and 100 mM KCl. Template and enzyme were pipetted into microcentrifuge tubes or a 96 well plate. Blank reactions excluding enzyme and control reactions excluding test compound were also prepared using enzyme dilution buffer and test compound solvent, respectively. The reaction was initiated with reaction buffer with components as listed above. The reaction was incubated for 1 hour at 37° C. The reaction was quenched by the addition of 20 μL 0.5M EDTA. 50 μL of the quenched reaction was spotted onto Whatman DE81 filter disks and air dried. The filter disks were repeatedly washed with 150 mL 0.3M ammonium formate, pH 8 until 1 mL of wash is <100 cpm. The disks were washed twice with 150 mL absolute ethanol and once with 150 mL anhydrous ether, dried and counted in 5 mL scintillation fluid.

The percentage of inhibition was calculated according to the following equation: % inhibition=[1−(cpm in test reaction−cpm in blank)/
(cpm in control reaction−cpm in blank)]×100.

b. Inhibition of Human DNA Polymerase Gamma:

The potential for inhibition of human DNA polymerase gamma was measured in reactions that included 0.5 ng/μL enzyme; 10 μM dATP, dGTP, dCTP, and TTP; 2 μCi/reaction [α-$^{33}$P]-dATP, and 0.4 μg/μL activated fish sperm DNA (purchased from US Biochemical) in a buffer containing 20 mM Tris pH8, 2 mM β-mercaptoethanol, 50 mM KCl, 10 mM MgCl$_2$, and 0.1 μg/μL BSA. Reactions were allowed to proceed for 1 h at 37° C. and were quenched by addition of 0.5 M EDTA to a final concentration of 142 mM. Product formation was quantified by anion exchange filter binding and scintillation counting. Compounds were tested at up to 50 μM.

The percentage of inhibition was calculated according to the following equation: % inhibition=[1−(cpm in test reaction−cpm in blank)/
(cpm in control reaction−cpm in blank)]×100.

The ability of the nucleoside derivatives of the present invention to inhibit HIV infectivity and HIV spread was measured in the following assays.

c. HIV Infectivity Assay

Assays were performed with a variant of HeLa Magi cells expressing both CXCR4 and CCR5 selected for low background β-galactosidase (β-gal) expression. Cells were infected for 48 h, and β-gal production from the integrated HIV-1 LTR promoter was quantified with a chemiluminescent substrate (Galactolight Plus, Tropix, Bedford, Mass.). Inhibitors were titrated (in duplicate) in twofold serial dilutions starting at 100 μM; percent inhibition at each concentration was calculated in relation to the control infection.

d. Inhibition of HIV Spread

The ability of the compounds of the present invention to inhibit the spread of the human immunedeficiency virus (HIV) was measured by the method described in U.S. Pat. No. 5,413,999 (May 9, 1995), and J. P. Vacca, et al., *Proc. Natl. Acad. Sci.*, 91: 4096-4100 (1994), which are incorporated by reference herein in their entirety.

The C-nucleoside derivatives of the present invention were also screened for cytotoxicity against cultured hepatoma (HuH-7) cells containing a subgenomic HCV Replicon in an MTS cell-based assay as described in the assay below. The HuH-7 cell line is described in H. Nakabayashi, et al., *Cancer Res.*, 42: 3858 (1982).

e. Cytotoxicity Assay:

Cell cultures were prepared in appropriate media at concentrations of approximately 1.5×10$^5$ cells/mL for suspension cultures in 3 day incubations and 5.0×10$^4$ cells/mL for adherent cultures in 3 day incubations. 99 μL of cell culture was transferred to wells of a 96-well tissue culture treated plate, and 1 μL of 100-times final concentration of the test compound in DMSO was added. The plates were incubated at 37° C. and 5% CO$_2$ for a specified period of time. After the incubation period, 20 μL of CellTiter 96 Aqueous One Solution Cell Proliferation Assay reagent (MTS) (Promega) was added to each well and the plates were incubated at 37° C. and 5% CO$_2$ for an additional period of time up to 3 h. The plates were agitated to mix well and absorbance at 490 nm was read using a plate reader. A standard curve of suspension culture cells was prepared with known cell numbers just prior to the addition of MTS reagent. Metabolically active cells reduce MTS to formazan. Formazan absorbs at 490 nm. The absorbance at 490 nm in the presence of compound was compared to absorbance in cells without any compound added.

Reference: Cory, A. H. et al., "Use of an aqueous soluble tetrazolium/formazan assay for cell growth assays in culture," *Cancer Commun.* 3: 207 (1991).

The following assays were employed to measure the activity of the compounds of the present invention against other RNA-dependent RNA viruses:

a. Determination of In Vitro Antiviral Activity of Compounds Against Rhinovirus (Cytopathic Effect Inhibition Assay):

Assay conditions are described in the article by Sidwell and Huffman, "Use of disposable microtissue culture plates for antiviral and interferon induction studies," *Appl. Microbiol.* 22: 797-801 (1971).

Viruses:

Rhinovirus type 2 (RV-2), strain HGP, was used with KB cells and media (0.1% NaHCO$_3$, no antibiotics) as stated in the Sidwell and Huffman reference. The virus, obtained from the ATCC, was from a throat swab of an adult male with a mild acute febrile upper respiratory illness.

Rhinovirus type 9 (RV-9), strain 211, and rhinovirus type 14 (RV-14), strain Tow, were also obtained from the American Type Culture Collection (ATCC) in Rockville, Md. RV-9 was from human throat washings and RV-14 was from a throat swab of a young adult with upper respiratory illness. Both of these viruses were used with HeLa Ohio-1 cells (Dr. Fred Hayden, Univ. of Va.) which were human cervical epitheloid carcinoma cells. MEM (Eagle's minimum essential medium) with 5% Fetal Bovine serum (FBS) and 0.1% $NaHCO_3$ was used as the growth medium.

Antiviral test medium for all three virus types was MEM with 5% FBS, 0.1% $NaHCO_3$, 50 µg gentamicin/mL, and 10 mM $MgCl_2$.

2000 µg/mL was the highest concentration used to assay the compounds of the present invention. Virus was added to the assay plate approximately 5 min after the test compound. Proper controls were also run. Assay plates were incubated with humidified air and 5% $CO_2$ at 37° C. Cytotoxicity was monitored in the control cells microscopically for morphologic changes. Regression analysis of the virus CPE data and the toxicity control data gave the ED50 (50% effective dose) and CC50 (50% cytotoxic concentration). The selectivity index (SI) was calculated by the formula: SI=CC50÷ED50.

b. Determination of In Vitro Antiviral Activity of Compounds Against Dengue, Banzi, and Yellow Fever (CPE Inhibition Assay)

Assay details are provided in the Sidwell and Huffman reference above.

Viruses:

Dengue virus type 2, New Guinea strain, was obtained from the Center for Disease Control. Two lines of African green monkey kidney cells were used to culture the virus (Vero) and to perform antiviral testing (MA-104). Both Yellow fever virus, 17D strain, prepared from infected mouse brain, and Banzi virus, H 336 strain, isolated from the serum of a febrile boy in South Africa, were obtained from ATCC. Vero cells were used with both of these viruses and for assay.

Cells and Media:

MA-104 cells (BioWhittaker, Inc., Walkersville, Md.) and Vero cells (ATCC) were used in Medium 199 with 5% FBS and 0.1% $NaHCO_3$ and without antibiotics.

Assay medium for dengue, yellow fever, and Banzi viruses was MEM, 2% FBS, 0.18% $NaHCO_3$ and 50 µg gentamicin/mL.

Antiviral testing of the compounds of the present invention was performed according to the Sidwell and Huffman reference and similar to the above rhinovirus antiviral testing. Adequate cytopathic effect (CPE) readings were achieved after 5-6 days for each of these viruses.

c. Determination of In Vitro Antiviral Activity of Compounds Against West Nile Virus (CPE Inhibition Assay)

Assay details are provided in the Sidwell and Huffman reference cited above. West Nile virus, New York isolate derived from crow brain, was obtained from the Center for Disease Control. Vero cells were grown and used as described above. Test medium was MEM, 1% FBS, 0.1% $NaHCO_3$ and 50 µg gentamicin/mL.

Antiviral testing of the compounds of the present invention was performed following the methods of Sidwell and Huffman which are similar to those used to assay for rhinovirus activity. Adequate cytopathic effect (CPE) readings were achieved after 5-6 days.

d. Determination of In Vitro Antiviral Activity of Compounds Against Rhino, Yellow Fever, Dengue. Banzi, and West Nile Viruses (Neutral Red Uptake Assay)

After performing the CPE inhibition assays above, an additional cytopathic detection method was used which is described in "Microtiter Assay for Interferon: Microspectrophotometric Quantitation of Cytopathic Effect," *Appl. Environ. Microbiol.* 31: 35-38 (1976). A Model EL309 microplate reader (Bio-Tek Instruments Inc.) was used to read the assay plate. ED50's and CD50's were calculated as above.

Example of a Pharmaceutical Formulation

As a specific embodiment of an oral composition of a compound of the present invention, 50 mg of the compound of Example 1 or Example 2 is formulated with sufficient finely divided lactose to provide a total amount of 580 to 590 mg to fill a size O hard gelatin capsule.

While the invention has been described and illustrated in reference to specific embodiments thereof, those skilled in the art will appreciate that various changes, modifications, and substitutions can be made therein without departing from the spirit and scope of the invention. For example, effective dosages other than the preferred doses as set forth hereinabove may be applicable as a consequence of variations in the responsiveness of the human being treated for severity of the HCV infection. Likewise, the pharmacologic response observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended therefore that the invention be limited only by the scope of the claims which follow and that such claims be interpreted as broadly as is reasonable.

What is claimed is:
1. A compound of the structural formula I:

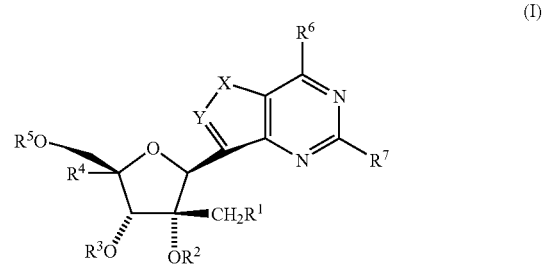

(I)

or a pharmaceutically acceptable salt thereof; wherein
X is O, S, or $NR^8$;
Y is $CR^{11}$ or N;
$R^1$ is selected from the group consisting of hydrogen, fluoro, azido, amino, hydroxy, $C_{1-3}$ alkoxy, mercapto, and $C_{1-3}$ alkylthio;
$R^2$ and $R^3$ are each independently selected from the group consisting of hydrogen, methyl, $C_{1-16}$ alkylcarbonyl, $C_{2-18}$ alkenylcarbonyl, $C_{1-10}$ alkyloxycarbonyl, $C_{3-6}$ cycloalkylcarbonyl, $C_{3-6}$ cycloalkyloxycarbonyl, $CH_2O(C=O)C_{1-4}$ alkyl, $CH(C_{1-4}$ alkyl)$O(C=O)C_{1-4}$ alkyl, or an amino acyl residue of structural formula

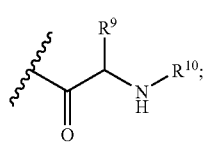

$R^4$ is hydrogen, azido, methyl, hydroxymethyl, or fluoromethyl;

$R^5$ is hydrogen, $C_{1-10}$ alkylcarbonyl, phosphoryl or a cyclic prodrug ester thereof, diphosphoryl, triphosphoryl, $C_{2-18}$ alkenylcarbonyl, $C_{1-10}$ alkyloxycarbonyl, $C_{3-6}$ cycloalkylcarbonyl, $C_{3-6}$ cycloalkyloxycarbonyl, $CH_2O(C=O)C_{1-4}$ alkyl, $CH(C_{1-4}$ alkyl)$O(C=O)C_{1-4}$ alkyl, or an amino acyl residue of structural formula

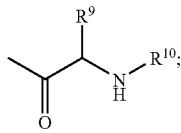

$R^6$ and $R^7$ are each independently hydrogen, hydroxy, halogen, $C_{1-4}$ alkoxy, amino, $C_{1-4}$ alkylamino, di($C_{1-4}$ alkyl)amino, $C_{3-6}$ cycloalkylamino, di($C_{3-6}$ cycloalkyl)amino, benzylamino, dibenzylamino, or $C_{4-6}$ heterocycloalkyl, wherein alkyl, cycloalkyl, benzyl, and heterocycloalkyl are unsubstituted or substituted with one to five groups independently selected from halogen, hydroxy, amino, $C_{1-4}$ alkyl, and $C_{1-4}$ alkoxy;

$R^8$ is hydrogen or $C_{1-4}$ alkyl;

$R^9$ is hydrogen, $C_{1-5}$ alkyl, or phenyl $C_{0-2}$ alkyl;

$R^{10}$ is hydrogen, $C_{1-4}$ alkyl, $C_{1-4}$ acyl, benzoyl, $C_{1-4}$ alkyloxycarbonyl, phenyl $C_{0-2}$ alkyloxycarbonyl, $C_{1-4}$ alkylaminocarbonyl, phenyl $C_{0-2}$ alkylaminocarbonyl, $C_{1-4}$ alkylsulfonyl, or phenyl $C_{0-2}$ alkylsulfonyl; and $R^{11}$ is hydrogen, methyl, halogen, azido, or amino;

and provided that when Y is CH and X is NH and $R^1=R^2=R^3=R^4=R^5=$hydrogen, then $R^6$ is not OH.

2. The compound of claim 1 wherein Y is CH, and X is O, S, or $NR^8$.

3. The compound of claim 2 wherein X is O.

4. The compound of claim 2 wherein X is $NR^8$.

5. The compound of claim 4 wherein $R^8$ is hydrogen.

6. The compound of claim 1 wherein Y is N, and X is O, S, or $NR^8$.

7. The compound of claim 6 wherein X is O.

8. The compound of claim 6 wherein X is $NR^8$.

9. The compound of claim 8 wherein $R^8$ is hydrogen.

10. The compound of claim 1 wherein $R^1$ and $R^4$ are both hydrogen.

11. The compound of claim 10 wherein $R^2$, $R^3$, and $R^5$ are hydrogen.

12. The compound of claim 11 wherein $R^6$ and $R^7$ are each independently hydrogen, amino, fluoro, or hydroxy.

13. The compound of claim 1 wherein Y is N; X is $NR^8$; $R^1$, $R^2$, $R^3$, $R^4$, and $R^5$ are hydrogen; and $R^6$ and $R^7$ are each independently hydrogen, amino, fluoro, or hydroxy.

14. The compound of claim 13 wherein $R^8$ is hydrogen.

15. The compound of claim 1 wherein Y is CH; X is $NR^8$; $R^1$, $R^2$, $R^3$, $R^4$, and $R^5$ are hydrogen; and $R^6$ and $R^7$ are each independently hydrogen, amino, fluoro, or hydroxy.

16. The compound of claim 15 wherein $R^8$ is hydrogen, and $R^6$ is hydrogen, amino, or fluoro.

17. The compound of claim 1 wherein Y is N; X is O; $R^1$, $R^2$, $R^3$, $R^4$, and $R^5$ are hydrogen; and $R^6$ and $R^7$ are each independently hydrogen, amino, fluoro, or hydroxy.

18. The compound of claim 17 wherein $R^8$ is hydrogen.

19. The compound of claim 1 wherein Y is CH; X is O; $R^1$, $R^2$, $R^3$, $R^4$, and $R^5$ are hydrogen; and $R^6$ and $R^7$ are each independently hydrogen, amino, fluoro, or hydroxy.

20. The compound of claim 19 wherein $R^8$ is hydrogen.

21. The compound of claim 1 which is selected from the group consisting of:
- 4-amino-7-(2-C-methyl-β-D-ribofuranosyl)-furo[3,2-d]pyrimidine;
- 2-amino-7-(2-C-methyl-β-D-ribofuranosyl)-furo[3,2-d]pyrimidin-4(3H)-one;
- 4-amino-7-(2-C-methyl-β-D-ribofuranosyl)-thieno[3,2-d]pyrimidine;
- 2-amino-7-(2-C-methyl-β-D-ribofuranosyl)-thieno[3,2-d]pyrimidin-4(3H)-one;
- 4-amino-7-(2-C-methyl-β-D-ribofuranosyl)-5H-pyrrolo[3,2-d]pyrimidine;
- 7-amino-3-(2-C-methyl-β-D-ribofuranosyl)-isoxazolo[4,5-d]pyrimidine;
- 5-amino-3-(2-C-methyl-β-D-ribofuranosyl)-isoxazolo[4,5-d]pyrimidin-7(6H)-one;
- 7-amino-3-(2-C-methyl-β-D-ribofuranosyl)-1H-pyrazolo[4,3-d]pyrimidine; and
- 5-amino-3-(2-C-methyl-β-D-ribofuranosyl)-1H-pyrazolo[4,3-d]pyrimidin-7(6H)-one;

or a pharmaceutically acceptable salt thereof.

22. A pharmaceutical composition comprising a compound of claim 1 and a pharmaceutically acceptable carrier.

23. A method of treating hepatitis C virus (HCV) infection comprising administering to a mammal in need of such treatment a therapeutically effective amount of a compound according to claim 1.

* * * * *